US007901690B2

(12) United States Patent
Lu et al.

(10) Patent No.: US 7,901,690 B2
(45) Date of Patent: Mar. 8, 2011

(54) POLYVALENT, PRIMARY HIV-1 GLYCOPROTEIN DNA VACCINES AND VACCINATION METHODS

(75) Inventors: Shan Lu, Franklin, MA (US); Shixia Wang, Northborough, MA (US); Ranajit Pal, Gaithersburg, MD (US); Vaniambadi Kalyanaraman, Rockville, MD (US); Stephen Charles Whitney, Silver Spring, MD (US); Tim Keen, Silver Spring, MD (US); Balachandran Nair, Gaithersburg, MD (US); Phillip Markham, Mount Airy, MD (US)

(73) Assignees: University of Massachusetts, Boston, MA (US); Advanced Bioscience Laboratories, Kensington, MD (US)

( * ) Notice: Subject to any disclaimer, the term of this patent is extended or adjusted under 35 U.S.C. 154(b) by 59 days.

(21) Appl. No.: 10/728,195

(22) Filed: Dec. 3, 2003

(65) Prior Publication Data

US 2004/0191269 A1 Sep. 30, 2004

Related U.S. Application Data

(60) Provisional application No. 60/430,732, filed on Dec. 3, 2002, provisional application No. 60/503,907, filed on Sep. 19, 2003.

(51) Int. Cl.

| | |
|---|---|
| ***A61K 39/21*** | (2006.01) |
| ***A61K 39/295*** | (2006.01) |
| ***C12N 15/00*** | (2006.01) |
| ***C12P 15/09*** | (2006.01) |

(52) U.S. Cl. ................ 424/188.1; 424/184.1; 424/186.1; 424/187.1; 424/202.1; 435/320.1; 435/69.1

(58) Field of Classification Search ............... 424/192.1; 536/23.72; 530/350

See application file for complete search history.

(56) References Cited

U.S. PATENT DOCUMENTS

| | | | |
|---|---|---|---|
| 5,420,030 | A | 5/1995 | Reitz et al. |
| 5,830,876 | A | 11/1998 | Weiner et al. |
| 6,090,392 | A | 7/2000 | Berman |
| 6,139,843 | A | 10/2000 | Rubinstein et al. |

FOREIGN PATENT DOCUMENTS

| | | | |
|---|---|---|---|
| JP | H06-501851 | | 3/1994 |
| JP | 2000-516445 | | 12/2000 |
| WO | WO 92/22654 | | 12/1992 |
| WO | WO 97/48370 | | 12/1997 |
| WO | WO 0232943 | * | 4/2002 |
| WO | 03/039470 A | | 5/2003 |

OTHER PUBLICATIONS

Barnett, S. et al. "Vaccination with HIV-1 gp120 DNA induces immune responses that are boosted by a recombinant GP120 protein subunit" Vaccine vol. 15(1997): pp. 869-873.*

Gao F. "Genetic variation of HIV type 1 in four world health organization-sponsored vaccine evaluation sites: generation of functional envelope (glycoprotein 160) clones representative of sequence subtypes A, B, C, and E" AIDS Res. And Hum Retroviruses, vol. 10 (1994), No. 11, pp. 1359-1368.*

Gao F. et al. "Molecular cloning and analysis of functional envelope genes from human immunodeficiency virus type 1 sequence subtype A through G" J. Virology vol. 70(1996), No. 3, pp. 1651-1667.*

Andre S. et al. "Increased immune responses elicited by DNA vaccination with a synthetic gp120 sequence with optimized codon usage" J. Virology vol. 72(1998), No. 2, pp. 1497-1503.*

Pontesilli, O. et al. "Phase II controlled trial of post-exposure immunization with recombinant gp 160 versus antiretroviral therapy in asymptomatic HIV-1-infected adults" AIDS vol. 12 (1998), No. 5, pp. 473-480.*

Vandepapelliere p. "Therapeutic vaccination against chronic viral infections" The Lancet Infectious Diseases vol. 2(2002) pp. 353-367.*

Yoshida T. et al. "Activation of HIV-1-specific immune responses to an HIV-1 vaccine constructed from a replication-defective adenovirus vector using various combinations of immunization protocols". Clin Exp Immunol. Jun. 2001;124(3):445-52.*

Gao F. et al. "Codon-Usage Optimization of gag, pol, env and nef Genes of an HIV-1 Subtype C Strain".AIDS Vaccine 2001. Sep. 5-8, 2001; abstract No. 201.*

Evans et al. "QS-21 promotes an adjuvant effect allowing for reduced antigen dose during HIV-1 envelope subunit immunization in humans". Vaccine. Feb. 28, 2001;19(15-16):2080-91.*

Li M, et al. "Human immunodeficiency virus type 1 env clones from acute and early subtype B infections for standardized assessments of vaccine-elicited neutralizing antibodies." J Virol. Aug. 2005;79(16):10108-25.*

Mann AM, et al. "HIV sensitivity to neutralization is determined by target and virus producer cell properties." AIDS.23:1659-1667, 2009.*

Desrosiers RC. "Prospects for an AIDS vaccine" Nature Medicine vol. 10 (2004), pp. 221-223.*

Fenyo EM et al. "International network for comparison of HIV neutralization assays: the NeutNet report." PLoS One. 2009;4(2):e4505.* Haynes "Critical issues in mucosal immunity for HIV-1 vaccine development" (J. Allergy Clin Immunol.122:3-9, 2008).*

Fomsgaard, A, "HIV-1 DNA Vaccines" *Immunology Letters*, vol. 65, No. 1/2, pp. 127-131 (1999).

Pal, et al., "Definitive toxicology and biodistribution study of a polyvalent DNA prime/protein boost human immunodeficiency virus type 1 (HIV-1) vaccine in rabbints" *Vaccine*, vol. 24, No. 8, pp. 1225-1234 (2006).

(Continued)

*Primary Examiner* — Bo Peng

(74) *Attorney, Agent, or Firm* — Fish & Richardson P.C.

(57) ABSTRACT

Polyvalent, primary isolate nucleic acid compositions for inducing an immune response against HIV is disclosed. The composition and methods described herein are for the use of a DNA composition that encodes one or more different HIV envelope glycoproteins. The DNA composition can encode an HIV Gag protein. The DNAs encoding one or more HIV proteins are a combination of different nucleic acids, such as DNA plasmids, generated from primary isolate DNA of different HIV major group genetic clades and/or different proteins. HIV protein compositions for inducing an immune response against HIV are disclosed. Methods fro using the protein compositions as boosts following administration of the DNA compositions are provided.

34 Claims, 56 Drawing Sheets

OTHER PUBLICATIONS
Pal Ranajit, et al., "Polyvalent DNA prime and envelope protein boost HIV-1 vaccine elicits humoral and cellular responses and controls plasma viremia in rhesus macaques following rectal challenge with an R5 SHIV isolate" *Journal of Medical Primatology*, vol. 34, No. 5-6, pp. 226-236 (2005).
Weidle, et al., "HIV/AIDS treatment and HIV vaccines for Africa" *Lancet*, vol. 359, No. 9325, pp. 2261-2267 (2002).
Alonso et al., "Biodegradable microspheres as controlled-release tetanus toxoid delivery systems," Vaccine 12:299-306 (1994).
Bagarazzi et al., "Nucleic acid-based vaccines as an approach to immunization against human immunodeficiency virus type-1," Curr. Top Microbiol. Immunol. 226:107-43 (1998).
Barnett et al., "The ability of an oligomeric human immunodeficiency virus type 1 (HIV-1) envelope antigen to elicit neutralizing antibodies against primary HIV-1 isolates is improved following partial deletion of the second hypervariable region," J. Virol. 75:5526-40 (2001).
Barouch et al., "Eventual AIDS vaccine failure in a rhesus monkey by viral escape from cytotoxic T lymphocytes," Nature 415(6869):335-9 (2002).
Boyer et al., "Protection of chimpanzees from high-dose heterologous HIV-1 challenge by DNA vaccination," Nat. Med. 3(5):526-32 (1997).
Chakrabarti et al., "Modifications of the human immunodeficiency virus envelope glycoprotein enhance immunogenicity for genetic immunization," J. Virol. 76(11):5357-68 (2002).
Chapman, et al., "Effect of intron A from human cytomegalovirus (Towne) immediate-early gene on heterologous expression in mammalian cells," Nucleic Acids Res. 19:3979-3986 (1991).
Clements et al., "Cross-protective immune responses induced in rhesus macaques by immunization with attenuated macrophage-tropic simian immunodeficiency virus," J. Virol. 69: 2737 (1995).
Cristillo et al., "Preclinical evaluation of cellular immune responses elicited by a polyvalent DNA prime/protein boost HIV-1 vaccine," Virology 346(1):151-68 (2006).
Eldridge et al., "Biodegradable microspheres as a vaccine delivery system," Molec. Immunol. 28:287-94 (1991).
Goulder et al., "Evolution and transmission of stable CTL escape mutations in HIV infection," Nature 412:334-338 (2001).
Goulder et al., "Late escape from an immunodominant cytotoxic T-lymphocyte response associated with progression to AIDS," Nature Med. 3:212-217 (1997).
Hu et al., "The immunostimulating complex (ISCOM) is an efficient mucosal delivery system for respiratory syncytial virus (RSV) envelope antigens inducing high local and systemic antibody responses," Clin. Exp. Immunol. 113:235-43 (1998).
Hurwitz et al., "Application of the polyvalent approach to HIV-1 vaccine development," Curr. Drug Targets Infect. Disord. 5(2):143-56 (2005).
Johnston and Flores, "Progress in HIV vaccine development," Curr. Op. In. Pharmac. 1:504-510 (2001).
Jones et al., "Protection of mice from Bordetella pertussis respiratory infection using microencapsulated pertussis fimbriae," Vaccine 13(7):675-81 (1995).
Kensil, et al., "QS-21 and QS-7: purified saponin adjuvants," Dev. Biol. Stand. 92:41-7 (1998).
Kong et al., "Immunogenicity of multiple gene and clade human immunodeficiency virus type 1 DNA vaccines," J. Virol. 77:12764-772 (2003).
Letvin et al., "Immunogenicity of multiple gene and clade human immunodeficiency virus type 1 DNA vaccines," Proc. Natl. Acad. Sci. USA 94(17):9378-83 (1997).
Ljungberg et al., "Enhanced immune responses after DNA vaccination with combined envelope genes from different HIV-1 subtypes," Virology 302(1):44-57 (2002).
Lu et al., "Immunogenicity of DNA vaccines expressing human immunodeficiency virus type 1 envelope glycoprotein with and without deletions in the V1/2 and V3 regions," AIDS Res. Hum. Retroviruses 14(2):151-5 (1998).
Lu et al., "Simian immunodeficiency virus DNA vaccine trial in macaques," J. Virol. 70(6):3978-991 (1996).
MacGregor et al., "First human trial of a DNA-based vaccine for treatment of human immunodeficiency virus type 1 infection: safety and host response," J. Infect. Dis. 178(1):92-100 (1998).
Mascola et al., "Immunization with envelope subunit vaccine products elicits neutralizing antibodies against laboratory-adapted but not primary isolates of human immunodeficiency virus type 1. The National Institute of Allergy and Infectious Diseases AIDS Vaccine Evaluation Group," J. Infect. Dis. 173:340-348 (1996).
Mascola, et al., "Human immunodeficiency virus type 1 neutralization measured by flow cytometric quantitation of single-round infection of primary human T cells," J. Virol. 76(10):4810-21 (2002).
McMichael and Hanke, "The quest for an AIDS vaccine: is the CD8+ T-cell approach feasible?" Nat. Rev. Immunol. 2(4):283-91 (2002).
Montefiori et al., "Evaluation of antiviral drugs and neutralizing antibodies to human immunodeficiency virus by a rapid and sensitive microtiter infection assay," J. Clin. Microbiol., 26:231-237 (1988).
Pal et al., "Immunization of rhesus macaques with a polyvalent DNA prime/protein boost human immunodeficiency virus type 1 vaccine elicits protective antibody response against simian human immunodeficiency virus of R5 phenotype," Virology (Feb. 2, 2006).
Qiu, et al., "Enhancement of primary and secondary cellular immune responses against human immunodeficiency virus type 1 gag by using DNA expression vectors that target Gag antigen to the secretory pathway," J. Virology. 74(13):5997-6005 (2000).
Rencher and Hurwitz, "Effect of natural HIV-1 envelope V1-V2 sequence diversity on the binding of V3-specific and non-V3-specific antibodies," J. Acquir. Immune Defic. Syndr. Hum. Retrovirol. 16(2):69-73 (1997).
Rencher et al., "Does the key to a successful HIV type 1 vaccine lie among the envelope sequences of infected individuals?" AIDS Res. Hum. Retroviruses 11(9):1131-3 (1995).
Richmond et al., "Screening of HIV-1 Env glycoproteins for the ability to raise neutralizing antibody using DNA immunization and recombinant vaccinia virus boosting," Virology 230(2):265-74 (1997).
Robinson, "DNA vaccines for immunodeficiency viruses," AIDS 11(Suppl A):S109-19 (1997).
Stambas et al., "Long lived multi-isotype anti-HIV antibody responses following a prime-double boost immunization strategy," Vaccine 23(19):2454-64 (2005).
Takahashi et al., "Induction of CD8+ cytotoxic T cells by immunization with purified HIV-1 envelope protein in ISCOMs," Nature 344:873-75 (1990).
Vitiello et al., "Development of a lipopeptide-based therapeutic vaccine to treat chronic HBV infection. I. Induction of a primary cytotoxic T lymphocyte response in humans," J. Clin. Invest. 95:341-49 (1995).
Wang et al., "Polyvalent HIV-1 Env vaccine formulations delivered by the DNA priming plus protein boosting approach are effective in generating neutralizing antibodies against primary human immunodeficiency virus type 1 isolates from subtypes A, B, C, D and E," Virology (Apr. 6, 2006).
Weber et al., "Neutralization serotypes of human immunodeficiency virus type 1 field isolates are not predicted by genetic subtype. The WHO Network for HIV Isolation and Characterization," Virol. 70: 7827-832 (1996).
Zhan et al., "Minor components of a multi-envelope HIV vaccine are recognized by type-specific T-helper cells," Vaccine 22(9-10):1206-13 (2004).
Zolla-Pazner et al., "Immunotyping of human immunodeficiency virus type 1 (HIV): an approach to immunologic classification of HIV," J. Virol. 73: 4042-51 (1999).
HIV Vaccine Development Status Report, May 2000, http://niaid.gov/daids/vaccine/whsummarystatus.htm.
Nyambi et al., "Immunoreactivity of Intact Virions of Human Immunodeficiency Virus Type 1 (HIV-1) Reveals the Existence of Fewer HIV-1 Immunotypes than Genotypes," J. Virol. 74:10670-680 (2000).

International Search Report in PCT/US03/38640 mailed Feb. 3, 2005.
McElrath et al., "HIV-Infected Macrophages as Efficient Stimulator Cells for Detection of Cytotoxic T Cell Responses to HIV in Seronegative and Seropositive Vaccine Recipients," *AIDS Research and Human Retroviruses*, 1994, vol. 10, No. 5, pp. 541-549.
Rodenburg et al., "Near Full-Length Clones and Reference Sequences for Subtype C Isolates of HIV Type 1 from Three Different Continents," *AIDS Research and Human Retroviruses*, 2001, vol. 17, No. 2, pp. 161-168.

* cited by examiner

| Study groups | Rabbit no. | DNA priming (4 X) | | Protein boost (2 X) | |
|---|---|---|---|---|---|
| | | gp120 immunogens | Doses (mg) | gp120 immunogens | Doses (mg) |
| Mono-valent | R101, R102, R103 | Bal | 36 | Bal | 100 |
| | R104, R105 | B | 36 | B | 100 |
| | R106, R107, R108 | C1 | 36 | C1 | 100 |
| | R109, R110, R111 | E | 36 | E | 100 |
| 3-valent | R301, R302, R303 | B, C1, E | 36 (12 μg each DNA) | B, C1, E | 100 (33.3 μg each protein) |
| 8-valent | R801, R802, R803 | A, B, C1, D, E, F, G, Bal | 40 (5 μg each DNA) | B, C1, E, Bal | 100 (25 μg each protein) |
| Control | R001, R002 | None (Vector control) | 36 | B, C1, E, Bal | 100 (25 μg each protein) |

Neutralization against HIV-1 primary isolates from clades A, B, C and E after last DNA immunization

| Study groups | Animal no. | Clade B | | | | Clade C | | | Clade A | Clade E | |
|---|---|---|---|---|---|---|---|---|---|---|---|
| | | ADA | SF162 | Bal | JRCSF | TV1 | DU151 | S007 | DJ263 | CM235 | CM244 |
| Mono-valent | R101 | 0.0 | 34.2 | 10.9 | 21.2 | 0.0 | 0.0 | 40.0 | 0.0 | 0.0 | 0.0 |
| | R102 | 0.0 | 37.9 | 11.3 | 12.1 | 0.0 | 6.0 | 0.0 | 0.0 | 0.0 | 0.0 |
| | R104 | 16.0 | 76.0 | 15.0 | 34.0 | 43.6 | 0.0 | 13.8 | 44.9 | 0.0 | 0.0 |
| | R105 | 4.0 | 55.0 | 15.0 | 46.0 | 27.1 | 8.2 | 0.0 | 4.0 | 0.0 | 0.0 |
| | R106 | 16.9 | 59.6 | 4.0 | 30.0 | 31.6 | 17.6 | 11.3 | 39.0 | 0.0 | 2.4 |
| | R107 | 1.8 | 47.9 | 5.8 | 21.5 | 22.5 | 0.0 | 0.6 | 21.3 | 0.0 | 2.4 |
| | R109 | 0.0 | 38.6 | 0.0 | 18.9 | 14.2 | 33.8 | 0.0 | 32.0 | 0.0 | 29.9 |
| | R110 | 8.9 | 46.6 | 0.0 | 0.0 | 16.9 | 0.0 | 21.1 | 12.2 | 0.0 | 19.7 |
| Poly-valent | R301 | 0.0 | 71.8 | 17.9 | 45.6 | 0.0 | 0.0 | 0.0 | 0.0 | 0.0 | 0.0 |
| | R302 | 0.0 | 42.1 | 0.0 | 16.3 | 14.0 | 0.0 | 39.0 | 0.0 | 0.0 | 0.0 |
| | R801 | 0.0 | 63.5 | 5.2 | 40.7 | 26.0 | 1.0 | 0.0 | 3.0 | 0.0 | 0.0 |
| | R802 | 0.0 | 34.8 | 0.0 | 0.0 | 31.0 | 0.0 | 10.0 | 28.0 | 0.0 | 0.0 |
| Control | R001 | 0.0 | 0.0 | 0.0 | 0.0 | 0.0 | 0.0 | 4.0 | 0.0 | 0.0 | 6.0 |
| Positive antibodies | Concentration | | | | | | | | | | |
| HIVIG | 10 mg/ml | 96.8 | 99.1 | 98.9 | 98.8 | 98.1 | 96.4 | 100.1 | 98.4 | 95.3 | 98.1 |
| | 1 mg/ml | 44.6 | 95.6 | 84.1 | 83.1 | 19.0 | 58.6 | 69.9 | 75.0 | 29.3 | 35.2 |
| 2F5 | 50 μg/ml | 74.9 | 92.9 | 86.7 | 93.2 | 76.5 | 29.0 | 39.2 | 27.9 | 91.2 | 86.4 |
| | 5 μg/ml | 43.4 | 67.8 | 52.6 | 76.4 | 29.0 | 16.6 | 17.5 | 10.8 | 65.2 | 61.4 |
| 2G12 | 50 μg/ml | 32.7 | 59.2 | 75.9 | 77.9 | 28.2 | 5.5 | 2.3 | 90.1 | 4.7 | 0.0 |
| | 5 μg/ml | 20.3 | 43.6 | 53.3 | 57.9 | 15.7 | 16.0 | 9.0 | 77.0 | 0.0 | 6.0 |

FIG. 2

Neutralization against HIV-1 primary isolates from clades A, B, C and E after the first protein boost

| Study groups | Animal no. | Clade B | | | | Clade C | | | Clade A | Clade E | |
|---|---|---|---|---|---|---|---|---|---|---|---|
| | | ADA | SF162 | Bal | JRCSF | TV1 | DU151 | S007 | DJ263 | CM235 | CM244 |
| Mono-valent | R101 | 0.0 | 80.4 | 58.9 | 70.4 | 21.0 | 0.0 | 47.0 | 24.0 | 0.0 | 0.0 |
| | R102 | 0.0 | 74.6 | 63.9 | 57.0 | 14.0 | 0.0 | 0.0 | 0.0 | 0.0 | 0.0 |
| | R104 | 31.5 | 95.0 | 81.0 | 69.0 | 59.7 | 0.0 | 5.4 | 57.7 | 0.0 | 0.0 |
| | R105 | 6.0 | 46.5 | 88.0 | 84.0 | 81.2 | 0.0 | 0.0 | 41.5 | 0.0 | 0.0 |
| | R106 | 10.8 | 47.4 | 31.1 | 30.0 | 20.4 | 15.4 | 27.5 | 42.7 | 0.0 | 0.0 |
| | R107 | 2.7 | 54.0 | 0.0 | 6.2 | 39.5 | 0.0 | 7.0 | 16.7 | 0.0 | 26.2 |
| | R109 | 13.0 | 35.1 | 0.0 | 19.7 | 40.3 | 1.3 | 0.0 | 44.4 | 0.0 | 8.5 |
| | R110 | 10.5 | 31.9 | 0.0 | 0.0 | 34.8 | 4.9 | 34.3 | 36.5 | 0.0 | 28.4 |
| Poly-valent | R301 | 11.5 | 93.6 | 93.6 | 90.5 | 89.0 | 23.0 | 0.0 | 14.0 | 0.0 | 0.0 |
| | R302 | 0.0 | 91.5 | 79.6 | 84.2 | 87.0 | 33.0 | 54.0 | 55.0 | 0.0 | 27.0 |
| | R801 | 0.0 | 84.8 | 61.6 | 73.9 | 68.0 | 23.0 | 31.0 | 36.0 | 0.0 | 0.0 |
| | R802 | 0.0 | 73.0 | 13.5 | 41.4 | 74.0 | 0.0 | 13.0 | 65.0 | 0.0 | 0.0 |
| Control | R001 | 0.0 | 33.5 | 0.2 | 24.1 | 0.0 | 0.0 | 36.0 | 0.0 | 0.0 | 6.0 |
| Positive antibodies | Concentration | | | | | | | | | | |
| HIVIG | 10 mg/ml | 96.8 | 99.1 | 98.9 | 98.8 | 98.1 | 96.4 | 100.1 | 98.4 | 95.3 | 98.1 |
| | 1 mg/ml | 44.6 | 95.6 | 84.1 | 83.1 | 19 | 58.6 | 69.9 | 75 | 29.3 | 35.2 |
| 2F5 | 50 µg/ml | 74.9 | 92.9 | 86.7 | 93.2 | 76.5 | 29 | 39.2 | 27.9 | 91.2 | 86.4 |
| | 5 µg/ml | 43.4 | 67.8 | 52.6 | 76.4 | 29 | 16.6 | 17.5 | 10.8 | 65.2 | 61.4 |
| 2G12 | 50 µg/ml | 32.7 | 59.2 | 75.9 | 77.9 | 28.2 | 5.5 | 2.3 | 90.1 | 4.7 | 0 |
| | 5 µg/ml | 20.3 | 43.6 | 53.3 | 57.9 | 15.7 | 16 | 9 | 77 | 0 | 6 |

FIG. 3

Neutralization against HIV-1 primary isolates from clades A, B, C and E after the second protein boost

| Study groups | Animal no. | Clade B ADA | Clade B SF162 | Clade B Bal | Clade B JRCSF | Clade C TV1 | Clade C DU151 | Clade C S007 | Clade A DJ263 | Clade E CM235 | Clade E CM244 |
|---|---|---|---|---|---|---|---|---|---|---|---|
| Mono-valent | R101 | 0.0 | 89.5 | 70.0 | 67.9 | 0.0 | 0.0 | 0.0 | 22.0 | 0.0 | 27.7 |
| | R102 | 1.0 | 77.3 | 56.0 | 49.4 | 52.8 | 0.0 | 0.0 | 56.4 | 0.0 | 17.0 |
| | R104 | 33.5 | 94.0 | 87.0 | 79.0 | 80.0 | 22.8 | 33.0 | 65.7 | 0.0 | 0.0 |
| | R105 | 37.0 | 92.0 | 84.0 | 84.0 | 81.9 | 34.9 | 0.0 | 49.5 | 0.0 | 0.0 |
| | R106 | 35.1 | 92.6 | 82.1 | 80.7 | 79.9 | 54.1 | 62.5 | 79.8 | 25.5 | 33.4 |
| | R107 | 26.1 | 92.1 | 76.6 | 82.3 | 90.0 | 0.0 | 66.8 | 68.5 | 0.0 | 45.3 |
| | R109 | 37.2 | 88.9 | 44.9 | 48.5 | 76.8 | 0.0 | 3.4 | 68.2 | 0.0 | 0.0 |
| | R110 | 11.3 | 26.3 | 0.0 | 52.6 | 77.6 | 43.7 | 59.1 | 70.0 | 0.0 | 28.4 |
| Poly-valent | R301 | 24.0 | 94.7 | 81.2 | 82.6 | 79.2 | 8.7 | 39.0 | 70.2 | 10.9 | 33.4 |
| | R302 | 13.0 | 93.2 | 75.2 | 67.1 | 47.3 | 0.0 | 44.0 | 64.0 | 16.1 | 23.7 |
| | R801 | 24.0 | 91.4 | 74.9 | 79.7 | 72.9 | 0.0 | 42.4 | 62.5 | 3.3 | 32.5 |
| | R802 | 29.0 | 89.3 | 69.5 | 73.8 | 83.8 | 1.2 | 3.7 | 79.7 | 15.2 | 37.6 |
| Control | R001 | 0.0 | 40.6 | 23.7 | 35.4 | 50.1 | 0.0 | 0.0 | 22.0 | 0.0 | 0.0 |
| Positive antibodies | Concentration | | | | | | | | | | |
| HIVIG | 10 mg/ml | 96.8 | 99.1 | 98.9 | 98.8 | 98.1 | 96.4 | 100.1 | 98.4 | 95.3 | 98.1 |
| | 1 mg/ml | 44.6 | 95.6 | 84.1 | 83.1 | 19.0 | 58.6 | 69.9 | 75.0 | 29.3 | 35.2 |
| 2F5 | 50 μg/ml | 74.9 | 92.9 | 86.7 | 93.2 | 76.5 | 29.0 | 39.2 | 27.9 | 91.2 | 86.4 |
| | 5 μg/ml | 43.4 | 67.8 | 52.6 | 76.4 | 29.0 | 16.6 | 17.5 | 10.8 | 65.2 | 61.4 |
| 2G12 | 50 μg/ml | 32.7 | 59.2 | 75.9 | 77.9 | 28.2 | 5.5 | 2.3 | 90.1 | 4.7 | 0.0 |
| | 5 μg/ml | 20.3 | 43.6 | 53.3 | 57.9 | 15.7 | 16.0 | 9.0 | 77.0 | 0.0 | 6.0 |

FIG. 4

Neutralization against TV1 (clade C)

| Legend |
|---|
| ▉ Prebleed |
| ▨ Post last DNA |
| ■ Protein 1 |
| ☐ Protein 2 |

Rabbit groups:
- C4-1 / C4-2: 3-Valent (B, C, E)
- C7-1 / C7-2: 8-Valent (A, B, C, D, E, F, G, Bal)
- C10-1: 8-Valent (protein only)

Anti-gp120 response in rabbits immunized intramuscularly with DP6-001

Anti-gp120 response in rabbits immunized intradermally with DP6-001

Anti-gag response in rabbits immunized intramuscularly with DP6-001

Antibody titers in macaques immunized with polyvalent DNA and gp120 protein

Antibody titers in macaques immunized with polyvalent DNA and gp120 protein

Antibody titers in macaques immunized with polyvalent DNA and gp120 protein

Gag peptide pools

Gag peptide pools

Gag peptide pools

Gag peptide pools

Gag peptide pools

Gag peptide pools

Wild type Gag.Czm DNA sequence:

ATGGGTGCGAGAGCGTCAATATTAAGAGGGGGAAAATTAGATAAATGGGAAAAAATTAGGCTAAGGCCAGGGGGAAAGA
AACGCTATATGATAAAACACCTAGTATGGGCAAGCAGGGAGCTGGAAAGATTTGCGCTTAACCCTGGCCTTTTAGAAACAT
CAGAAGGCTGTAAACAAATAATGAAACAGCTACAACCAGCTCTTCAGACAGGAACGGAGGAACTTAGATCATTATACAACA
CAGTAGCAACTCTCTATTGTGTACATGAAGGGGTAGAGGTACGAGACACCAAGGAAGCCTTAGACAGGATAGAGGAAGAA
CAAAACAAAATTCAGCAAAAAATACAGCAAAAAACACAGCAAGCGGCTGACGGAAAGGTCAGTCAAAATTATCCTATAGT
GCAGAATCTCCAAGGGCAAATGGTACACCAGAAACTATCACCTAGAACTTTGAATGCATGGGTAAAAGTAATAGAAGAAA
AAGCTTTTAGCCCAGAGGTAATACCCATGTTTACAGCATTATCAGAAGGAGCCACCCCACAAGATTTAAACACCATGTTAAA
TACAGTGGGGGGACATCAAGCAGCCATGCAAATGTTAAAAGATACTATCAATGAGGAGGCTGCAGAATGGGATAGATTAC
ATCCAGTGCATGCAGGGCCTATTGCACCAGGCCAAATGAGAGAACCAAGGGGAAGTGATATAGCAGGAACTACTAGTACCC
TCCAAGAACAGATAGCATGGATGACAAGTAATCCCCCTATTCCAGTGGGAGACATCTATAAAAGATGGATAATTCTGGGGT
TAAATAAAATAGTAAGAATGTATAGCCCTGTCAGCATTTTGGACATAAAACAAGGGCCAAAGGAACCCTTTAGAGACTATG
TAGACCGGTTCTTCAAAACTTTAAGAGCTGAACAGGCTACACAAGAAGTAAAAAATTGGATGACAGACACCTTGTTGGTCC
AAAATGCAAACCCAGATTGCAAGACCATTTTAAAAGCATTAGGACCAGGGGCTACATTAGAAGAAATGATGACAGCATGTC
AAGGAGTGGGAGGACCTAGCCACAAAGCAAGAGTGTTGGCTGAGGCAATGAGCCAAACAAATAGTGTAAACATACTGATG
CAGAAAAGCAATTTTAAAGGAAATAAAAGAATGGTTAAATGTTTTAACTGTGGTAAGGAAGGGCACATAGCCAGAAATTGC
AGGGCCCCTAGGAAAAAGGGCTGTTGGAAATGTGGAAAGGAGGGACACCAAATGAAAGACTGTACTGAGAGGCAGGCTAA
TTTTTTAGGGAAAATTTGGCCTTCCCACAAGGGAAGGCCAGGGAATTTCCTTCAGAACAGGCCAGAGCCAACAGCCCCACC
AGCAGAGAGCTTCAGGTTCGAGGAGACAACCCCCGCTCCGAAGCAGGAGTCGAAAGACAGGGAAGCCTTAACTTCCCTCAA
ATCACTCTTTGGCAGCGACCCCTTGTCTCAATAA (SEQ ID NO:5)

FIG. 27

Codon optimized Gag.Czm DNA sequence:

ATGGGAGCCAGAGCCAGCATCCTGAGAGGAGGCAAACTGGACAAGTGGGAGAAGATTAGACTGCGG
CCTGGAGGCAAGAAACGGTACATGATCAAGCACCTGGTGTGGGCCAGCAGAGAGCTGGAGCGGTTCG
CACTGAATCCTGGCCTCCTGGAGACCAGCGAAGGATGCAAACAGATCATGAAGCAGCTCCAACCAGC
TCTGCAGACCGGCACTGAGGAACTGAGAAGCCTGTACAACACCGTGGCCACCCTGTACTGCGTGCAC
GAGGGCGTGGAAGTGCGGGACACCAAGGAGGCCCTGGACCGGATCGAGGAAGAGCAGAACAAGATC
CAGCAAAAGATCCAGCAGAAGACCCAACAGGCCGCTGATGGAAAGGTGAGCCAGAACTACCCCATC
GTCCAGAACCTCCAGGGCCAGATGGTGCACCAGAAGCTGAGCCCTCGGACACTGAACGCCTGGGTCA
AGGTGATCGAAGAGAAGGCCTTCAGCCCTGAAGTGATCCCCATGTTCACAGCTCTGAGCGAAGGCGC
CACTCCTCAGGACCTGAACACCATGCTGAACACCGTGGGAGGCCACCAAGCTGCAATGCAGATGCTG
AAGGACACCATCAACGAGGAAGCTGCCGAGTGGGACAGACTGCATCCAGTCCACGCCGGACCCATCG
CTCCTGGCCAGATGCGGGAACCTAGAGGAAGCGATATCGCTGGCACTACCTCCACCCTGCAAGAGCA
GATCGCTTGGATGACCAGCAACCCCCCTATCCCCGTCGGCGACATCTACAAGCGGTGGATCATCCTGG
GCCTGAACAAGATCGTGAGAATGTACAGCCCCGTGAGCATCCTGGACATCAAGCAAGGACCTAAGGA
GCCCTTCAGAGACTACGTCGACCGGTTCTTTAAGACTCTGAGAGCCGAGCAGGCAACCCAGGAGGTG
AAGAACTGGATGACCGACACACTGCTGGTCCAGAACGCCAACCCCGACTGCAAGACCATCCTGAAGG
CTCTGGGACCCGGCGCCACACTGGAAGAGATGATGACAGCATGCCAGGGCGTCGGAGGACCAAGCCA
CAAAGCAAGAGTGCTCGCCGAGGCCATGAGCCAGACCAACAGCGTGAATATCCTGATGCAGAAGAGC
AACTTCAAAGGCAACAAGCGGATGGTCAAGTGCTTCAACTGTGGCAAGGAAGGACACATCGCACGGA
ACTGCAGAGCTCCACGGAAGAAAGGCTGCTGGAAGTGCGGCAAGGAAGGACACCAGATGAAGGACT
GCACAGAGCGGCAAGCAAACTTCCTCGGAAAGATCTGGCCAAGCCACAAGGGAAGACCCGGCAATTT
CCTGCAGAACAGACCTGAGCCCACCGCCCCACCTGCTGAGAGCTTCCGGTTCGAAGAGACCACACCC
GCCCCCAAGCAGGAGAGCAAGGACAGAGAAGCACTGACCAGCCTGAAGAGCCTGTTCGGCAGCGAT
CCCCTGAGCCAGTGA (SEQ ID NO:6)

FIG. 28

Wild type gp120.Bal DNA sequence:

TTGTGGGTCACAGTCTATTATGGGGTACCTGTGTGGAAAGAAGCAACCACCACTCTATTTTGTGCATCAGATGCTA
AAGCATATGATACAGAGGTACATAATGTTTGGGCCACACATGCCTGTGTACCCACAGACCCCAACCCACAAGAAG
TAGAATTGGAAAATGTGACAGAAAATTTTAACATGTGGAAAAATAACATGGTAGAACAGATGCATGAGGATATA
ATCAGTTTATGGGATCAAAGCCTAAAGCCATGTGTAAAATTAACTCCACTCTGTGTTACTTTAAATTGCACTGATTT
GAGGAATGCTACTAATGGGAATGACACTAATACCACTAGTAGTAGCAGGGAAATGATGGGGGGAGGAGAAATGA
AAAATTGCTCTTTCAAAATCACCACAAACATAAGAGGTAAGGTGCAGAAAGAATATGCACTTTTTTATGAACTTG
ATATAGTACCAATAGATAATAATAGTAATAATAGATATAGGTTGATAAGTTGTAACACCTCAGTCATTACACAGG
CCTGTCCAAAGATATCCTTTGAGCCAATTCCCATACATTATTGTGCCCCGGCTGGTTTTGCGATTCTAAAGTGTAAA
GATAAGAAGTTCAATGGAAAAGGACCATGTTCAAATGTCAGCACAGTACAATGTACACATGGGATTAGGCCAGTA
GTATCAACTCAACTGCTGTTAAATGGCAGTCTAGCAGAAGAAGAGGTAGTAATTAGATCCGAAAATTTCGCGGAC
AATGCTAAAACCATAATAGTACAGCTGAATGAATCTGTAGAAATTAATTGTACAAGACCCAACAACAATACAAGA
AAAAGTATACATATAGGACCAGGCAGAGCATTATATACAACAGGAGAAATAATAGGAGATATAAGACAAGCACA
TTGTAACCTTAGTAGAGCAAAATGGAATGACACTTTAAATAAGATAGTTATAAAATTAAGAGAACAATTTGGGAA
TAAAACAATAGTCTTTAAGCATTCCTCAGGAGGGGACCCAGAAATTGTGACGCACAGTTTTAATTGTGGAGGGGA
ATTTTTCTACTGTAATTCAACACAACTGTTTAATAGTACTTGGAATGTTACTGAAGAGTCAAATAACACTGTAGAA
AATAACACAATCACACTCCCATGCAGAATAAAACAAATTATAAACATGTGGCAGAAAGTAGGAAGAGCAATGTA
TGCCCCTCCCATCAGAGGACAAATTAGATGTTCATCAAATATTACAGGGCTGCTATTAACAAGAGATGGTGGTCCA
GAGGCAAACAAGACCGAGGTCTTCAGACCTGGAGGAGGAGATATGAGGGACAATTGGAGAAGTGAATTATATAA
ATATAAAGTAGTAAAAATTGAACCATTAGGAGTAGCACCCACCAAGGCAAAGAGAAGAGTGGTGGAGTAA (SEQ
ID NO:7)

FIG. 29

Codon optimized gp120.Bal DNA sequence:

CTGTGGGTGACCGTGTACTACGGCGTGCCCGTGTGGAAGGAGGCCACCACCACCCTGTTCTGCGCCAGCGACCGCAAGGCCTACGA
CACCGAGGTGCACAACGTGTGGGCCACCCACGCCTGCGTGCCCACCGACCCCAACCCCCAGGAGGTGGAGCTGAAGAACGTGACC
GAGAACTTCAACATGTGGAAGAACAACATGGTGGAGCAGATGCACGAGGACATCATCAGCCTGTGGGACCAGAGCCTGAAGCCCT
GCGTGAAGCTGACCCCCCTGTGCGTGACCCTGAACTGCACCGACCTGCGCAACGCCACCAACGGCAACGACACCAACACCACTAGT
AGCAGCCGCGGCATGGTGGGCGGCGGCGAGATGAAGAACTGCAGCTTCAACATCACCACCAACATCCGCGGCAAGGTGCAGAAGG
AGTACGCCCTGTTCTACAAGCTGGACATCGCCCCCATCGACAACAACAGCAACAACCGCTACCGCCTGATCAGCTGCAACACCAGC
GTGATCACCCAGGCCTGCCCCAAGGTGAGCTTCGAGCCCATCCCCATCCACTACTGCGCCCCCGCCGGCTTCGCCATCCTGAAGTGC
AAGGACAAGAAGTTCAACGGCAAGGGCCCCTGCACCAACGTGAGCACCGTGCAGTGCACCCACGGCATCCGCCCCGTGGTGAGCA
CCCAGCTGCTGCTGAACGGCAGCCTGGCCGAGGAGGAGGTGGTGATCCGCAGCGCCAACTTCGCCGACAACGCCAAGGTGATCAT
CGTGCAGCTGAACGAGAGCGTGGAGATCAACTGCACCCGCCCCAACAACAACACCCGCAAGTCCATCCACATCGGCCCCGGCCGC
GCCTTCTACACCACCGGCGAGATCATCGGCGACATCCGCCAGGCCCACTGCAACCTGAGCCGCGCCAAGTGGAACGACACCCTGAA
CAAGATCGTGATCAAGCTGCGCGAGCAGTTCGGCAACAAGACCATCGTGTTCAAGCACAGCAGCGGCGGCGACCCCGAGATCGTG
ACCCACAGCTTCAATTGCGGCGGCGAGTTCTTCTACTGCAACAGCACCCAGCTGTTCAACAGCACCTGGAACGTGACCGAGGAGAG
CAACAACACCGTGGAGAACAACACCATCACCCTGCCCTGCCGCATCAAGCAGATCATCAACATGTGGCAGGAGGTGGGCCGCGCC
ATGTACGCCCCCCCCATCCGCGGCCAGATCCGCTGCAGTTCGAACATCACCGGCCTGCTGCTGACCCGCGACGGCGGCCCCGAGGA
CAACAAGACCGAGGTGTTCCGCCCCGGCGGCGGCGACATGCGCGACAACTGGCGCAGCGAGCTGTACAAGTACAAGGTGGTGAAG
ATCGAGCCCCTGGGCGTGGCCCCCACCAAGGCCAAGCGCCGCGTGGTGGAGTAA (SEQ ID NO:8)

FIG. 30

Wild type gp120.B DNA sequence:

TTGTGGGTCACAGTCTATTATGGGGTACCTGTGTGGAAAGAAGCAAACACCACTCTATTTTGTGCATCAGATGC
TAAAGCATATGATACAGAGGTACATAATGTTTGGGCCACACATGCCTGTGTACCCACAGACCCCGATCCACAAG
AAGTAGAATTGGAAAATGTGACAGAAAATTTTAACATGTGGAAAAATAACATGGTAGAACAGATGCATGAGG
ATATAATTAGTTTATGGGATCAAAGCCTAAAGCCATGTGTAAAATTAACCCCACTCTGTGTTACTCTAAATTGC
ACCAATCTGAGGAATGATACTAATACCACGAGGAATGCTACTAATACCACGAGTAGTGAGACAATGATGGAGG
AGGGAGAAATAAAAAATTGCTCTTTCAATATCACCACAAGCATAAGAGATAAGGTGCAAAAAGAATTTGCACT
TTTTTATAAACTTGATGTAGTACCAATAGAAAATGATACTACTAGCTATAGGTTGATAAGTTGTAATACCTCAG
TCCTTACACAGGCCTGCCCAAAGGTATCCTTTGAGCCAATTCCCATACATTTTTGTGCCCCGGCTGGTTTTGCAA
TTCTAAAGTGTAAAGATAAGAAGTTCAATGGAACAGGACCATGTACAAATGTCAGCACAGTACAATGCACACA
TGGAATTAAGCCAGTAGTATCAACTCAACTGCTGTTAAATGGCAGTCTAGCAGAAGAAGAGGTAGTAATTAGG
TCCGCCAATCTCTCGGACAATGCTAAAACCATAATAGTACAGCTGAATGAATCTGTACAAATGAATTGTACGAG
ACCCAACAACAATACAAGAAAAAGTATACATATAGGACCAGGCAGAGCATTTTATACAACAGGAGAAATAAT
AGGAGATATAAGACAAGCACATTGTAACCTTAGTAGAACAAAATGGAATGAAACTTTAAAAAGGATAGTTATA
AAATTAAGAGAGCAATATGAGAATAAAACAATAGTCTTTAATCAATCCTCAGGAGGGGACCCAGAAATTGTAA
TGCTCAGCTTTAATTGTGGAGGGGAATTTTTCTACTGTAATTCAACAAAACTGTTTAATAGTACTTGGAATGGTA
CTGAGTCAAATAACACAGGAGATGACCCAATCGTACTCCCATGCAGAATAAAACAAGTTATAAACATGTGGCA
AGAAGTAGGAAAAGCAATGTATGCCCCTCCCATCAGAGGACAAATTAGATGCTCATCAAATATTACAGGACTG
CTATTAACAAGAGATGGTGGTAACAGTAACGAGACCAATACCACCGAGATCTTCAGACCTGGGGGAGGAAATA
TGAAGGACAATTGGAGAAGTGAATTATATAAATATAAAGTAGTAAGAATTGAACCATTAGGAATAGCACCCAC
CAGGGCAAAGAGAAGAGTGGTGGAGTAA (SEQ ID NO:9)

FIG. 31

Codon optimized gp120.B DNA sequence:

CTGTGGGTGACCGTCTACTATGGGGTGCCTGTGTGGAAGGAGGCCAACACCACTCTGTTCTGCGCTTCTGACGCTAAGGCCTACGAT
ACCGAGGTGCACAATGTGTGGGCCACCCACGCCTGTGTGCCCACCGACCCCGACCCTCAGGAGGTGGAGCTGGAGAACGTGACCGA
AAACTTCAACATGTGGAAGAATAACATGGTGGAGCAGATGCATGAGGATATCATTAGCCTGTGGGACCAGAGCCTAAAGCCCTGCG
TGAAGCTGACCCCCCTGTGTGTGACTCTGAACTGCACCAACCTGAGGAATGATACTAACACCACCAGGAACGCCACTAATACGACCA
GCAGCGAGACCATGATGGAGGAGGGCGAGATCAAGAACTGCTCTTTCAACATCACCACGAGCATCAGAGACAAGGTGCAGAAGGA
GTTTGCCCTTTTCTATAAACTTGATGTGGTGCCTATCGAGAATGACACTACTAGCTACAGGCTGATCAGCTGCAACACCAGCGTCCTG
ACACAGGCCTGCCCCAAGGTGTCCTTCGAGCCAATTCCCATCCACTTTTGTGCCCCGGCTGGTTTCGCCATTCTAAAGTGCAAGGATA
AGAAGTTCAACGGCACCGGTCCTTGTACCAATGTCAGCACCGTACAATGCACCCACGGCATTAAGCCCGTGGTGAGCACTCAGCTGC
TGCTGAACGGCAGCCTGGCCGAGGAAGAGGTGGTGATTCGCTCCGCCAACCTCTCTGACAATGCTAAGACCATAATCGTGCAGCTGA
ACGAGTCTGTGCAGATGAACTGCACGAGGCCCAACAACAATACCAGGAAGAGTATCCATATCGGTCCCGGCAGGGCATTCTATACC
ACCGGCGAGATCATCGGCGACATCAGGCAGGCCCACTGTAACCTTAGCAGGACAAAGTGGAACGAGACTCTGAAGAGGATCGTGAT
CAAGCTGAGGGAGCAGTACGAGAACAAGACCATCGTCTTTAATCAATCCAGCGGCGGGGACCCTGAGATTGTGATGCTGAGCTTCA
ACTGCGGTGGGGAGTTCTTCTACTGTAACTCAACCAAGCTGTTTAATAGCACTTGGAACGGCACTGAGTCTAACAACACCGGTGATG
ACCCCATCGTGCTGCCATGCAGGATCAAGCAGGTGATCAACATGTGGCAGGAAGTGGGCAAGGCCATGTATGCCCCTCCCATCAGG
GGTCAGATTAGGTGCAGCAGCAATATTACCGGCCTGCTACTGACCCGCGACGGCGGTAACAGCAACGAGACCAACACCACCGAGAT
CTTCAGGCCTGGGGGCGGCAACATGAAGGACAATTGGAGGAGCGAGTTATACAAATATAAGGTGGTGAGGATTGAGCCTCTGGGTA
TCGCCCCCACCAGGGCCAAGAGGAGGGTGGTGCAGTAA (SEQ ID NO:10)

FIG. 32

Wild type gp120.Czm DNA sequence:

TTGTGGGTCACAGTCTATTATGGGGTACCTGTGTGGAAAGAAGCAAAAACTACTCTATTCTGTGCATCAGATGCTA
AATCATATGAGAAAGAAGTGCATAATGTCTGGGCTACACATGCCTGTGTACCCACAGACCCCAACCCACAAGAAA
TAGTTTTGGGAAATGTAACAGAAAATTTTAACATGTGGAAAAATGACATGGTGGATCAGATGCATGAGGATATAA
TCAGTTTATGGGATCAAAGCCTAAAGCCATGTGTAAAGTTGACCCCACTCTGTGTCACTTTAAATTGTACAGAGGT
TAATGTTACCAGAAATGTTAATAATAGCGTGGTTAATAATACCACAAATGTTAATAATAGCATGAATGGAGACAT
GAAAAATTGCTCTTTCAACATAACCACAGAACTAAAAGATAAGAAAAAGAATGTGTATGCACTTTTTTATAAACTT
GATATAGTATCACTTAATGAGACTGACGACTCTGAGACTGGCAACTCTAGTAAATATTATAGATTAATAAATTGTA
ATACCTCAGCCCTAACACAAGCCTGTCCAAAGGTCTCTTTTGACCCAATTCCTATACATTATTGTGCTCCAGCTGGT
TATGCGATTCTAAAGTGTAATAATAAGACATTCAATGGGACAGGACCATGCCATAATGTCAGCACAGTACAATGT
ACACATGGAATTAAGCCAGTGGTATCAACTCAACTACTGTTAAATGGTAGCCTAGCAGAAGAAGGGATAATAATT
AGATCTGAAAATCTGACAAACAATGTCAAAACAATAATAGTACATCTTAATAGATCTATAGAAATTGTGTGTGTA
AGACCCAACAATAATACAAGACAAAGTATAAGAATAGGACCAGGACAAACATTCTATGCAACAGGAGACATAAT
AGGAGACATAAGACAAGCACATTGTAACATTAGTAGGACTAACTGGACTAAGACTTTACGAGAGGTAAGGAACA
AATTAAGAGAACACTTCCCTAATAAAAACATAACATTTAAACCATCCTCAGGAGGGGACCTAGAAATTACAACAC
ATAGCTTTAATTGTAGAGGAGAATTTTTCTATTGCAATACATCGGGCCTGTTTAGTATAAATTATACAGAAAATAA
TACAGATGGTACACCCATCACACTCCCATGCAGAATAAGACAAATTATAAATATGTGGCAGGAAGTAGGACGAGC
AATGTACGCCCCTCCCATTGAAGGAAACATAGCATGTAAATCAGATATCACAGGGCTACTATTGGTTCGGGATGG
AGGAAGCACAAATGATAGCACAAATAATAACACAGAGATATTCAGACCTGCAGGAGGAGATATGAGGGACAATT
GGAGGAGTGAATTGTATAAGTATAAAGTGGTAGAAATTAAGCCATTGGGAATAGCACCCACTGAGGCAAAAAGG
AGAGTGGTGGAGTAA (SEQ ID NO:11)

FIG. 33

Codon optimized gp120.Czm DNA sequence:

TGGGGCAACCTGTGGGTGACCGTGTACTACGGCGTGCCCGTGTGGAAGGAGGCCAAGACCACCCTGTTCTGCGCCAGCG
ACGCCAAGAGCTACGAGAAGGAGGTGCACAACGTGTGGGCCACCCACGCCTGCGTGCCCACCGACCCCAACCCCCAGGA
GATCGTGCTGGGCAACGTGACCGAGAACTTCAACATGTGGAAGAACGACATGGTGGACCAGATGCACGAGGACATCATC
AGCCTGTGGGACCAGAGCCTGAAGCCCTGCGTGAAGCTGACCCCCCTGTGCGTGACCCTGAACTGCACCGAGGTGAACGT
GACCCGCAACGTGAACAACAGCGTGGTGAACAACACCACCAACGTGAACAACAGCATGAACGGCGACATGAAGAACTG
CAGCTTCAACATCACCACCGAGCTGAAGGACAAGAAGAAGAACGTGTACGCCCTGTTCTACAAGCTGGACATCGTGAGC
CTGAACGAGACCGACGACAGCGAGACCGGCAACAGCAGCAAGTACTACCGCCTGATCAACTGCAACACCAGCGCCCTGA
CCCAGGCCTGCCCCAAGGTGAGCTTCGACCCCATCCCCATCCACTACTGCGCCCCCGCCGGCTACGCCATCCTGAAGTGC
AACAACAAGACCTTCAACGGCACCGGCCCCTGCCACAACGTGAGCACCGTGCAGTGCACCCACGGCATCAAGCCCGTGG
TGAGCACCCAGCTGCTGCTGAACGGCAGCCTGGCCGAGGAGGGCATCATCATCCGCAGCGAGAACCTGACCAACAACGT
GAAGACCATCATCGTGCACCTGAACCGCAGCATCGAGATCGTGTGCGTGCGCCCCAACAACAACACCCGCCAGAGCATC
CGCATCGGCCCCGGCCAGACCTTCTACGCCACCGGCGACATCATCGGCGACATCCGCCAGGCCCACTGCAACATCAGCCG
CACCAACTGGACCAAGACCCTGCGCGAGGTGCGCAACAAGCTGCGCGAGCACTTCCCCAACAAGAACATCACCTTCAAG
CCCAGCAGCGGCGGCGACCTGGAGATCACCACCCACAGCTTCAACTGCCGCGGCGAGTTCTTCTACTGCAACACCAGCGG
CCTGTTCAGCATCAACTACACCGAGAACAACACCGACGGCACCCCCATCACCCTGCCCTGCCGCATCCGCCAGATCATCA
ACATGTGGCAGGAGGTGGGCCGCGCCATGTACGCCCCCCCCATCGAGGGCAACATCGCCTGCAAGAGCGACATCACCGG
CCTGCTGCTGGTGCGCGACGGCGGCAGCACCAACGACAGCACCAACAACAACACCGAGATCTTCCGCCCCGCCGGCGGC
GACATGCGCGACAACTGGCGCAGCGAGCTGTACAAGTACAAGGTGGTGGAGATCAAGCCCCTGGGCATCGCCCCCACCG
AGGCCAAGCGCCGCGTGGTGGAGCGCGAGAAGCGCTGA (SEQ ID NO:12)

FIG. 34

Wild type gp120.E DNA sequence

TTGTGGGTCACAGTCTATTATGGGGTACCTGTGTGGAAAGATGCAGATACCACCCTATTTTGTGCATCAGATGCCAA
AGCACATGAGACAGAAGTGCACAATGTCTGGGCCACACATGCCTGTGTACCCACAGACCCCAACCCACAAGAAATA
CACCTGGAAAATGTAACAGAAAATTTTAACATGTGGAAAAATAAAATGGTAGAGCAGATGCAGGAGGATGTAATC
AGTTTATGGGATCAAAGTCTAAAGCCATGTGTAAAGTTAACTCCTCTCTGCGTTACTTTGACTTGTACCAATGCTACT
CTGAATTGTACCAATTTGACCAATGGCAATAAGACAACTAATGTCTCTAACATAATAGGAAATCTAACAGATGAAG
TAAGAAACTGTTCTTTTCATATGACCACAGAACTAAGAGATAAGAAGCAGAAGGTCTATGCACTTTTTTATAAGCTT
GATATAGTACAAATTAATAGTAGTGAGTATAGGTTAATAAATTGTAATACTTCAGTCATTAAGCAGGCTTGTCCAAA
GATATCCTTTGATCCAATTCCTATACATTATTGTACTCCAGCTGGTTATGCGATTTTAAAGTGTAATGATAAGAATTT
CAATGGGACAGGGCCATGTAAAAATGTCAGCTCAGTACAATGCACACATGGAATTAAGCCAGTGGTATCAACTCAA
TTGCTGTTAAATGGCAGTCTAGCAGAAGAAGAGATAATAATCAGCTCTGAAAATCTCACAAACAATGCCAAAACCA
TAATAGTGCACCTTAATAAATCTGTAGAAATCAGTTGTACCAGACCCTCCACCAATACAAGAACAAGTATACGTAT
AGGACCAGGACAAGTATTCTATAGAACAGGAGACATAACAGGAGATATAAGAAAAGCATATTGTGAGATTAATGA
AACAAAATGGAATGAAGCTTTAAAACAGGTAGCTGGGAAATTAAAAGAACACTTTAATAAGACAATAATCTTTCAA
CCACCCTCAGGAGGAGATCTAGAAATTACAATGCATCATTTTAATTGTAGAGGGGAATTTTTCTATTGCGATACAAC
ACAACTGTTTAATAGAACTTGGGGAGAAAATGAAACCAGAGAGGGGCGTAATATCACACTTCCATGCAAGATAAA
GCAAATTGTAAACATGTGGCAGGGAGCAGGGCAAGCAATGTATGCTCCTCCCATCAGTGGAATAATTAAGTGTGTA
TCAAATATTACAGGAATACTATTGACAAGAGATGGTGGTGCTAATAATTCGGCTAGTGAGACCTTCAGACCTGGAG
GAGGAAATATAAAGGACAATTGGAGAAGTGAATTATATAAATATAAAGTAGTACAAATTGAACCACTAGGAATAG
CACCCACCAGGGCAAAGAGAAGAGTGGTGGAGTAA (SEQ ID NO:13)

FIG. 35

Codon optimized gp120.E DNA sequence:

CTGTGGGTGACCGTGTACTACGGCGTGCCCGTGTGGAAGGACGCCGACACCACCCTGTTCTGCGCCAGCGACGCCAAGG
CCCACGAGACCGAGGTGCACAACGTGTGGGCCACCCACGCCTGCGTGCCCACCGACCCCAACCCCCAGGAGATCCACCT
GGAGAACGTGACCGAGAACTTCAACATGTGGAAGAACAAGATGGTGGAGCAGATGCAGGAGGACGTGATCAGCCTGT
GGGACCAGAGCCTGAAGCCCTGCGTGAAGCTGACCCCCCTGTGCGTGACCCTGACCTGCACCAACGCCACCCTGAACTG
CACCAACCTGACCAACGGCAACAAGACCACCAACGTGAGCAACATCATCGGCAACCTGACCGACGAGGTGCGCAACTG
CAGCTTCCACATGACCACCGAGCTGCGCGACAAGAAGCAGAAGGTGTACGCCCTGTTCTACAAGCTGGACATCGTGCAG
ATCAACAGCAGCGAGTACCGCCTGATCAACTGCAACACCAGCGTGATCAAGCAGGCCTGCCCCAAGATCAGCTTCGACC
CCATCCCCATCCACTACTGCACCCCTGCTGGCTACGCCATCCTGAAGTGCAACGACAAGAACTTCAACGGCACCGGACC
CTGCAAGAACGTGAGCAGCGTGCAGTGCACCCACGGCATCAAGCCCGTGGTGAGCACCCAGCTGCTGCTGAACGGCAG
CCTGGCCGAGGAGGAGATCATCATCAGCAGCGAGAACCTGACCAACAACGCCAAGACCATCATCGTGCACCTGAACAA
GAGCGTGGAGATCAGCTGCACTCGCCCCAGCACCAACACCCGCACCAGCATCCGCATCGGACCTGGCCAGGTGTTCTAC
CGCACCGGCGACATCACCGGCGACATCCGCAAGGCCTACTGCGAGATCAACGAGACCAAGTGGAACGAGGCCCTGAAG
CAGGTGGCCGGCAAGCTGAAGGAGCACTTCAACAAGACCATCATCTTCCAGCCTCCCAGCGGAGGCGACCTGGAGATC
ACCATGCACCACTTCAACTGCAGAGGCGAGTTCTTCTACTGCGACACCACCCAGCTGTTCAACCGCACCTGGGGCGAGA
ACGAGACCCGCGAGGGCAGGAACATCACCCTGCCCTGCAAGATCAAGCAGATCGTGAACATGTGGCAGGGAGCTGGCC
AGGCCATGTACGCCCCACCCATCAGCGGCATCATCAAGTGCGTGAGCAACATCACCGGCATCCTGCTGACCCGCGACGG
CGGTGCCAACAACAGCGCCAGCGAGACCTTCAGGCCAGGCGGTGGCAACATCAAGGACAACTGGCGCAGCGAGCTGTA
CAAGTACAAGGTGGTGCAGATCGAGCCCCTGGGCATCGCCCCCACTCGCGCCAAGCGCCGCGTGGTGGAGTAA (SEQ ID
NO:14)

FIG. 36

Wild type gp120.A DNA sequence:

TTGTGGGTCACAGTCTATTATGGGGTACCTGTGTGGAAAGATGCAGAGACTACCTTATTTTGTGCATCAGA
TGCGAAAGCATATGATACAGAAGTGCATAATGTCTGGGCTACGCATGCCTGTGTACCTACAGACCCCAAC
CCACAAGAAATATATATGGAAAATGTGACAGAAGAGTTTAACATGTGGAAAAATAACATGGTAGAGCAG
ATGCATACAGATATAATCAGTCTATGGGACCAAAGCCTAAAACCATGTGTACAGTTAACCCCTCTCTGCGT
TACTTTAGATTGTAGCTATAACATCACCAATAATATCACCAATAGCATCACCAATAGCTCAGTTAACATGA
GAGAAGAAATAAAAAACTGCTCTTTCAATATGACCACAGAATTAAGGGATAAGAATCGGAAGGTATATT
CACTTTTTTATAAACTTGATGTAGTACAAATTAATAATGGTAATAACAGTAGTAATCTGTATAGATTAATA
AATTGTAATACCTCAGCCCTTACACAGGCTTGTCCAAAGGTAACCTTTGAGCCAATTCCCATACGTTATTG
TGCCCCAGCTGGTTATGCGATTCTAAAATGTAATGATAAGGAGTTCAATGGAACAGGGCTATGCAAAAAT
GTCAGCACAGTGCAATGCACACATGGAATCAGGCCAGTAGTATCAACTCAACTGCTGTTAAATGGCAGTT
TAGCAGAAGGAAAGGTAATGATTAGATCTGAAAATATCACAAACAATGTCAAAAACATAATAGTACAAC
TTAACGAGACTGTAACAATTAATTGTACCAGACCTAACAACAATACAAGAAAAAGTGTACGTATAGGACC
AGGACAAACATTCTATGCAACAGGTGATATAATAGGGGATATAAGACAAGCACATTGTAATGTCAGTGG
GTCACAATGGAATAGAGCTTTACACCAGGTAGTTGGACAATTAAGAGAATACTGGAACACAACAATAATC
TTTAAAAACTCCTCAGGAGGGGATTTAGAAATTACAACACATAGTTTTAATTGTGGAGGAGAATTTTTCTA
TTGTAATACATCAGGCCTGTTTAATAGTAATTGGACACATAATGACACTGCCAGCATGAAACCAAATGAC
ACTATAACACTCCCATGCAGAATAAAGCAAATTATAAATATGTGGCAGAGAGTAGGACAAGCAATATAT
GCCCCTCCCATTCAAGGAGTAATAAGGTGTGAATCAAACATTACAGGACTAATATTAACAAGAGATGGTG
GGGGTAACATCAATGAAAGTCAAATCTTCAGACCTGGAGGAGGAGATATGAGGGACAATTGGAGAAGTG
AATTATATAAGTATAAGGTAGTAAGAATTGAACCACTAGGAGTAGCACCCACCAAGGCAAAGAGAAGAG
TGGTGGAGTAA (SEQ ID NO:15)

FIG. 37

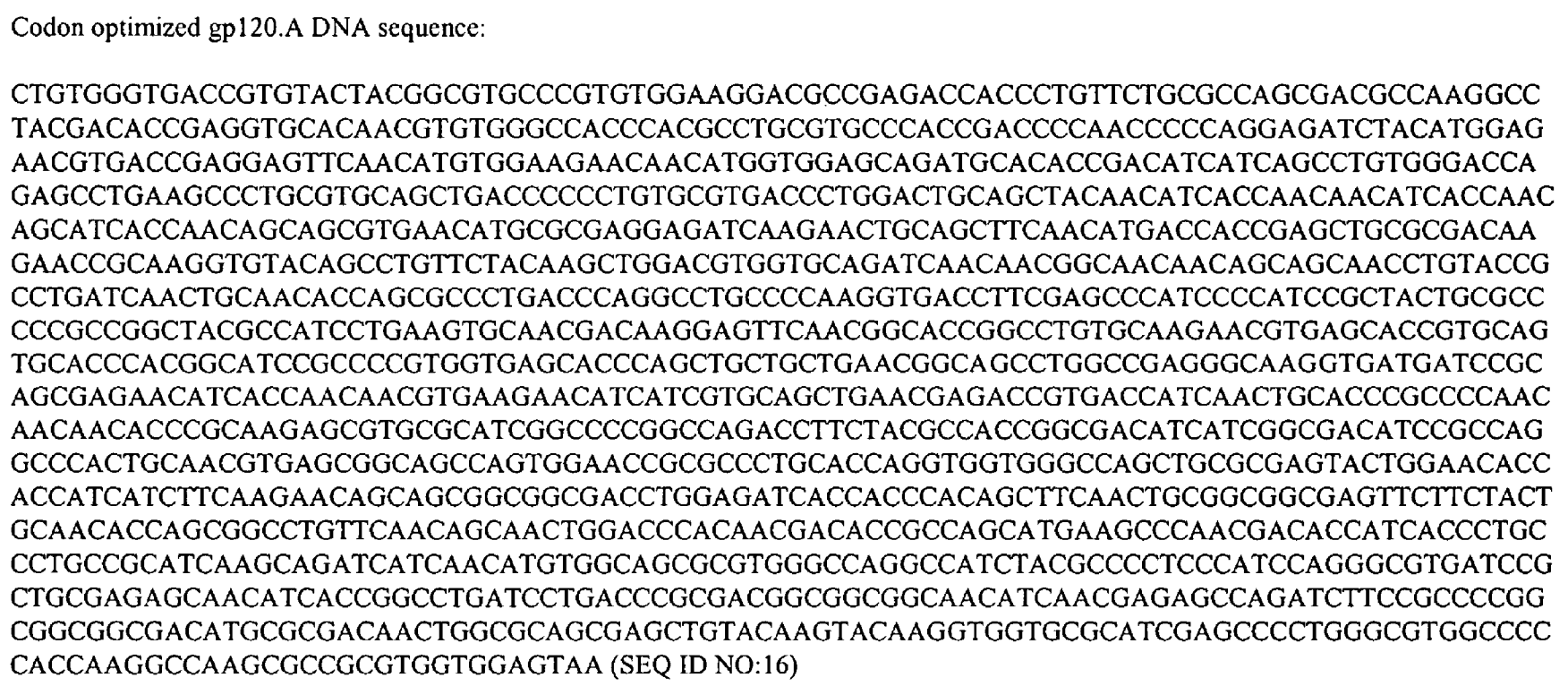

Codon optimized gp120.A DNA sequence:

CTGTGGGTGACCGTGTACTACGGCGTGCCCGTGTGGAAGGACGCCGAGACCACCCTGTTCTGCGCCAGCGACGCCAAGGCC
TACGACACCGAGGTGCACAACGTGTGGGCCACCCACGCCTGCGTGCCCACCGACCCCAACCCCCAGGAGATCTACATGGAG
AACGTGACCGAGGAGTTCAACATGTGGAAGAACAACATGGTGGAGCAGATGCACACCGACATCATCAGCCTGTGGGACCA
GAGCCTGAAGCCCTGCGTGCAGCTGACCCCCCTGTGCGTGACCCTGGACTGCAGCTACAACATCACCAACAACATCACCAAC
AGCATCACCAACAGCAGCGTGAACATGCGCGAGGAGATCAAGAACTGCAGCTTCAACATGACCACCGAGCTGCGCGACAA
GAACCGCAAGGTGTACAGCCTGTTCTACAAGCTGGACGTGGTGCAGATCAACAACGGCAACAACAGCAGCAACCTGTACCG
CCTGATCAACTGCAACACCAGCGCCCTGACCCAGGCCTGCCCCAAGGTGACCTTCGAGCCCATCCCCATCCGCTACTGCGCC
CCCGCCGGCTACGCCATCCTGAAGTGCAACGACAAGGAGTTCAACGGCACCGGCCTGTGCAAGAACGTGAGCACCGTGCAG
TGCACCCACGGCATCCGCCCCGTGGTGAGCACCCAGCTGCTGCTGAACGGCAGCCTGGCCGAGGGCAAGGTGATGATCCGC
AGCGAGAACATCACCAACAACGTGAAGAACATCATCGTGCAGCTGAACGAGACCGTGACCATCAACTGCACCCGCCCCAAC
AACAACACCCGCAAGAGCGTGCGCATCGGCCCCGGCCAGACCTTCTACGCCACCGGCGACATCATCGGCGACATCCGCCAG
GCCCACTGCAACGTGAGCGGCAGCCAGTGGAACCGCGCCCTGCACCAGGTGGTGGGCCAGCTGCGCGAGTACTGGAACACC
ACCATCATCTTCAAGAACAGCAGCGGCGGCGACCTGGAGATCACCACCCACAGCTTCAACTGCGGCGGCGAGTTCTTCTACT
GCAACACCAGCGGCCTGTTCAACAGCAACTGGACCCACAACGACACCGCCAGCATGAAGCCCAACGACACCATCACCCTGC
CCTGCCGCATCAAGCAGATCATCAACATGTGGCAGCGCGTGGGCCAGGCCATCTACGCCCCTCCCATCCAGGGCGTGATCCG
CTGCGAGAGCAACATCACCGGCCTGATCCTGACCCGCGACGGCGGCGGCAACATCAACGAGAGCCAGATCTTCCGCCCCGG
CGGCGGCGACATGCGCGACAACTGGCGCAGCGAGCTGTACAAGTACAAGGTGGTGCGCATCGAGCCCCTGGGCGTGGCCCC
CACCAAGGCCAAGCGCCGCGTGGTGGAGTAA (SEQ ID NO:16)

FIG. 38

POLYVALENT, PRIMARY HIV-1 GLYCOPROTEIN DNA VACCINES AND VACCINATION METHODS

CROSS-REFERENCE TO RELATED APPLICATIONS

This application claims the benefit of priority to U.S. Provisional Patent Application Ser. No. 60/430,732, filed on Dec. 3, 2002, and to U.S. Provisional Patent Application Ser. No. 60/503,907, filed on Sep. 19, 2003, the entire contents of both of which are herein incorporated by reference.

TECHNICAL FIELD

The invention relates to methods and compositions for the treatment of acquired immunodeficiency syndrome (AIDS).

BACKGROUND

Human immunodeficiency virus (HIV) is the etiological agent of AIDS. There are two types of HIV currently recognized, HIV-1 and HIV-2. HIV-1 is the predominant form worldwide. The form of HIV-1 that dominates the global epidemic is called the major group of HIV-1. There are three HIV-1 groups, the major group (M group), the outlier group (O group), and the non-M/non-O group (N group). The M group is further divided into at least eleven distinct genetic subtypes which are commonly referred to as clades, A, B, C, D, E, F, G. H, I, J, and K, with more sequences awaiting to be classified. Clade B is the most prevalent in the United States, while clade C is the most prevalent worldwide. Geographic distribution of genetic subtypes is continually changing, and current data offers incomplete estimates.

Approximately 95% of the new HIV infections are occurring in developing countries, thus a vaccine may be the most effective way to control the epidemic. However, developing effective vaccines to prevent HIV infection or neutralize HIV infection has been a difficult challenge to the scientific community. It is a primary goal to develop an HIV vaccine that can effectively elicit specific anti-viral neutralizing antibodies as well as cell-mediated immune responses to prevent infection and control the spread of HIV, with a potential for considerable breadth of reactivity across genetic clades. The extraordinary degree of genetic diversity of HIV has been problematic for vaccine development.

SUMMARY

The methods and compositions provided herein are based, in part, on the discovery that polyvalent, primary isolate DNA vaccines effectively induce an immune response against HIV (e.g., HIV-1). It has also been discovered that boosts with recombinant HIV protein compositions increase immune responses against HIV in subjects that have been administered a polyvalent, primary isolate DNA vaccine.

In general, the invention features nucleic acid compositions including a plurality of sets of nucleic acid molecules, e.g., DNA plasmids, each nucleic acid molecule encoding a human immunodeficiency virus (HIV), e.g., HIV-1, envelope glycoprotein, wherein each set of nucleic acid molecules encodes a different type of HIV envelope glycoprotein, or comprises a primary isolate sequence from a distinct genetic clade. The nucleic acids can be wild-type sequences or sequences that are 80, 90, 95, 98, or 99 percent identical to wild-type sequences. The encoded proteins can be wild-type sequences, or can include conservation amino acid substitutions, e.g., at 1 in 10, 1 in 20, 1 in 30, or fewer, e.g., at 1, 2, 5, or 10 amino acid locations. In certain embodiments, consensus sequences (based on a collection of different wild-type sequences) can be used.

In various embodiments, the HIV envelope glycoprotein can be any one or more of gp120, gp140, gp160, and gp41. The nucleic acid compositions can further include a set of nucleic acid molecules encoding a HIV gag protein. The envelope glycoproteins can be from a clade of a major (M) group of clades, e.g., the clade can be clade A, B, C, D, E, F, G. H, I, J, or K. In alternative embodiments, the envelope glycoprotein can be from a clade of an outlier (O) group of clades or an N group of clades. The envelope glycoprotein can be an envelope glycoprotein of a Ba-L isolate or a B715 isolate. The clade can be clade C. The envelope glycoprotein can be from a Czm isolate. In certain embodiments, one or more of the sets of nucleic acids can include one or more optimized codons.

In another aspect, the invention includes nucleic acid compositions that include a plurality of sets of nucleic acid molecules, wherein the plurality includes two or more of the following sets: a set of nucleic acid molecules, each encoding a human immunodeficiency virus (HIV) envelope glycoprotein of clade A; a set of nucleic acid molecules, each encoding a HIV envelope glycoprotein of clade B; a set of nucleic acid molecules, each encoding a HIV envelope glycoprotein of clade C; and a set of nucleic acid molecules, each encoding a HIV envelope glycoprotein of clade E; wherein each set of nucleic acid molecules encodes a primary isolate sequence of the envelope glycoprotein. In certain embodiments, the composition can further include a set of nucleic acid molecules encoding a human immunodeficiency virus (HIV) gag protein, wherein the set encodes a primary isolate sequence of the gag protein, e.g., from clade C, and/or from Czm isolate. The gag protein can also be a gag protein of clade B.

In various embodiments, the composition can contain between 50 μg and 2,500 μg of nucleic acid of each set.

In another aspect, the invention includes a pharmaceutical composition containing one or more of the new compositions described herein and a pharmaceutically acceptable excipient.

The invention also features methods of treating an individual with Acquired Immune Deficiency Syndrome (AIDS), by administering to the individual an amount of the new pharmaceutical compositions sufficient to inhibit disease progression due to human immunodeficiency virus (HIV). In these methods, the mode of administration can be topical administration, oral administration, injection by needle, needle-less jet injection, intradermal administration, intramuscular administration, and gene gun administration. The immune response can be a protective immune response, e.g., a cell-mediated immune response, a humoral immune response, or both.

In certain methods, the new compositions can be administered in combination with a second therapy for HIV infection, e.g., therapy a nucleoside reverse transcriptase inhibitor, therapy with a non-nucleoside reverse transcriptase inhibitor, and/or therapy with a HIV protease inhibitor.

The invention also includes methods of inducing an immune response against human immunodeficiency virus (HIV) or an HIV epitope in a vertebrate mammal by administering to the mammal an amount of the new compositions sufficient to elicit an immune response against HIV or an HIV epitope in the vertebrate mammal. These methods can further include isolating immune cells from the vertebrate mammal; and testing an immune response of the isolated immune cells in vitro. In these methods, the composition can be administered in multiple doses over an extended period of time, (e.g., over a period of 2, 3, 4 weeks or more, e.g., several months).

The methods can also include administering an adjuvant, boost, or facilitating agent before, during, or after administration of the composition. The vertebrate mammals can be a mouse, a rat, a rabbit, a non-human primate, or a human, e.g., a human infected with, or at risk for infection by, HIV. The mode of administration can be topical administration, oral administration, injection by needle, needle-less jet injection, intramuscular administration, intradermal administration, and gene gun administration.

In another aspect, the invention features isolated protein compositions including a set of isolated human immunodeficiency virus (HIV) envelope glycoprotein molecules, wherein each molecule in the set includes a primary isolate sequence.

The invention also includes protein compositions that include a plurality of sets of isolated human immunodeficiency virus (HIV), e.g., HIV-1, envelope glycoprotein molecules, wherein each molecule in the sets includes a different type of HIV envelope glycoprotein, or a primary isolate sequence from a distinct genetic clade. For example, the envelope glycoprotein of each set can be one or more of gp120, gp140, gp160, and gp41. The clades and isolates can be the same as described herein for the nucleic acid compositions. The protein compositions can be included in pharmaceutical compositions that include a pharmaceutically acceptable excipient.

The invention also features methods of treating an individual with Acquired Immune Deficiency Syndrome (AIDS), by administering to the individual an amount of the new pharmaceutical compositions sufficient to inhibit disease progression due to human immunodeficiency virus (HIV).

In another aspect, the invention includes methods of inducing an immune response against human immunodeficiency virus (HIV) or a HIV epitope in a vertebrate mammal by administering to the mammal one or more of the nucleic acid compositions, and administering to the mammal one or more of the new protein compositions; wherein the nucleic acid composition and the protein composition are administered in amounts sufficient to elicit a detectable immune response against HIV or an HIV epitope in the vertebrate mammal. One can also isolate immune cells from the vertebrate mammal and test an immune response of the isolated immune cells in vitro.

In these methods, the protein composition can be administered after the nucleic acid composition, e.g., between 4 and 8 weeks after the nucleic acid composition. In addition, a cell-mediated immune response can be tested, a humoral immune response can be tested, and/or a neutralizing humoral response can be tested.

The invention also features kits that include one or more of the new nucleic acid compositions, and instructions for administering the nucleic acid compositions to an individual, e.g., according to one or more of the methods described herein. The kits can also include one or more of the new protein compositions that include a set of isolated human immunodeficiency virus (HIV) envelope glycoprotein molecules. The kits can further include one or more additional sets of isolated HIV envelope glycoproteins, wherein each set is a different type of HIV envelope glycoprotein, or comprises a primary isolate sequence from a distinct genetic clade. In these kits, one or more of the HIV envelope glycoproteins encoded by the nucleic acid molecules of the nucleic acid composition can be of a same type or clade as one or more, or each, of the envelope glycoproteins of the protein composition.

The kits can also include one or more of the new protein compositions that include a set of isolated human immunodeficiency virus (HIV) envelope glycoprotein molecules, wherein each set includes a different type of HIV envelope glycoprotein, or a primary isolate sequence from a distinct genetic clade; and instructions for administration of the composition to an individual that has been administered an HIV vaccine, e.g., a nucleic acid HIV vaccine. The kit can include an excipient, e.g., cyclodextrin, and/or an adjuvant, such as QS-21.

The instructions in the kit can indicate that the nucleic acid composition and/or the protein composition is to be administered to the individual two or more times.

The invention also includes methods of increasing an immune response to HIV in an individual that has been inoculated with an HIV vaccine, by administering to the individual one or more of the new compositions in an amount effective to increase the immune response to HIV relative to a control. For example, the individual can have been inoculated with a nucleic acid HIV vaccine.

A "vaccine" is a composition that induces an immune response in the recipient or host of the vaccine. Methods and compositions described herein cover a nucleic acid, e.g., DNA plasmid, vaccine that induces humoral (e.g., neutralizing antibody) responses and/or cell-mediated immune response (e.g., cytotoxic T lymphocyte (CTL)) responses in the recipient as protection against current or future HIV (e.g., HIV-1) infection. The vaccine can induce protection against infection upon subsequent challenge with HIV. Protection refers to resistance (e.g., partial resistance) to persistent infection of a host animal with HIV. Neutralizing antibodies generated in the vaccinated host can provide this protection. In other situations, CTL responses can provide this protection. In some situations, both neutralizing antibodies and cell-mediated immune (e.g., CTL) responses provide this protection.

Protective responses can be evaluated by a variety of methods. For example, the generation of neutralizing antibodies against HIV proteins (e.g., envelope glycoproteins, "Env gps"), and the generation of a cell-mediated immune response against HIV proteins can both indicate a protective response. Protective responses also include those responses that result in lower viral loads (e.g., in the blood or in lymphoid organs) in a vaccinated host animal exposed to a given inoculum of virus as compared to a host animal exposed to the inoculum of virus, and that has not been administered the vaccine. "Polyvalency" and "multivalency" are used interchangeably herein and refer to a feature of a nucleic acid or protein composition, e.g., DNA vaccine or protein boost composition, that encodes or comprises a plurality of different proteins. Each nucleic acid, e.g., plasmid, encodes either a different HIV envelope glycoprotein (Env gp) or Env gp in the form of defective HIV viral particles, or an HIV envelope glycoprotein from different clades, or a combination of these possibilities, allowing for flexibility of this polyvalent nucleic acid, e.g., DNA plasmid, vaccine. As used herein, "envelope glycoproteins" (Env gps) refer not only to isolated Env gps, but also to Env gps in the form of defective viral particles. "3-valent" refers to a composition of three distinct antigens (e.g., an env gene of a clade A isolate, and env gene of a clade B isolate, and an env gene of a clade C isolate). Likewise, "4-valent" and "8-valent" refer to compositions with 4 and 8 unique antigens, respectively.

"DP6-001", "DP6-001 formulation", and "DP6-001 vaccine" refers to a formulation of DNA and protein. The DNA component of DP6-001 is a composition containing codon-optimized nucleic acids that encode five different HIV-1 Env (gp120) antigens and a single Gag antigen. The gp120 antigens are from HIV-1 isolates A, B715, Ba-L, Czm, and E. The Gag antigen is from isolate Czm. The protein component of DP6-001 is a protein composition containing five different HIV-1 gp120 antigens from HIV-1 isolates A, B715, Ba-L, Czm, and E.

"Primary viral isolate" or "primary isolate" nucleic acid or amino acid sequences refer to nucleic acid or amino acid sequences from the cells or sera of individuals infected with HIV (e.g., HIV-1) rather than from a laboratory strain of HIV. A primary viral isolate is a viral isolate that has been expanded and maintained only in primary human T cells, monocytes, and/or macrophages, and has not been expanded and maintained in cell lines. Thus, a primary isolate differs from what is referred to as a "laboratory strain."

Laboratory strains of HIV have been passaged extensively in the laboratory, in some cases for many years. They may be referred to as TCLA strains, which stands for either tissue culture laboratory adapted strains or T cell line adapted strains. On the other hand, primary viral isolates are collected from the field (e.g., from infected human patients) and expanded or passaged in the laboratory, for example, only for the purpose of determining whether or not growth of the virus is possible, and then subsequently one can obtain the viral sequence. Expansion or passaging of the primary isolates occurs by co-culturing the virus with peripheral blood mononuclear cells, for example, to determine if viral growth can occur. The amount of expansion/passaging is dependent on the particular virus and can vary, but in any case, expansion/passaging is thus considered minimal or limited. This minimal or limited passaging is what differentiates a primary viral isolate from a laboratory strain.

The invention provides several advantages. Because of its polyvalency, the new vaccines are less likely to lose their efficacy due to the high mutation rate of HIV. The nucleic acid vaccines described herein provide many different antigens in the form of sequences from distinct genetic clades and thus single mutations of the infecting virus will not readily decrease the vaccines' effectiveness in recipients. Another advantage the invention provides is the induction of broader immune responses, because the different proteins are encoded by primary viral isolate sequences rather than laboratory strains.

The administration of both polyvalent DNA compositions and protein boosts elicits robust humoral and cell-mediated immune responses. The use of the combinations of compositions described herein provides neutralizing antibody responses. The presence of humoral and cell-mediated responses affords better protection from infection in naïve individuals. The presence of humoral and cell-mediated immune responses can delay disease progression in individuals that are infected with the virus prior to vaccination.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, the drawings, and from the claims.

BRIEF DESCRIPTION OF THE DRAWINGS

FIG. 2 is a table depicting percent neutralization of primary HIV-1 isolates by sera isolated from rabbits immunized with monovalent and polyvalent vaccines. Sera were isolated after DNA immunization. Animal numbers correspond to the rabbit numbers shown in FIG. 1.

FIG. 3 is a table depicting percent neutralization of primary HIV-1 isolates by sera isolated from rabbits immunized with monovalent and polyvalent vaccines. Sera were isolated after the first protein boost. Animal numbers correspond to the rabbit numbers shown in FIG. 1.

FIG. 4 is a table depicting percent neutralization of primary HIV-1 isolates by sera isolated from rabbits immunized with monovalent and polyvalent vaccines. Sera were isolated after two protein boosts. Animal numbers correspond to the rabbit numbers shown in FIG. 1.

FIGS. 7A and 7B depict data for sera tested against B Env protein. FIGS. 7C and 7D depict data for sera tested against C1 Env protein. FIGS. 7E and 7F depict data for sera tested against E Env protein.

FIGS. 8A-P are graphs depicting anti-gp120 IgG responses against Env antigens included in the protein boost in 8-valent gp120 vaccine immunized animal group C7. Data for sera from rabbits immunized with Ba-L, B, C1, E, A, D, F, and G DNAs, and boosted with B, C1, E, and Ba-L proteins are presented. FIGS. 8A and 8B depict data for sera tested against B Env protein. FIGS. 8C and 8D depict data for sera tested against Ba-L Env protein. FIGS. 8E and 8F depict data for sera tested against C Env protein. FIGS. 8G and 8H depict data for sera tested against E Env protein. FIGS. 8I and 8J depict data for sera tested against A2 Env protein. FIGS. 8K and 8L depict data for sera tested against D Env protein. FIGS. 8M and 8N depict data for sera tested against F Env protein. FIGS. 8O and 8P depict data for sera tested against G Env protein.

FIG. 23A) and one (protein 1; FIG. 23B) and two (protein 2; FIG. 23C) boosts were assayed for neutralizing activity against SHIVBa-L isolate in U373 cells. Percent inhibition of infection was based on the degree of infection observed in the presence of immune serum compared to untreated controls.

FIGS. 26A and 26C), and after first protein boost (protein 1; FIG. 26B and 26D). Four pools of 15 mer peptides with 11 amino acid overlap from gp120 proteins from HIV-1 $_{Ba-L}$ and clade E isolates were used for stimulation of PBMC for 18 hrs before the spots were developed.

FIGS. 27-38 are representations of wild-type and codon-optimized DNA sequences of gp120 and gag genes of Czm, Ba-L, B, E, and A HIV-1 isolates.

DETAILED DESCRIPTION

Figure 1:
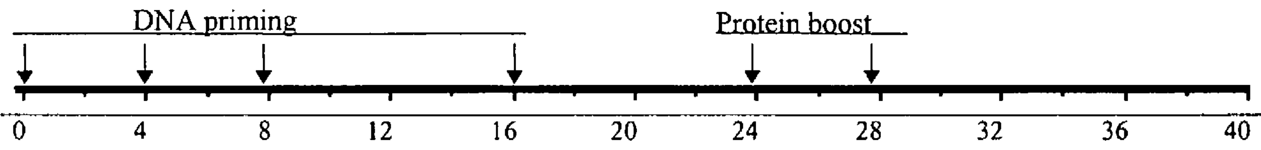
FIG. 1 is a table depicting DNA and protein antigens, and the program of administration of DNA and protein antigens in vaccination studies in rabbits.

The methods and compositions provided herein are based, in part, on the finding that primary HIV-1 isolates from multiple different genetic subtypes of HIV can be combined to create polyvalent DNA compositions that can induce broad antibody responses (e.g., neutralizing antibody responses) and cell-mediated immune responses (e.g., cytotoxic T lymphocyte (CTL)). The methods and compositions provided herein are also based on the finding that protein boosts, in which HIV proteins from primary isolates can be used to augment immune responses in subjects that have been administered polyvalent DNA compositions. Recent strategies have suffered from only minimal immune protection due to escape from CTL recognition (Barouch et al., 2002, Nature, 415: 335-339; Goulder et al., 2001, Nature, 412:334-338; Goulder et al., 1997, Nature Med., 3:212-217). To address this problem, nucleic acid sequences from primary HIV-1 isolates are used to generate polyvalent compositions, thus improving cell-mediated immune responses and decreasing the likelihood of CTL escape by the virus, as well as improving neutralizing antibody response. The new methods provide for flexibility in designing compositions based on combinations of vectors encoding different HIV-1 proteins and combinations of HIV-1 proteins.

The protein boosts can include HIV proteins corresponding to the all of the proteins encoded by DNA administered in prior DNA vaccination steps. Alternatively, a subset of proteins corresponding to the DNA vaccine is administered. For example, if DNA encoding five different HIV proteins are administered (e.g., Env genes from five different HIV-1 isolates), the subsequent protein boost(s) can include all five of the Env proteins, four of the Env proteins, or fewer.

The DNA and protein compositions can include different genes and proteins from HIV isolates. In some embodiments, Env and Gag antigens are encoded by the DNA compositions, and the Env antigens are included in the protein compositions. Accordingly, provided herein are compositions comprising Env glycoproteins (gps), a combination of vectors encoding Env glycoproteins derived from the sequences of more than one HIV-1 primary isolate (e.g., lade A, B, C, D, E, F, or G), a combination of both different types and different clades, and/or combinations encoding HIV-1 gag proteins.

The DNA and protein compositions can include sequences from isolates of multiple clades, or multiple isolates of a single lade. Different combinations may be used. For example, a DNA composition can include genes encoding an antigen from one lade A isolate, one clade B isolate, one clade C isolate, and one clade E isolate. The composition can further include an antigen of a second clade B isolate.

Coding sequences for primary HIV-1 Env gps can be cloned into nucleic acid, e.g., DNA, vaccine vectors to produce a panel of DNA vaccine plasmids. The HIV envelope is the predominant target of neutralizing antibodies in HIV-infected individuals. Thus, a vaccine encoding Env gps can be used to induce neutralizing antibodies. The primary HIV-1 Env gps include gp120, gp140, gp160, and sgp41. To prepare the new vaccines, these Env gps can be encoded by nucleic acids, e.g., DNA, from primary isolates covering seven genetic clades, A, B, C, D, E, F, and G of the HIV-1 major group. These sequences were isolated from distinct geographic regions: North America, Africa, Asia, and South America. The Env gps can also be encoded by DNA from primary isolates covering other genetic clades of the HIV-1 major group (e.g., H, I, J, and K), genetic clades of the HIV-1 O group, and genetic clades of the HIV-1 N group.

Because of the genetic diversity of HIV, the vaccines based on antigens from laboratory strains of HIV-1, as opposed to primary isolates, have been limited in their ability to generate broad immune responses against the prevalent HIV primary strains (e.g., see Barouch et al., 2002, Nature, 415:335-339; Johnston and Flores, 2001, Curr. Op. In. Pharmac., 1:504-510; and Mascola et al., 1996, J. Infect. Dis.,173:340-348). By combining multiple nucleic acid molecules (e.g., DNA plasmids) encoding primary isolate proteins (e.g., multiple Env gps) into one polyvalent vaccine, the new vaccines provide a considerable breadth of reactivity across genetic clades. Primary isolate DNA can be directly collected from HIV infected patients, passaged minimally if at all, sequenced, and cloned into multiple DNA vaccine vectors to make a polyvalent vaccine. Minimal passaging may be required to expand the DNA if not enough DNA is available for sequencing. This polyvalent vaccine elicits a broad immune response and broad neutralization against Env gps from the different isolates. The polyvalency decreases the likelihood of low efficacy caused by the constantly changing genetic diversification and mutation of HIV.

Nucleic Acid Vaccines

Vaccines are useful in preventing or reducing infection or disease by inducing immune responses, to an antigen or antigens, in an individual. For example, vaccines can be used prophylactically in naive individuals, or therapeutically in individuals already infected with HIV. Traditional vaccines, which include inactivated viruses or subunit protein antigen, have had poor immunogenicity, poor cell-mediated immunity induction, safety and stability concerns, and low efficacy. The development of nucleic acid vaccines has proved to be promising.

The new DNA vaccines have the advantage of being more resilient to the rapid evolution and mutation of HIV due to their polyvalency. The new DNA vaccines have the added advantage of being derived from primary isolates, which in combination with their polyvalency can induce broader immune response, namely more effective neutralizing antibodies against HIV (e.g., HIV-1) and/or cell-mediated immune responses (e.g., cytotoxic T lymphocyte (CTL)), thus providing a more effective HIV vaccine. This combination of polyvalency and being derived from primary isolate DNA confers its advantages as a novel vaccine for HIV (e.g., HIV-1).

Nucleic Acid Compositions

Nucleic acid compositions that encode antigens of primary HIV isolates are provided. There are many ways of presenting nucleic acid encoding antigen to a host. DNA vaccines can consist of naked DNA plasmid encoding the antigen. Bacterial vectors, replicon vectors, live attenuated bacteria, DNA vaccine co-delivery with live attenuated vectors, and viral vectors for expression of heterologous genes also can be used. Bacterial vectors such as BCG and Listeria can also be used. In the case of naked DNA replicon vectors, a mammalian expression plasmid serves as a vehicle for the initial transcription of the replicon. The replicon is amplified within the cytoplasm, resulting in more abundant mRNA encoding the heterologous gene such that initial transfection efficiency may be less important for immunogenicity. Live attenuated viral vectors (e.g., recombinant vaccinia (e.g., modified vaccinia Ankara (MVA), IDT Germany), recombinant adenovirus, avian poxvirus (e.g., canarypox (e.g., ALVAC®, Aventis Pasteur) or fowlpox), poliovirus, and alphavirus virion vectors) have been successful in inducing cell-mediated immune response and can be used as well. The avian poxviruses are defective in mammalian hosts, but can express inserted heterologous genes under early promoters. Recombinant adenovirus and poliovirus vectors can thrive in the gut and so can stimulate efficient mucosal immune responses. Finally, attenuated bacteria can also be used as a vehicle for DNA vaccine delivery. Examples of suitable bacteria include *S. enterica, S. tymphimurium*, Listeria, and BCG The use of mutant bacteria with weak cell walls can aid the exit of DNA plasmids from the bacterium.

DNA uptake can sometimes be improved by the use of the appropriate adjuvants. Synthetic polymers (e.g., polyamino acids, co-polymers of amino acids, saponin, paraffin oil, muramyl dipeptide, Regressin (Vetrepharm, Athens Ga.), and Avridine) and liposomal formulations can be added as adjuvants to the vaccine formulation to improve DNA stability and DNA uptake by the host cells, and may decrease the dosage required to induce an effective immune response. Regardless of route, adjuvants can be administered before, during, or after administration of the nucleic acid. Not only can the adjuvant increase the uptake of nucleic acid into host cells, it can increase the expression of the antigen from the nucleic acid within the cell, induce antigen presenting cells to infiltrate the region of tissue where the antigen is being expressed, or increase the antigen-specific response provided by lymphocytes.

Nucleic acid uptake can be improved in other ways as well. For example, DNA uptake via IM delivery of vaccine can be improved by the addition of sodium phosphate to the formulation. Increased DNA uptake via IM delivery can also be accomplished by electrotransfer (e.g., applying a series of electrical impulses to muscle immediately after DNA immunization). Adjuvants which can also be added to the vaccine to improve DNA stability and uptake as well as improve immune induction include water emulsions (e.g., complete and incomplete Freund's adjuvant), oil, *Corynebacterium parvum*, Bacillus Calmette Guerin, iron oxide, sodium alginate, aluminum hydroxide, aluminum and calcium salts (i.e., alum), unmethylated CpG motifs, glucan, and dextran sulfate. Coinjection of cytokines, ubiquitin, or costimulatory molecules can also help improve immune induction. The antigens described herein can also be fused with cytokine genes, helper epitopes, ubiquitin, or signal sequences to enhance an immune response. Fusions can also be used to aid in targeting to certain cell types.

The medium in which the DNA vector is introduced should be physiologically acceptable for safety reasons. Suitable pharmaceutical carriers include sterile water, saline, dextrose, glucose, or other buffered solutions (e.g., phosphate buffered saline). Included in the medium can be physiologically acceptable preservatives, stabilizers, diluents, emulsifying agents, pH buffering agents, viscosity enhancing agents, colors, etc.

Once the DNA vaccine is delivered, the nucleic acid molecules (e.g., DNA plasmids) are taken up into host cells, which then express the plasmid DNA as protein. Once expressed, the protein is processed and presented in the context of self-major histocompatibility (MHC) class I and class II molecules. The host then develops an immune response against the DNA-encoded immunogen. To improve the effectiveness of the vaccine, multiple injections can be used for therapy or prophylaxis over extended periods of time. To improve immune induction, a prime-boost strategy can be employed. Priming vaccination with DNA and a different modality for boosting (e.g., live viral vector or protein antigen) has been successful in inducing cell-mediated immunity. The timing between priming and boosting varies and is adjusted for each vaccine.

Administration of DNA Vaccines

The nucleic acid compositions described herein can be administered, or inoculated, to an individual as naked nucleic acid molecules (e.g., naked DNA plasmid) in physiologically compatible solution such as water, saline, Tris-EDTA (TE) buffer, or in phosphate buffered saline (PBS). They can also be administered in the presence of substances (e.g., facilitating agents and adjuvants) that have the capability of promoting nucleic acid uptake or recruiting immune system cells to the site of inoculation. Adjuvants are described elsewhere herein. Vaccines have many modes and routes of administration. They can be administered intradermally (ID), intramuscularly (IM), and by either route, they can be administered by needle injection, gene gun, or needleless jet injection (e.g., Biojector™ (Bioject Inc., Portland, Oreg.). Other modes of administration include oral, intravenous, intraperitoneal, intrapulmonary, intravitreal, and subcutaneous inoculation. Topical inoculation is also possible, and can be referred to as mucosal vaccination. These include intranasal, ocular, oral, vaginal, or rectal topical routes. Delivery by these topical routes can be by nose drops, eye drops, inhalants, suppositories, or microspheres.

Suitable doses of nucleic acid compositions for humans can range from 1 μg/kg to 1 mg/kg of total nucleic acid, e.g., from 5 μg/kg-500 mg/kg of total DNA, 10 μg/kg-250 μg/kg of total DNA, or 10 μg/kg-170 μg/kg of total DNA. In one embodiment, a human subject (18-50 years of age, 45-75 kg) is administered 1.2 mg-7.2 mg of DNA. "Total DNA" and "total nucleic acid" refers to a pool of nucleic acids encoding distinct antigens. For example, a dose of 50 mg of total DNA encoding 5 different Env antigens can have 1 mg of each antigen. DNA vaccines can be administered multiple times, e.g., between two-six times, e.g., three times. In an exemplary method, 100 μg of a DNA composition is administered to a human subject at 0, 4, and 12 weeks (100 μg per administration).

Protein Compositions

Proteins, e.g., isolated proteins, encoding antigens of primary HIV isolates can be administered as "boosts" following vaccination with nucleic acid compositions. Recombinant proteins (e.g., proteins produced by cloning DNA encoding antigens of primary isolates using standard molecular biological techniques) can be one source of isolated proteins for boosting. Proteins used for boosting an individual can include the same sequences as encoded by the DNA vaccines previously administered to the individual, e.g., gp120, gp140, gp160, and/or gp41.

For large-scale production of recombinant HIV proteins, transfectant cell lines are generated (e.g., Chinese Hamster Ovary cell transfectants), and cell lines that stably express the HIV proteins are generated from the transfectants. Lines that overexpress the protein are selected for production. Master and working cell banks of selected cells are maintained. Proteins are expressed by growing cells in large-scale cultures in protein-free medium. Supernatants of the cells are harvested. Protein is then purified (e.g., using affinity chromatography, ion exchange chromatography, and/or gel filtration chromatography), and tested for purity. Proteins are purified and concentrated using techniques such as gel filtration and ion exchange chromatography. Next, proteins are evaluated for identity, potency, purity, quantity, sterility, the presence of endotoxin, and general safety according to Good Manufacturing Practice (GMP) guidelines. Identity can be determined with ELISA with antibodies specific for the lade of the protein. Potency can be evaluated with ELISA (e.g., reactivity of rabbit sera with the purified protein). Purity can be evaluated with SDS-PAGE and silver stain analyses of the protein, and size-exclusion high-performance liquid chromatography. Quantities can be determined by Coomassie-based assays, spectrophotometric assays, and volume measurements. The quality of protein preparations can be determined by visual inspection and pH measurements. Sterility can be determined by methods described in 21 C.F.R. 610.12. Endotoxin can be determined by Limulus Amebocyte assays. General safety can be determined by methods described in 21 C.F.R. 610.11.

Protein compositions containing an immunogenically effective amount of a recombinant HIV protein, or fragments thereof, can be administered. Suitable compositions can include, for example, lipopeptides (e.g., Vitiello et al., 1995, J. Clin. Invest., 95:341), peptide compositions encapsulated in poly(DL-lactide-co-glycolide) ("PLG") microspheres (see, e.g., Eldridge et al., 1991, Molec. Immunol., 28:287-94; Alonso et al., 1994, Vaccine, 12:299-306; Jones et al., 1995, Vaccine 13:675-81), and peptide compositions contained in immune stimulating complexes (ISCOMS) (see, e.g., Takahashi et al., 1990, Nature 344:873-75; Hu et al., 1998, Clin. Exp. Immunol. 113:235-43).

Useful carriers that can be used with the immunogenic compositions and vaccines described herein are well known, and include, for example, thyroglobulin, albumins such as human serum albumin, tetanus toxoid, polyamino acids such as poly L-lysine, poly L-glutamic acid, influenza, hepatitis B virus core protein, and the like. The compositions and vaccines can contain a physiologically tolerable (i.e., acceptable) diluent such as water, or saline, typically phosphate buffered saline. The compositions and vaccines also typically include an adjuvant. Adjuvants such as QS-21, incomplete Freund's adjuvant, aluminum phosphate, aluminum hydroxide, or alum, are examples of materials well known in the art. Additionally, CTL responses can be primed by conjugating S proteins (or fragments, derivative or analogs thereof) to lipids, such as tripalmitoyl-S-glycerylcysteinyl-seryl-serine ($P_3CSS$).

Administration of Protein Compositions

Immunization with a composition containing an HIV protein composition, e.g., via injection, aerosol, oral, transderrnal, transmucosal, intrapleural, intrathecal, or other suitable routes, induces the immune system of the host to respond to the composition. In one embodiment, a composition of Env proteins is administered. In one embodiment, a composition of Env and Gag proteins is administered.

An exemplary range for an immunogenic amount of protein composition is 5 μg/kg-500 μg/kg, e.g., 10-100 μg/kg of total protein, with adjuvant. In one embodiment, a dose of 325 μg of a protein composition is administered to a human (18-55 years of age, 45-75 kg). An exemplary program of administration of the protein composition includes a first intramuscular boost 8 weeks after the final nucleic acid immunization, followed by a second intramuscular boost with the protein composition 8 weeks after the first boost.

Kits

Kits comprising the nucleic acid and protein compositions are provided. The kits can include one or more other elements including: instructions for use; other reagents, e.g., a diluent, devices or other materials for preparing the composition for administration; pharmaceutically acceptable carriers; and devices or other materials for administration to a subject. Instructions for use can include instructions for therapeutic application (e.g., DNA vaccination and protein boosting) including suggested dosages and/or modes of administration, e.g., in a human subject, as described herein.

The kit can further contain at least one additional reagent, such as a diagnostic or therapeutic agent, e.g., a diagnostic agent to monitor a response to immune response to the compositions in the subject, or an additional therapeutic agent as described herein (see, e.g., "Combination Therapies," below).

In one embodiment, the kit includes a vial (or other suitable container) containing nucleic acids encoding two, three, four, five, or six distinct HIV Env gps. The kit also includes a second vial containing recombinant HIV Env gps that are the same Env gps as encoded by the nucleic acids in the kit. The kit can include QS-21 adjuvant (50 μg/dose/subject) and cyclodextrin as an excipient (30 mg/subject). The adjuvant and the excipient are formulated with the protein, and can be included in the formulation or packaged separately within the kit.

Combination Therapies

The nucleic acid and protein compositions described herein can be used in methods of treating subjects infected with HIV. The methods of treating these subjects with these compositions can include combination therapies, in which other HIV treatments are administered. For example, a subject undergoing DNA vaccination with protein boosting can be administered anti-retroviral drugs individually, or as Highly Active Antiretroviral Therapy ("HAART"), which refers to therapy with various combinations of nucleoside reverse transcriptase inhibitors, non-nucleoside reverse transcriptase inhibitors, and HIV protease inhibitors.

Nucleoside reverse transcriptase inhibitors include, e.g., zidovudine (AZT); didanosine (ddI); zalcitabine (ddC); stavudine (d4T); lamivudine (3TC); abacavir (1592U89); adefovir dipivoxil [bis(POM)-PMEA]; lobucavir (BMS-180194); and lodenosine (FddA), 9-(2,3-dideoxy-2-fluoro-b-D-threo-pentofuranosyl)adenine.

Non-nucleoside reverse transcriptase inhibitors include nevirapine (BI-RG-587); delaviradine (BHAP, U-90152); and efavirenz (DMP-266).

Protease inhibitors include saquinavir (Ro 31-8959); ritonavir (ABT-538); indinavir (MK-639); nelfnavir (AG-1343) available under the VIRACEPT™ tradename from Agouron Pharmaceuticals, Inc.; amprenavir (141 W94), a non-peptide protease inhibitor, tradename AGENERASE™; and lasinavir (BMS-234475).

The new nucleic acid and protein compositions described herein can enhance the effectiveness of any known AIDS therapies, e.g., by reducing the HIV viral load in the infected patient. The compositions and methods described herein can be used as an adjuct therapy to enhance an infected individual's immune response against the virus.

Evaluating Immune Responses to Vaccinations and Protein Boosts

Advances in the field of immunology have allowed more thorough and sensitive evaluations of cellular responses to candidate HIV vaccines. Such assays as intracellular staining (e.g., flow cytometry) and ELISPOT (an enzyrne-linked immunosorbent assay format), allow detecting and counting cells producing cytokines (e.g., TNFα and IFN-γ) in response to antigens. For example, isolation of splenocytes or peripheral blood monocyte cells (PBMCs) from animals or human patients followed by in vitro challenge with HIV epitope such as V3, and finally testing by ELISPOT and/or intracellular cytokine staining (ICS), can determine the potential for a cell-mediated immune response in vaccine recipients. Flow cytometry using tetramers (i.e., molecules consisting of four copies of a given class I molecule bound to their cognate peptide and alkaline phosphatase) allows the enumeration of antigen-specific T cells (e.g., detection of T cells that recognize specific peptides bound to major histocompatibility complex (MHC) class I molecules). A standard chromium release assay can be used to assess cytotoxicity. To assess a cell-mediated immune response to a DNA vaccine, the more traditional approaches of measuring T cell proliferation in response to antigen and CTL-mediated killing of autologous cells expressing HIV epitopes can also be used.

ELISA assays and Western blots can be used to assess humoral immune responses. In particular, ELISA and Western blots can be used to assess antibody binding, antibody neutralizing capability, antibody-mediated fusion inhibition, and antibody-dependent cytotoxicity.

MT-2 Assay—An MT-2 assay can be performed to measure neutralizing antibody responses. Antibody-mediated neutralization of HIV-1 IIIB and MN (a B-clade laboratory strain) can be measured in an MT-2 cell-killing assay as described previously (Montefiori et al., 1988, J. Clin. Microbiol., 26:231-237). HIV-1IIIB and MN induce the formation of syncytia in MT-2 T cells. The inhibition of the formation of syncytia by the sera shows the activity of neutralizing antibodies present within the sera, induced by vaccination. Briefly, vaccinated test and control sera can be exposed to virally infected cells (e.g., MT-2 T cell line). Neutralization can be measured by staining viable cells (e.g., with Finter's neutral red when cytopathic effects in control wells are about >70% but less than 100%). Percentage protection can be determined by calculating the difference in absorption ($A_{540}$) between test wells (cells+virus) and dividing this result by the difference in absorption between cell control wells (cells only) and virus control wells (virus only). Neutralizing titers are then expressed as the reciprocal of the plasma dilution required to protect at least 50% of cells from virus-induced killing.

cleavable gp140 with the intact natural cleavage site between gp120 and gp41, were PCR amplified from 9 different primary Env genes representing 7 genetic clades, A to G, of HIV-1 group M (Table 1). A pair of consensus PCR primers was designed and used to amplify nine different gp120 genes: a plus strand primer GP120-p-f1 (p-cttgtgggtcacagtctattatggggtacc) (SEQ ID NO:1) and a minus strand primer GP120-p-b1 (ggtcggatccttactccaccactcttctctttgcc) (SEQ ID NO:2). The consensus primers for amplifying gp140 genes were GP120-p-f1 for plus strand and JAPCR502 (cgacggatccttatgttatgtcaaaccaattccac) (SEQ ID NO:3) for minus strand.

The PCR products with the designed blunt-end at the 5' was further digested by BamHI at the 3' end, and cloned into DNA vaccine vector pJW4303 (Chapman, et al., 1991, Nucleic Acids Res 19:3979-3986; Lu et al., 1996, J Virology 70:3978-3991; Lu et al., 1998, AIDS Res and Hum Retroviruses 14:151-155). The vector pJW4303 was first digested with NheI, followed by treatment with Klenow fragment to blunt the end and then cut again with BamHI. The NheI site was regenerated after ligation with the Env inserts, which are in-frame with the tissue plasminogen activator (tPA) leader sequence in pJW4303.

The DNA vaccine plasmids were named as pJW4303/gp120 or pJW4303/gp140.A1, A2, B, C1, C2, D, E, F and G respectively (Table 1). Table 1 shows useful polyvalent vaccine components, the strain and Genebank Accession number from which they were derived, the genetic lade, and the country of origin. For soluble gp41 (sgp41) DNA vaccines, consensus primers GP41-P-F1 (gtcgctccgctagcgcagtgggaatag-gagctgtgttccttgggttc) (SEQ ID NO:4) and JAPCR502 were used to amplify sgp41 genes, which were cloned into pJW4303 NheI and BamHI sites. For a given polyvalent vaccine, any combination of the two or more of the components listed in Table 1 can be used. The polyvalent vaccine can be administered as naked DNA plasmid, with a facilitating agent, with an adjuvant, and/or with a protein boost described herein.

TABLE 1

Polyvalent HIV-1 envelope glycoprotein DNA vaccine components

| Polyvalent gp120 DNA vaccine components | Polyvalent gp140 DNA vaccine components | Polyvalent gp41 DNA vaccine components | HIV-1 strains | Genetic clades | Geographic regions | GeneBank Accession number |
|---|---|---|---|---|---|---|
| gp120.A1 | gp140.A1 | sgp41.A1 | 92RW020.5 | A | Africa | U08794 |
| gp120.A2 | gp140.A2 | sgp41.A2 | 92UG037.8 | A | Africa | U09127 |
| gp120.B | gp140.B | sgp41.B | 92US715.6 | B | North America | U08451 |
| gp120.C1 | gp140.C1 | sgp41.C1 | 92BR025.9 | C | South America | U09126 |
| gp120.C2 | gp140.C2 | sgp41.C2 | 93MW965.26 | C | Africa | U08455 |
| gp120.D | gp140.D | sgp41.D | 92UG021.16 | D | Africa | U27399 |
| gp120.E | gp140.E | sgp41.E | 93TH976.17 | E | Asia | U08458 |
| gp120.F | gp140.F | sgp41.F | 93BR020.17 | F | South America | U27401 |
| gp120.G | gp140.G | sgp41.G | 92UG975.10 | G | Africa | U27426 |

EXAMPLES

The invention is further described in the following examples, which do not limit the scope of the invention described in the claims.

Example 1

Construction of HIV-1 Envelope Glycoproteins gp120, gp140, and gp41 DNA Vaccines from Clade A-G Primary Isolates The gene fragments encoding the extracellular portion of HIV-1 primary Env gps, either in the form of gp120 or as a

Example 2

Immune Response Raised by HIV-1 Primary Isolate DNA Vaccine

DNA Immunization. A female New Zealand Rabbit (2 kg) received three monthly DNA immunizations by gene gun. Each shot delivered 1 μg of DNA and a total of 36 non-overlapping shots were delivered to each rabbit at each of the three time points at the surface of shaved abdominal skin after animals were anesthetized according to IACUC approved protocols. The serum samples were collected immediately before, and 4 weeks after each immunization.

ELISA (enzyme-linked immunosorbent assay). Rabbit sera samples were tested for gp120-specific IgG antibody responses by ELISA. Microtiter plates were coated with ConA (5 μg per well) for 1 hour and then washed 5 times with washing buffer (PBS at pH 7.2 with 0.1% Triton X-100). Env antigens at 1 μg/ml were added (100 μl for each well) and incubated for 1 hour at room temperature. Blocking was done with 200 μl/well of 4% milk-whey blocking buffer for 1 hour at room temperature. After removal of the blocking buffer and another 5 time washes, 100 μl of serially diluted sera were added and incubated for 1 hour. The plates were washed 5 times and incubated with 100 μl of biotinylated anti-rabbit IgG diluted at 1:1000 for 1 hour followed with washes. Then, horseradish peroxidase-conjugated streptavidin diluted at 1:2000 was added (100 μl/well) and incubated for 1 hour. After the final washes, 100 μl of fresh TMB substrate was added per well and incubated for 3.5 min. The reaction was stopped by adding 25 μl of 2 M $H_2SO_4$, and the optical density (OD) of the plate was measured at 450 nm. ELISA assays in which sera reactivity to gp120 was evaluated are described in examples below.

Western blot analysis. The gp120 antigens transiently expressed from 293T-cell supernatants and cell lysates were subjected to denaturing SDS-PAGE and blotted onto polyvinylidene fluoride (PVDF) membrane. Blocking was done with 0.1% I-Block. Rabbit serum immunized with mixed polyvalent gp120 DNA vaccines was used as the detecting antibody at 1:500 dilution and incubated for 45 minutes. Subsequently, the membranes were washed with blocking buffer and then reacted with AP-conjugated goat anti-rabbit or human IgG at 1:5000 dilution. After final wash, Western-light substrate was applied to the membranes for 5 minutes. Once the membranes were dry, Kodak films were exposed to the membrane and developed with an X-Omat processor. Env reactivity was also observed by Western blot.

Example 3

Neutralization Assay

One way of determining the potential efficacy of a vaccine in animals is to perform in vitro functional assays of the animal's immune cells. The peripheral blood mononuclear cell (PBMC) assay and the MT-2 assay described above are examples of evaluating humoral responses in vaccinated test animals in vitro. As described below, cell-mediated immune responses can also be tested to evaluate the functional ability of immune cells of vaccinated animals. These assays can also be performed in vitro with immune cells isolated from human subjects in determining the potential efficacy of a vaccine.

PBMC Assay. The presence of neutralizing antibodies in the serum of a vaccinated animal was tested in a functional assay referred to as a neutralization assay. Rabbits were immunized as described in example 2, above, with a monovalent vaccine (rows 3-10) or polyvalent vaccine (row 11). The left column designates with which primary isolate vaccine the rabbit was vaccinated. The sera, collected four weeks after the third immunization, were applied to peripheral blood monocyte cells (PBMCs) infected with different primary viral isolates (designated in the top row). Table 2 shows the results of this PBMC neutralization assay of monovalent and polyvalent immunization and immunization of rabbits. Results from this assay are expressed as percent inhibition of virus as compared with the virus control without immunized rabbit sera. Results from the monovalent vaccinations show a general trend towards the ability to autologously respond. However, as seen in the last row, in which the polyvalent vaccine was used, greater than 57% inhibition against any of the tested primary viral isolates virus was obtained showing that the polyvalent primary HIV-1 Env vaccine was able to generate broad neutralizing antibody responses in the rabbits receiving this vaccine.

TABLE 2

Neutralization Assay Results

| | PBMC with primary isolates | | | |
|---|---|---|---|---|
| Rabbit sera | A1 | B | C1 | E |
| A1 | <10 | 38% | 100% | <10 |
| A2 | 99% | <10 | 5% | 96% |
| B | <10 | 94% | 24% | <10 |
| C1 | <10 | <10 | <10 | <10 |
| C2 | <10 | <10 | 100% | <10 |
| D | <10 | 97% | 100% | <10 |
| E | 32% | 58% | 13% | 93% |
| F | 27% | 56% | 36% | 37% |
| G | <10 | 0% | 1% | <10 |
| A to G | 78% | 57% | 60% | 97% |

Example 4

Assaying Protective Immunity

The efficacy of the new DNA vaccines can be tested in an animal model. Preferably, responses in animals that can be infected by HIV are tested, such as a non-human primate (e.g., a chimpanzee) or an animal, such as a mouse, which has circulating human immune cells. Large enough numbers of animals should be used to achieve statistical significance, though in the case of non-human primates, the numbers may be limited and thus the experiments may be repeated in the same animal for example. Once the test animals are vaccinated and control animals are vaccinated with a negative control containing the same vector, but without the heterologous Env gp DNA, both groups of animals can then be infected with HIV. They may be infected with primary isolates or with laboratory strains, or both. After a suitable amount of time to allow infection with HIV and at which the animals vaccinated with negative control vaccine begin to show a decline in T cell number, then the test and control animals can be tested for protective immune response.

One way to test a protective immune response is to obtain sera from the animals and use ELISA (see above) to test for the presence of specific IgG antibody responses (see Example 2 above). The animals can be monitored for the presence, delay or absence of HIV infection relative to negative control animals, using methods known in the art.

Efficacy of a vaccine can be evaluated in uninfected animals by performing in vitro functional assays on the immune cells of the vaccinated animal. The presence of neutralizing antibody can be tested in vaccinated animals (e.g., mice, rats, rabbits, non-human primates), which have not been infected with HIV. This neutralization assay is described above in Example 3. Cell-mediated immune responses (e.g., CTL) responses can be tested in animals (e.g., mouse or non-human primate) without infection with HIV. To test a cell-mediated immune response, splenocytes can be isolated. The splenocytes are then exposed to the peptide antigen V3, a commonly used HIV antigen that provides a good epitope to test ability of T cells to mount a cell-mediated immune response in vitro. ELISPOT and/or Intracellular Cytokine Staining (ICS) are then performed to determine T cell function. Other tests for ability to resist infection can be performed which are known in the art. Although the best test of protection against HIV is to challenge that animal with HIV, currently there is no definitive way to infect a non-human animal with HIV. SHIV infection of non-human primates has been tested. The current standard of testing in animals to test vaccination is, as discussed, isolation of immune cells of a vaccinated animal and functional testing for activity against antigen such as V3, for example, or generation of neutralizing antibody.

Experiments in which DNA vaccines and protein boosts are tested are described below.

Example 5

Anti-gp120 DNA Vaccination and Boosting in Rabbits

DNA and protein compositions were prepared with antigens listed in Table 3. The antigens were administered to rabbits according to the study design presented in FIG. 1. Briefly, rabbits were immunized with monovalent, 3-valent, 8-valent, or control DNA vaccines at 0, 4, 8, and 16 weeks as listed in FIG. 1. Animals received protein boosts at week 24 and 28 as depicted in FIG. 1. Neutralization of primary HIV-1 isolates by sera from immunized animals was measured. Neutralization titers for sera collected after the last DNA immunization (and before the first protein immunization) are depicted in FIG. 2. Neutralization titers for sera collected after the first protein immunization are depicted in FIG. 3. Percentages of neutralization for sera (1:5 dilution) collected after the second protein immunization are depicted in FIG. 4. Titers are calculated based on the dilution of immune serum inhibiting 50% of infection as compared to untreated controls. The lower rows of each table under "positive antibodies" list neutralization values obtained with antibodies HIVIG, 2F5, and 2G12, which are known to neutralize in these assays. Sera measurements showing a high level of neutralizing activity are shaded in each figures. FIG. 2 shows that monovalent and polyvalent DNA vaccination resulted in high levels ($50\%^{+}$) of neutralizing activity against clade B isolate SF162.

Neutralizing activity to other clade B, C, A, and E isolates was also detected. FIG. 3 shows that DNA vaccination with one protein boost induced high levels of neutralizing activity against clade B SF162, Ba-L, and JRCSF isolates, with low levels of activity against other isolates. Activity was observed in all of the animals receiving polyvalent and approximately half of the animals receiving monovalent vaccination. Both monovalent and polyvalent regimes produced responses with high levels of activity in some animals. FIG. 4 shows that the second boost resulted in high neutralizing activity in all animals, with varying degrees of responsiveness to different isolates.

Figures 5A, 5B, 5C:
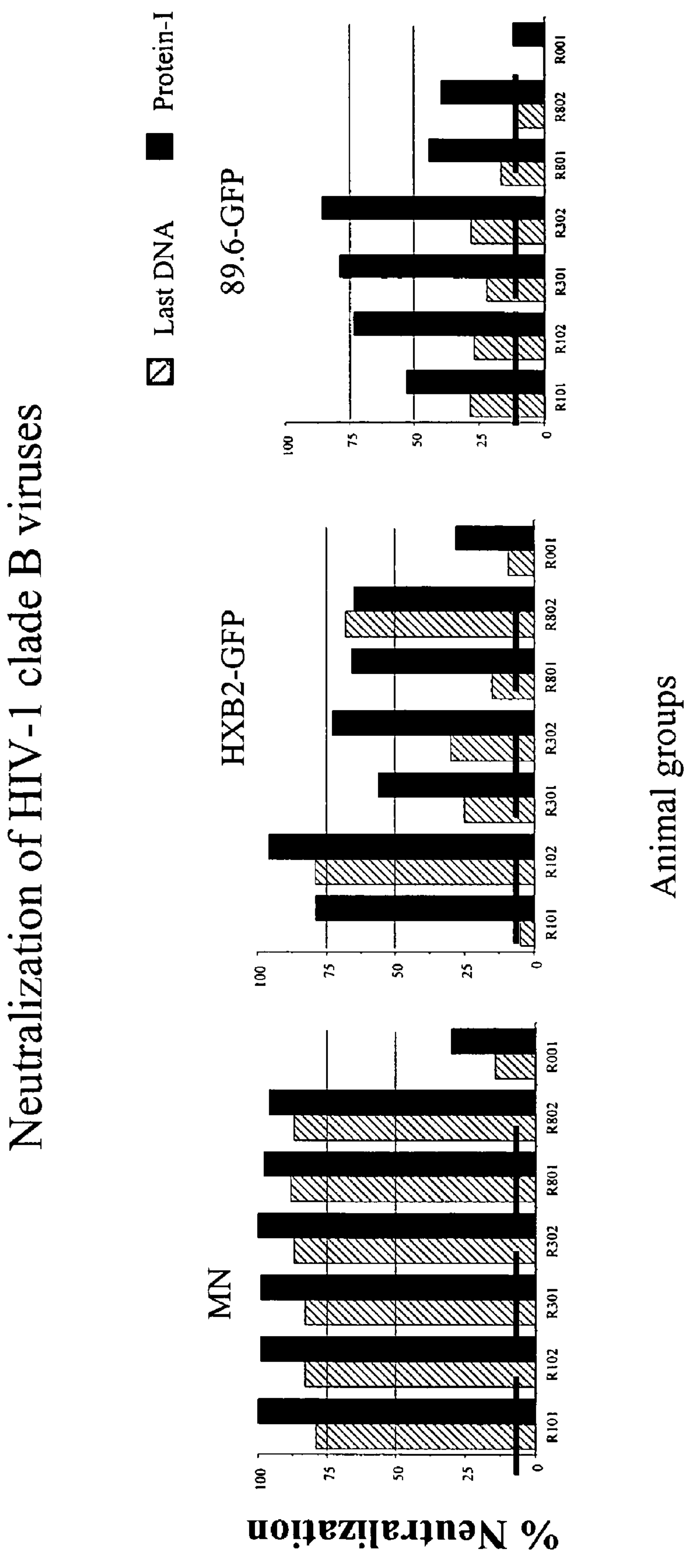
FIGS. 5A-5C is a set of graphs depicting percent neutralization by sera from rabbits immunized with monovalent and polyvalent vaccines. "Last DNA" corresponds to assays for sera taken after the last DNA immunization. "Protein-I" corresponds to assays for sera taken after the first protein immunization.

Neutralizing responses were tested against additional clade B viruses (MN, HXB2-GFP, and 89.6 GFP). Construction of viruses expressing green fluorescent protein (GFP) is described in Example 9, below. FIG. 5A, B, and C, shows % neutralization observed for sera from the animals listed in the table in FIG. 1. Sera taken from animals after DNA vaccination and after one protein boost shows that high levels of neutralizing activity were induced against isolate MN in animals receiving both monovalent and polyvalent DNA. Neutralizing activity against HXB2 and 89.6 isolates was lower, but high levels were achieved in some animals with protein boosting. Monoclonal antibodies 2F5 and 2G12 neutralized with high levels (75%) of neutralizing activity against those strains in this assay (data not shown).

TABLE 3 gp120 Immunogens used in DNA Vaccination and Protein Boosting Studies in Rabbits

| gp120 immunogen | Genetic subtype | HIV-1 strain | Co-receptor usage | GenBank ® Accession No. |
|---|---|---|---|---|
| A-120 | A | 92UG037.8 | CCR5 | U09127 |
| B-120* | B | 92US715.6 | CCR5 | U08451 |
| C1-120* | C | 92BR025.9 | CCR5 | U09126 |
| D-120 | D | 92UG021.16 | CXCR4 | U27399 |
| E-120* | EA | 93TH976.17 | CCR5 | U08458 |
| F-120 | F | 93BR020.17 | CXCR4 | U27401 |
| G-120 | G | 92UG975.10 | CCR5 | U27426 |
| Ba-L-120* | B | Ba-L | CCR5 | M68893 |

Example 6

An HIV-1 Gag DNA Vaccine is Immunogenic in Mice

Cell mediated immune (CMI) responses elicited by Codon optimized Gag DNA vaccines with or without tPA leader sequence were examined.

Balb/C mice (female) were immunized using a gene gun to evaluate the immunogenicity of DNA vaccines. This vaccine included a codon optimized, gag gene insert from the HIV-1 isolate Czm. Each animal received 4 monthly immunizations with 6 μg of DNA delivered at each immunization. One week after the last immunization, animals were sacrificed and spleens were collected for analysis of CMI responses. This study compared the relative immunogenicity of two different constructs with a Gag gene insert (Table 4). One construct (.wt) used a codon optimized gag gene sequence without any additional modification on the coding amino acids. The other (.tPA) codes for an additional human tissue plasminogen leader sequence (tPA) at the very N-terminus end. The tPA leader was reported to be responsible for improved expression and immunogenicity of Gag DNA vaccines (Qiu, et al., 2000, J. Virology. 74(13):5997-6005). However, in our previous studies using non-codon optimized gag gene from a laboratory adapted HIV-1 isolate (IIIB), it was found that the wild type gag gene insert was more immunogenic than the gag gene insert with a tPA leader in inducing CMI responses. This study was undertaken to investigate whether the codon optimized gag gene inserts from HIV primary isolate 96ZM651 (Czm) would show similar findings. CMI responses elicited by these vaccines were analyzed by ELISPOT assays and intracellular cytokine (IFNγ) staining (ICS) with an imunodominant peptide from Gag p24 antigen stimulation.

Both ELISPOT and intracellular cytokine staining (ICS) methods were used to measure the cell mediated immune responses. The results are shown in Table 4. Animals that received either of the two gag DNA vaccines all showed Gag specific CMI responses, as shown by both ELISPOT and ICS data. The vector alone groups did not show significant Gag-specific CMI responses. The wild type gag insert appeared slightly more immunogenic than the gag insert with a tPA leader.

TABLE 4

Average Gag-specific Cell-Mediated Immune Responses in Mice Immunized with Gag DNA Vaccines

| Animal groups | No. of animals per group | ELISPOT: Gag peptide* specific spots/million cells | ICS: Gag peptide* specific IFN expressing CD8+ T cells (%) |
|---|---|---|---|
| pSW3891 vector | 5 | 4.25 ± 4.34 | 0.2 ± 0.03 |
| pSW3891/Gag.Czm.Opt.wt | 4 | 1020 ± 470.31 | 3.74 ± 2.59 |
| pSW3891/Gag.Czm.Opt.tPA | 4 | 604 ± 538.63 | 2.29 ± 2.87 |

*Gag p24 peptide (199-207): AMQMLKDTI; Reference peptide sequence, p24 (aa 65-73)

Thus, the codon optimized Czm gag insert was highly immunogenic in the pSW3891 vector, and it was more immunogenic when expressed with its natural N-terminal sequences than with a tPA leader sequence. This is the design of the construct used in DP6-001.

Example 7

Monovalent and 4-valent Env Vaccines Induce Anti-HIV-1 Env IgG Responses in Rabbits The immunogenecity of HIV-1 Env DNA vaccine as either monovalent or 4-valent formulations was examined. In this study, New Zealand White (NZW) rabbits (female) were immunized with DNA vaccines expressing primary HIV-1 Env antigens. Each group included two (Groups 10, 11, 14 and 17) or three rabbits (Groups 1 and 3). Each animal recieved four monthly DNA immunizations with 36 μg of total DNA plasmid (36 μg of single DNA for the monovalent group and 9 μg of each DNA for the 4-valent group) delivered by a gene gun (Bio-Rad) at each immunization. In this study, non-codon optimized DNA vaccines were used. Sera collected two weeks after the last DNA immunization were measured by ELISA for the levels of anti-Env IgG responses. ELISA plates were coated with recombinant primary Env antigens. The starting serum dilution was 1:500 in these experiments.

ELISA data on NZW rabbit sera induced by either one HIV-1 Env DNA vaccine component (monovalent) or a combination of four Env DNA vaccine components (4-valent) is summarized in Table 5. While the monovalent sera in general had higher titers against the respective autologous Env antigens than the heterologous Env antigens, the 4-valent DNA vaccine was able to generate a high titer antibody against a broad spectrum of primary HIV Evn antigens, including both homologous (such B, Ba-L, Czm and E) and heterologous antigens (such as A2, D, F and G).

Thus, DNA immunization was effective in inducing high titer anti-Env antibody responses with both monovalent and polyvalent vaccine formulations. Polyvalent formulations were able to induce a higher level of antibody responses against multiple primary HIV-1 Env antigens than the monovalent formulation.

TABLE 5

End Point Titration Titers of Anti-Env IgG of Rabbit Sera

| NZW Rabbit Groups | DNA Vaccines Used for Rabbit Immunization | Env Antigens Coated for ELISA Plates: Ba-L | B | C | E | A2 | D | F | G |
|---|---|---|---|---|---|---|---|---|---|
| 1 | Ba-L | 233,644 | 54,000 | 112,325 | 54,000 | 162,000 | 77,881 | 25,960 | 77,881 |
| 11 | B | 54,000 | 324,000 | 162,000 | 54,000 | 54,000 | 54,000 | 54,000 | 36,000 |
| 14 | Czm | 12,000 | 36,000 | 486,000 | 108,000 | 108,000 | 54,000 | 54,000 | 36,000 |
| 3 | E | 54,000 | 12,481 | 112,325 | 486,000 | 77,881 | 37,442 | 112,325 | 112,325 |
| 17 | B, Ba-L, Czm, E | 972,000 | 324,000 | 162,000 | 486,000 | 486,000 | 108,000 | 324,000 | 324,000 |
| 10 | vector | <500 | <500 | <500 | <500 | <500 | <500 | <500 | <500 |

Example 8

Anti-HIV-1 Env IgG Responses for 3-valent and 8-valent DNA+Protein Vaccination

The immunogenicity of polyvalent Env DNA+protein vaccines in rabbits was evaluated. New Zealand White rabbits (female) were immunized with DNA vaccines expressing primary HIV-1 Env antigens. Each group included three rabbits. Each animal received four monthly DNA immunizations with 36 μg of DNA plasmid (12 μg of each DNA for 3-valent group and 4.5 μg of each DNA for 8 valent group) delivered by a gene gun (Bio-Rad) at each immunization. In this study, non-codon optimized DNA vaccines were used.

After two months rest, two monthly protein boosts were administered subcutaneously in Freud's incomplete adjuvant (IFA). The protein boosts matched the DNA priming with the gp120 antigens from the same primary viral isolates (Table 6). Each rabbit received a total of 100 μg of recombinant gp120 proteins for each protein boost (33.3 μg of each protein in Group C4 and 25 μg of each protein in Group C7).

TABLE 6

| Design of Animal Groups for DNA Prime + Protein Boost | | | |
|---|---|---|---|
| Animal Groups | Animal Numbers | DNA Priming Components | Protein Boosting Components |
| C4 | C4-1, C4-2, C4-3 | B, C1, E | B, C1, E |
| C7 | C7-1, C7-2, C7-3 | Ba-L, B, C1, E, A, D, F and G | B, C1, E, Ba-L |

Sera collected two weeks after the last DNA immunization and after each protein boost were measured by ELISA for the levels of anti-Env IgG responses.

Figure 6:
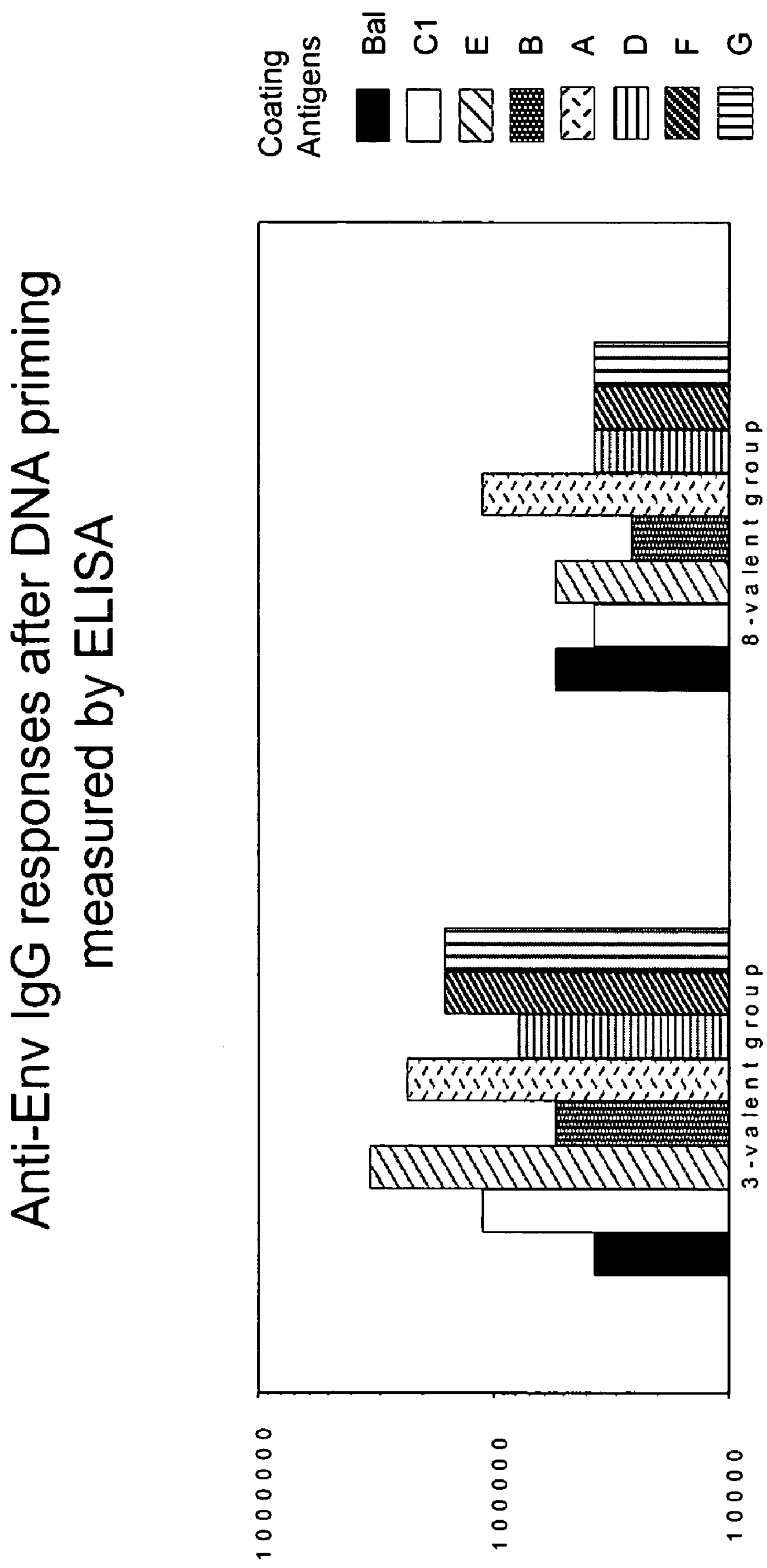
FIG. 6 is a bar graph depicting end titration titers of anti-env IgG responses after DNA priming, as measured by ELISA. ELISA plates were coated with the different primary gp120 antigens as indicated (Ba-L, C1, E, B, A, D, F, or G).

To measure anti-Env responses, different primary gp120 antigens were coated individually on the ELISA plates as indicated (Ba-L, C1, E, B, A, D, F or G). ELISA data on NZW rabbit sera induced by either three HIV-1 Env DNA vaccine component (3-valent, B, C1 and E) or eight Env DNA vaccine components (8-valent, B, C1, E, Ba-L, A, D, F and G) are summarized in FIG. 6. Both 3-valent and 8-valent DNA formulations induced high titer antibody responses against primary HIV-1 Env antigens. The 3-valent formulation elicited high titer antibody responses against both homologous (such B, C1 and E) and heterologous Env antigens (such as Ba-L, A, D, F and G). Under the conditions used, the 8-valent formulation did not appear to improve this immune response.

Figures 7A, 7B, 7C, 7D, 7E, 7F:
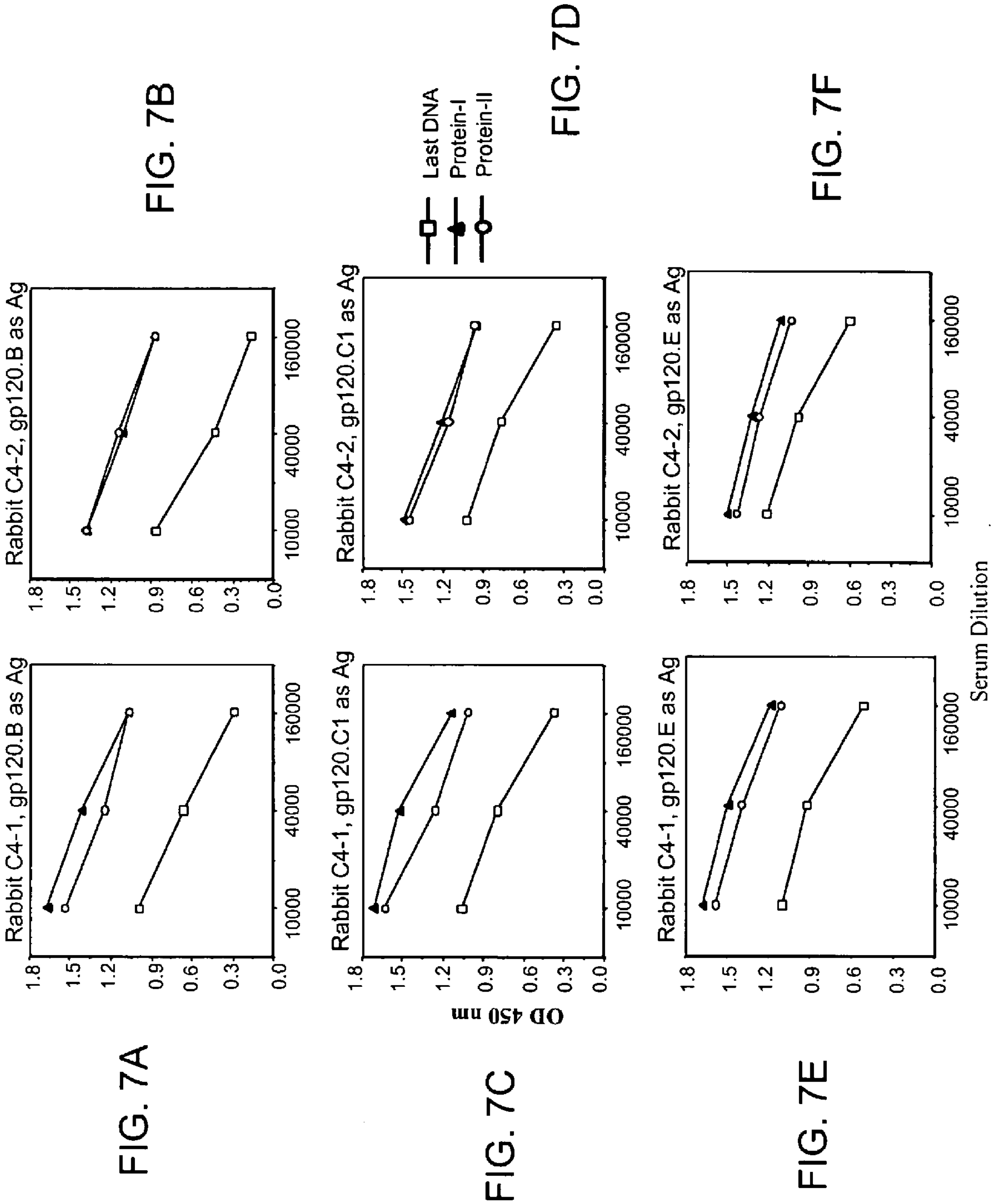
FIGS. 7A-F are graphs depicting anti-gp120 antibody responses after DNA priming and protein boost in 3-valent gp120 vaccine immunized animal group C4. "Last DNA" refers to sera collected after the $4^{th}$ DNA immunization. "Protein I" refers to sera collected after one protein boost. "Protein II" refers to sera collected after two protein boosts. Data for sera from rabbits immunized with B, C1, and E DNAs, and boosted with B, C1, and E proteins are presented.

Anti-Env IgG response after protein boosts in animals which received 3-valent Env DNA vaccine formulation were measured (FIG. 7). In this study, three sera dilutions were tested: 1:10,000; 1:40,000 and 1:160,000. In the "Last DNA" group, sera were collected after the fourth DNA immunization. In the "Protein I" group, sera were collected after one protein boost. In the "Protein II" group, sera were collected after two protein boost. After one protein boost (Protein-I), anti-Env IgG responses in rabbits primed with the same DNA vaccines quickly reached the peak level. The second protein boost (Protein-II) did not increase the response in this experiment. This was true for all three Env antigens (B, C1 and E) tested in this ELISA study.

Figures 8A, 8B, 8C, 8D, 8E, 8F, 8G, 8H:
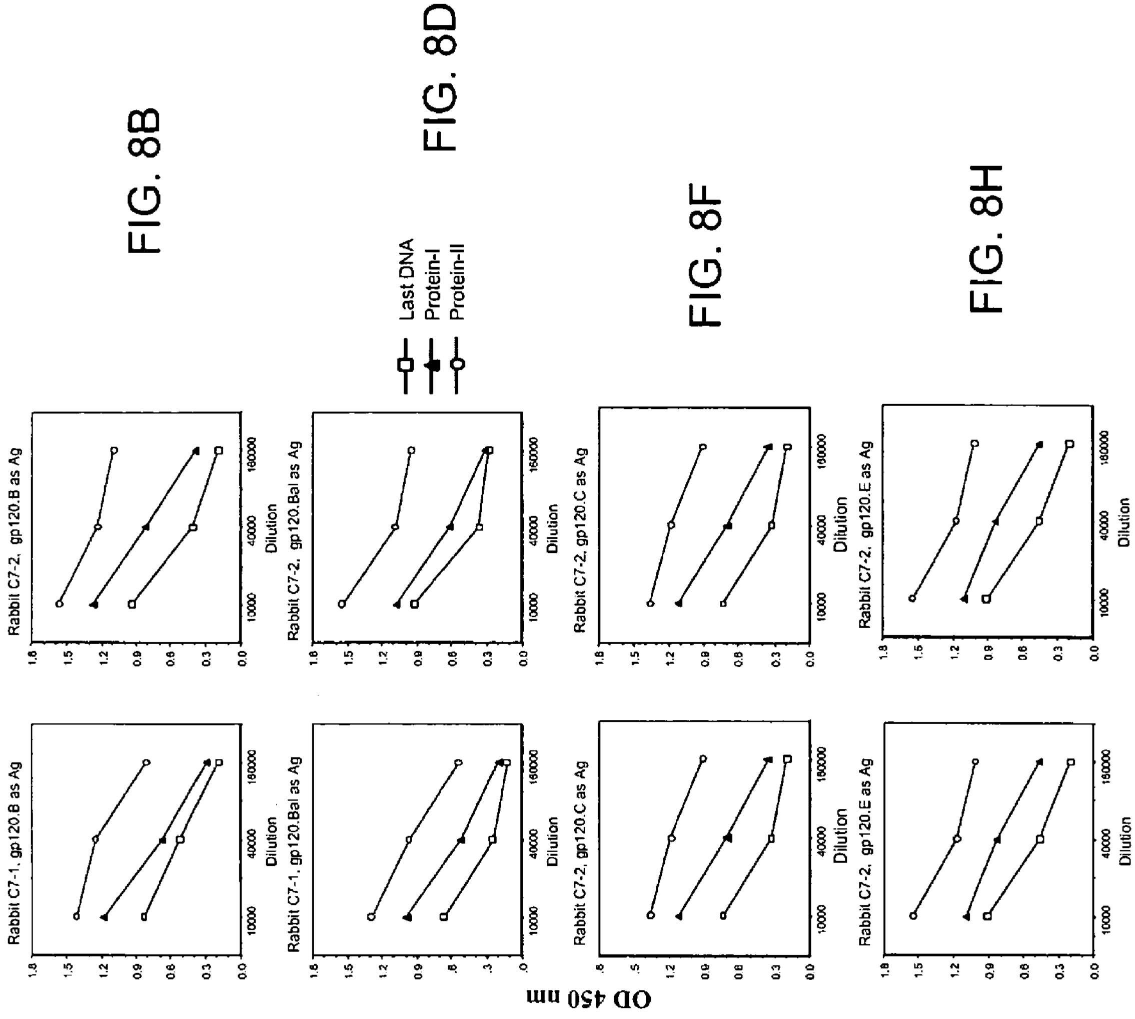
Figures 8I, 8J, 8K, 8L, 8M, 8N, 8O, 8P:
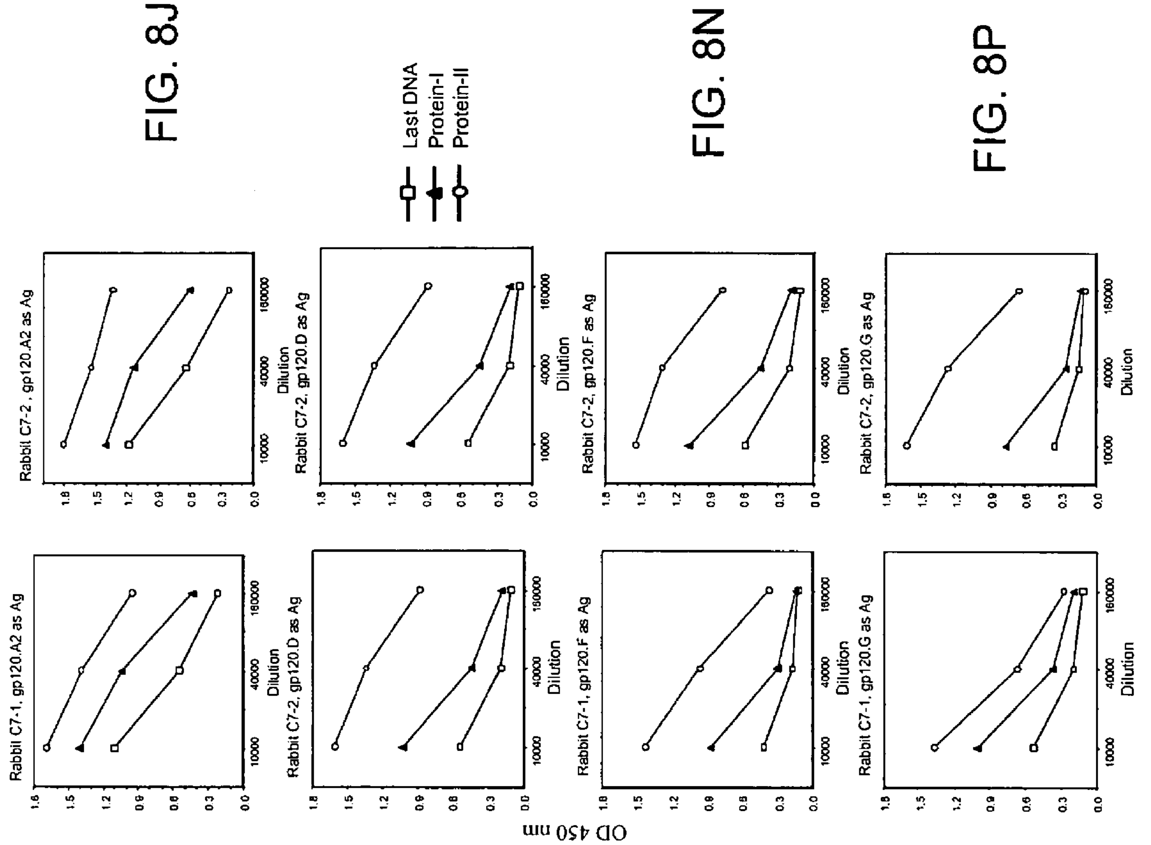

However, for animals that received 8-valent Env DNA vaccines, two protein boosts were usually required for anti-Env IgG to reach the same level as found in the 3-valent group. The data in FIG. 8A depict the rabbit IgG responses against primary Env antigens included in both DNA prime and protein boost immunizations. The data in FIG. 8B depict the IgG responses against primary Env antigens that were included only in the DNA priming phase. The patterns were very similar between the groups. Two proteins were needed to induce a higher level of anti-Env IgG responses.

These data show that DNA immunization with a 3-valent HIV-1 Env formulation induced an effective immune response against gp20 from homologous and some heterologous strains of HIV-1. This response was not improved with the use of an 8-valent formulation, under the conditions used for these studies. Recombinant HIV-1 Env proteins were very effective in boosting the anti-ENV responses in all DNA-primed animals. One protein boost was needed to reach peak antibody levels in animals receiving 3-valent DNA priming while two protein boosts were needed with the 8-valent group to reach the same peak levels. In DP6-001, five primary Env DNA vaccines are included in the priming phase to cover at least 4 clades of HIV-1 Env antigens without compromising the immunogenicity of DNA priming. Two protein boosts are proposed in DP6-001 to maximize the boosting effect.

Example 9

Neutralizing Antibody Responses with Rabbit Sera Immunized with Monovalent and Polyvalent Env DNA+Protein Formulations The neutralizing antibody responses elicited by DNA prime+protein boost vaccine regiment against multiple primary HIV-1 isolates was examined. As shown in Table 7, each animal received 4 monthly DNA immunizations (DNA priming) and two monthly protein boosts at varying individual dose as described below. For mono-valent and 3-valent groups, the protein boosts matched the DNA priming with the same primary gp120 antigens. The monovalent group (Group C1) received gp120.Ba-L, a primary HIV-1 Env antigen. The 3-valent group (Group C4) received three primary HIV-1 Env antigens: gp120-B, gp120-C1 and gp120-E. For 8-valent group (Group C7), animals received DNA vaccines expressing eight primary HIV-1 Env antigens: gp120.A, gp120-B, gp120-Ba-L, gp120-C, gp120-D, gp120-E, gp120-F and gp120-G followed by the protein boosts including 4 recombinant gp120 antigens: gp120-B, gp120-Ba-L, gp120-C and gp120-E. Group C10 is a control group in which rabbits were first inoculated four times with the empty DNA vector pSW3891, followed with protein boost of a mixture of four Env protein antigens (same as Group 7). In this pre-clinical study, the env genes inserted in the DNA vaccines were not codon optimized.

TABLE 7

| Design of Animal Groups for HIV-1 Neutralizing Antibody Responses | | | |
|---|---|---|---|
| Animal Groups | Animal Numbers | gp120 DNA Priming Components | gp120 Protein Boosting Components |
| C1 | C1-1B, C1-2B | Ba-L | Ba-L |
| C11 | C11-1, C11-2 | B | B |
| C2 | C2-1, C2-1 | C1 | C1 |
| C3 | C3-1, C3-2 | E | E |
| C4 | C4-1, C4-2 | B, C1, E | B, C1, E |
| C7 | C7-1, C7-2 | Ba-L, B, C1, E, A, D, F and G | B, C1, E, Ba-L |
| C10 | C10-1 | Vector control | B, C1, E, Ba-L |

Rabbit sera from animals described in Table 7 were collected at pre-immunization, after the fourth DNA immunization, and after the first and second protein boosts. Neutralization assays were conducted to examine whether rabbit sera with positive anti-Env IgG antibody responses could neutralize primary HIV-1 isolates. The neutralization activity of each serum was tested at 1:5 dilution using a green fluorescent protein (GFP) indicator assay system.

Recombinant green fluorescent protein (GFP) reporter viruses for use in the neutralization assays were generated by co-transfection of 293T cells with the pNL4-3env-plasmid (full-length NL4-3 HIV-1 proviral DNA with a frameshift in env and encoding GFP in place of nef) and the pSVIIIenv plasmid, encoding the clade B 89.6 Env protein. Supernatant containing reporter virus was collected 48 hrs after transfection, clarified by centrifugation and 0.45 μm filtration, and stored at −80° C. before use. To perform the assays, human PBMC were incubated with reporter virus in the presence or absence of antibody. The neutralizing antibody responses were measured by the percent reduction of GFP positive human PBMC as compared to the numbers in controls with pre-immunization serum.

Figure 9:
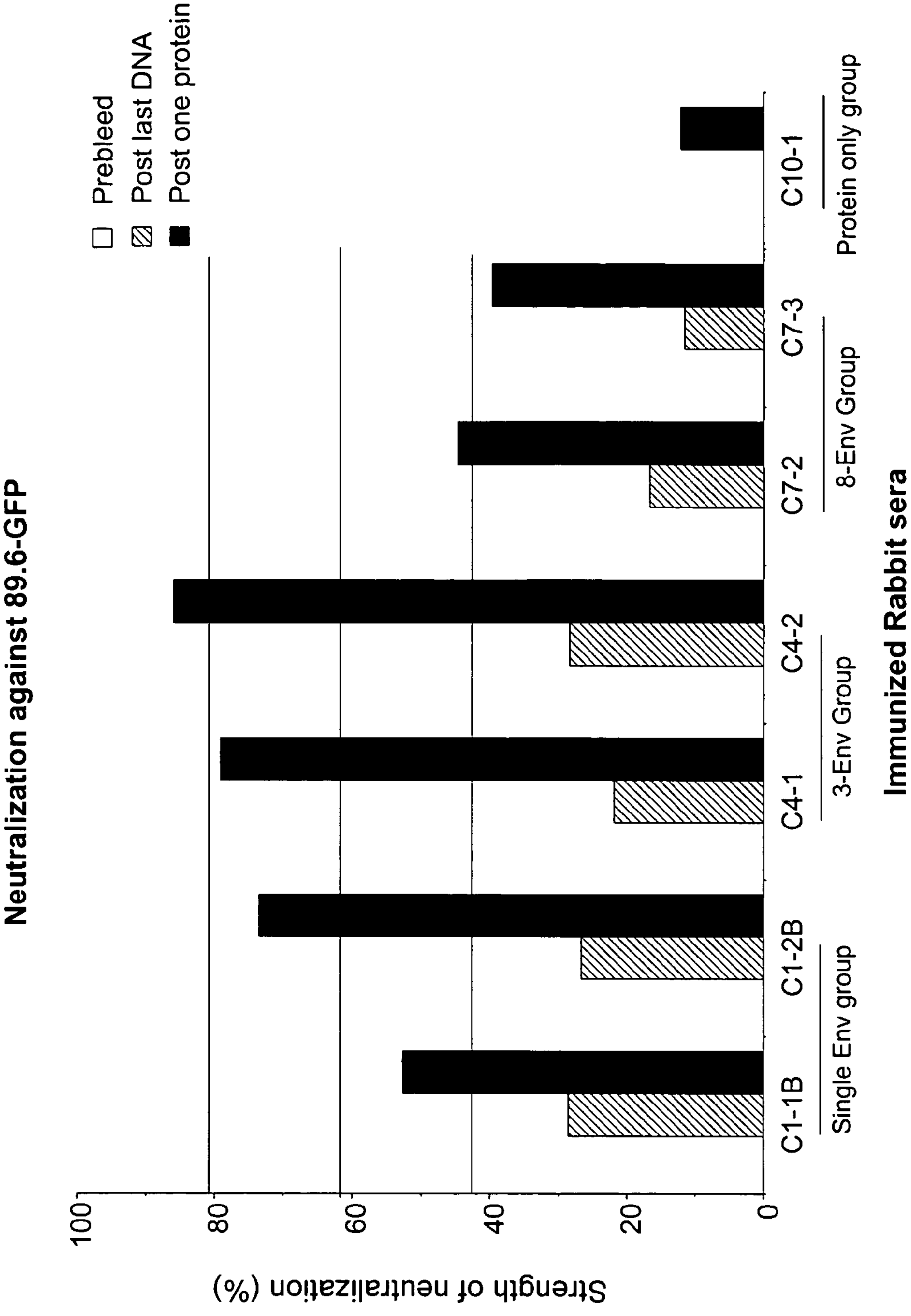
FIG. 9 is a graph depicting percent neutralization against HIV-1 89.6-GFP reporter virus with rabbit sera obtained before immunization, after DNA immunization, and after one protein boost. Each group of animals was immunized with a different gp120 formulation as indicated.

One set of neutralization data is depicted in FIG. 9. The strength of neutralizing antibody was ranked at three levels: high (above 80% reduction in GFP positive human PBMC), moderate (above 60% reduction) and low (above 40% reduction). The DNA+protein vaccination approach was highly effective in inducing neutralizing antibody responses against virus expressing Env-GFP of isolate 89.6, a primary HIV-1 virus. All animals except the control animal produced low levels of neutralizing antibody after the DNA vaccination and prior to the protein administration. One animal that received a monovalent vaccination produced low (approximately 50%) levels of neutralizing antibody. A second animal in the monovalent group produced moderate (approximately 75%) levels. Animals that received the 3-valent vaccination produced antibody with high or nearly high (approximately 78%) levels of neutralization. The 8-valent group produced low levels of approximately 40% neutralization. The control rabbit (C 10-1), which received a single Env protein immunization after four inoculations of empty DNA vector produced no detectable neutralizing antibody after DNA vaccination, and demonstrates a very low (approximately 10%) neutralizing antibody response after protein administration.

Further analyses of these rabbit sera against additional primary clade B HIV-1 viruses also showed positive neutralizing activities (FIG. 10 to 15). FIGS. 9 to 12 show that the DNA prime/protein boost approach using polyvalent formulation was highly effective in inducing neutralizing antibody responses against a number of primary HIV-1 clade B isolates. In these assays, neutralizing antibody responses were measured by the percent reduction of p24 positive PBMC as compared to the numbers in control with pre-immunization serum by a FACS based assay (Mascola, et al., 2002 J. Virol. 76, 4810-4821).

Figure 10:
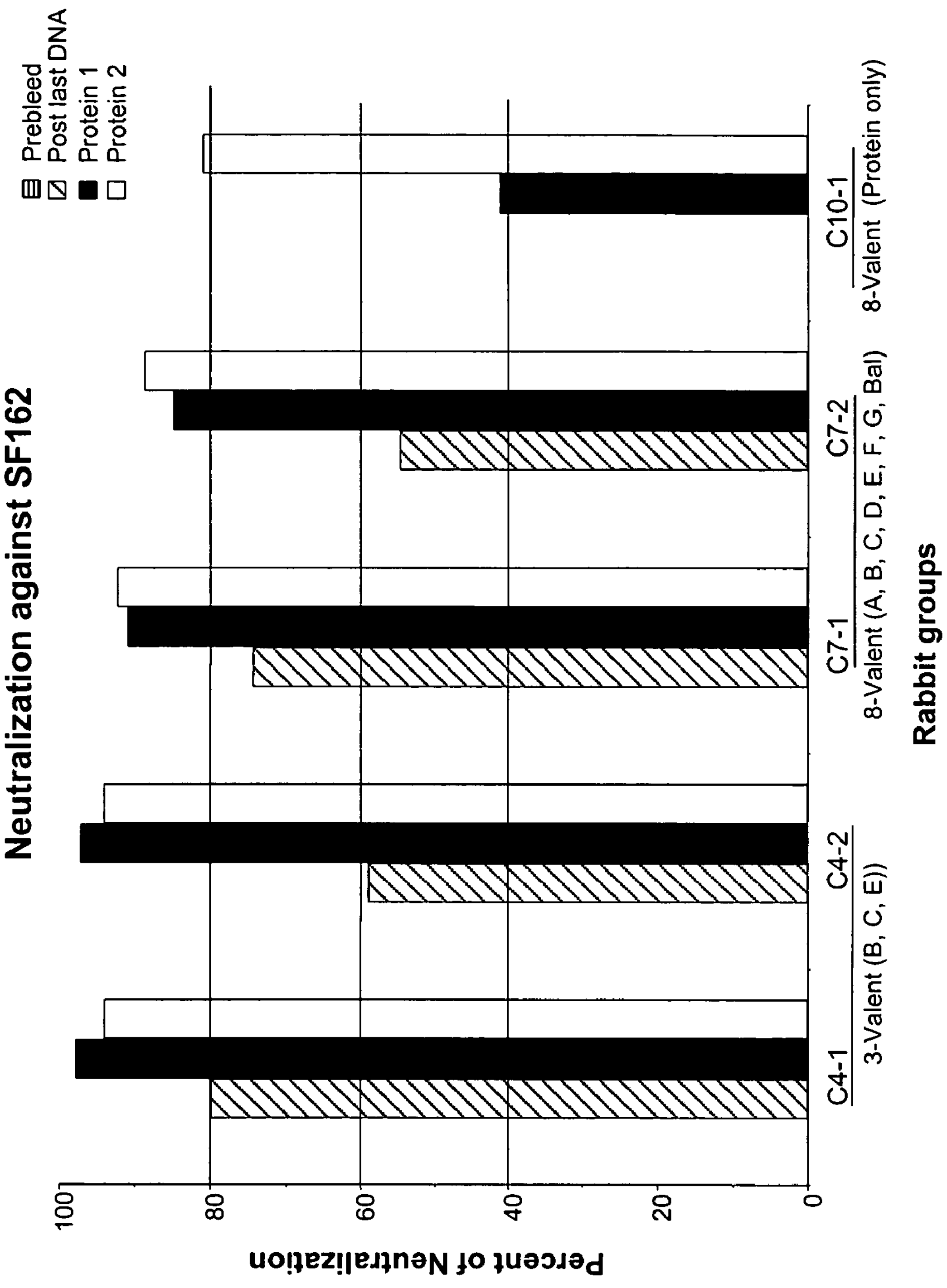
FIG. 10 is a graph depicting percent neutralization against HIV-1 SF162 with rabbit sera obtained before immunization, after DNA immunization, after one protein boost, and after two protein boosts. Each group of animals was immunized with a different gp120 formulation as indicated.

As shown in FIG. 10, significant levels of neutralizing antibody responses were present at the end of DNA priming. Sera from mice that received the 3-valent and 8-valent DNA+protein vaccination protocols exhibited high ($80\%^{+}$) levels of neutralizing activity toward the primary HIV-1 isolate, SF162, after one and two protein boosts. Peak levels of neutralizing activity were reached after the first protein boost. High levels of neutralizing activity were obtained in sera of the animal receiving two boosts of an 8-valent protein vaccination (without DNA vaccination).

Figure 11:
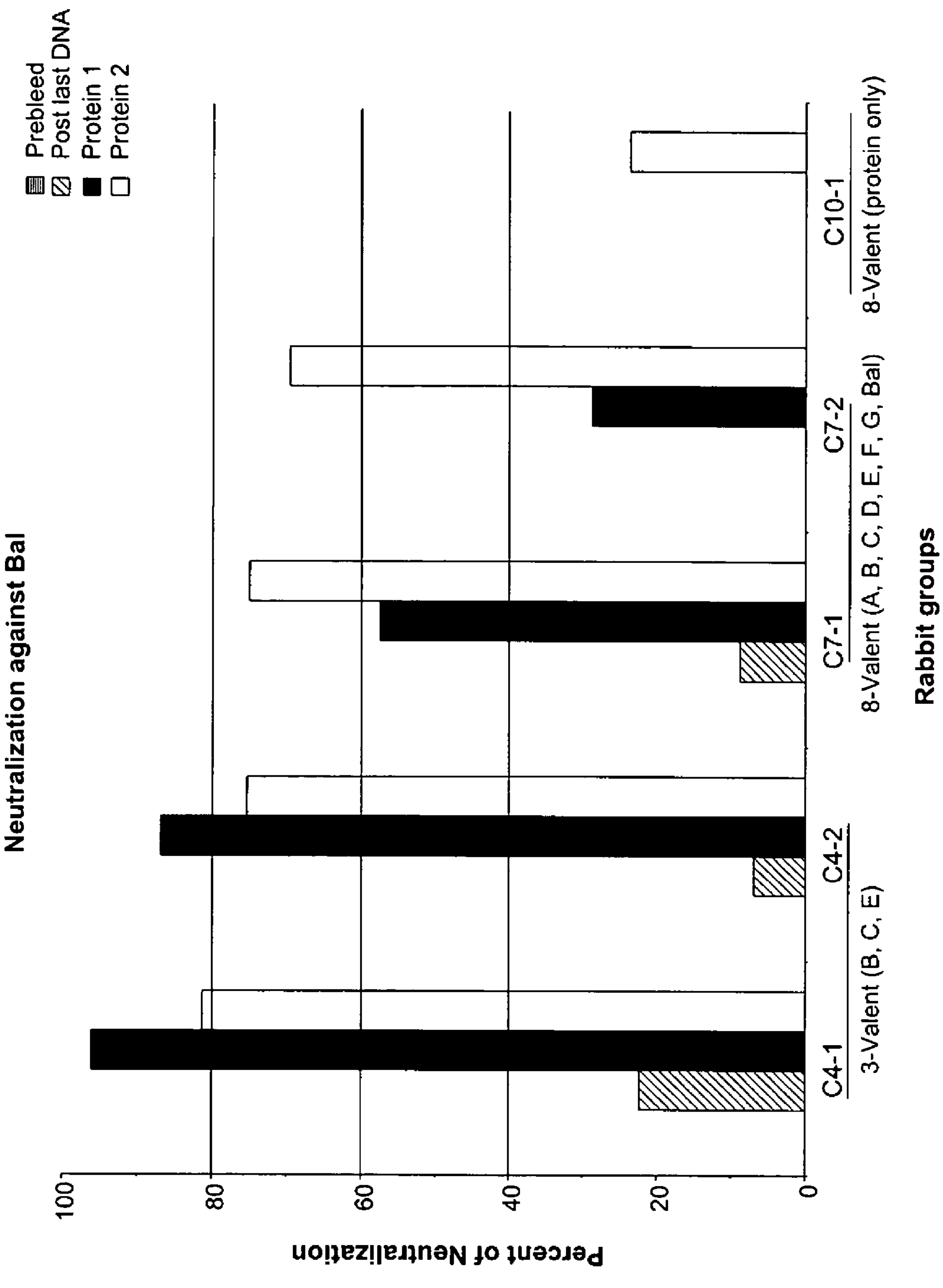
FIG. 11 is a graph depicting percent neutralization against HIV-1 Ba-L with rabbit sera obtained before immunization, after DNA immunization, after one protein boost, and after two protein boosts. Each group of animals was immunized with a different gp120 formulation as indicated.
Figure 12:
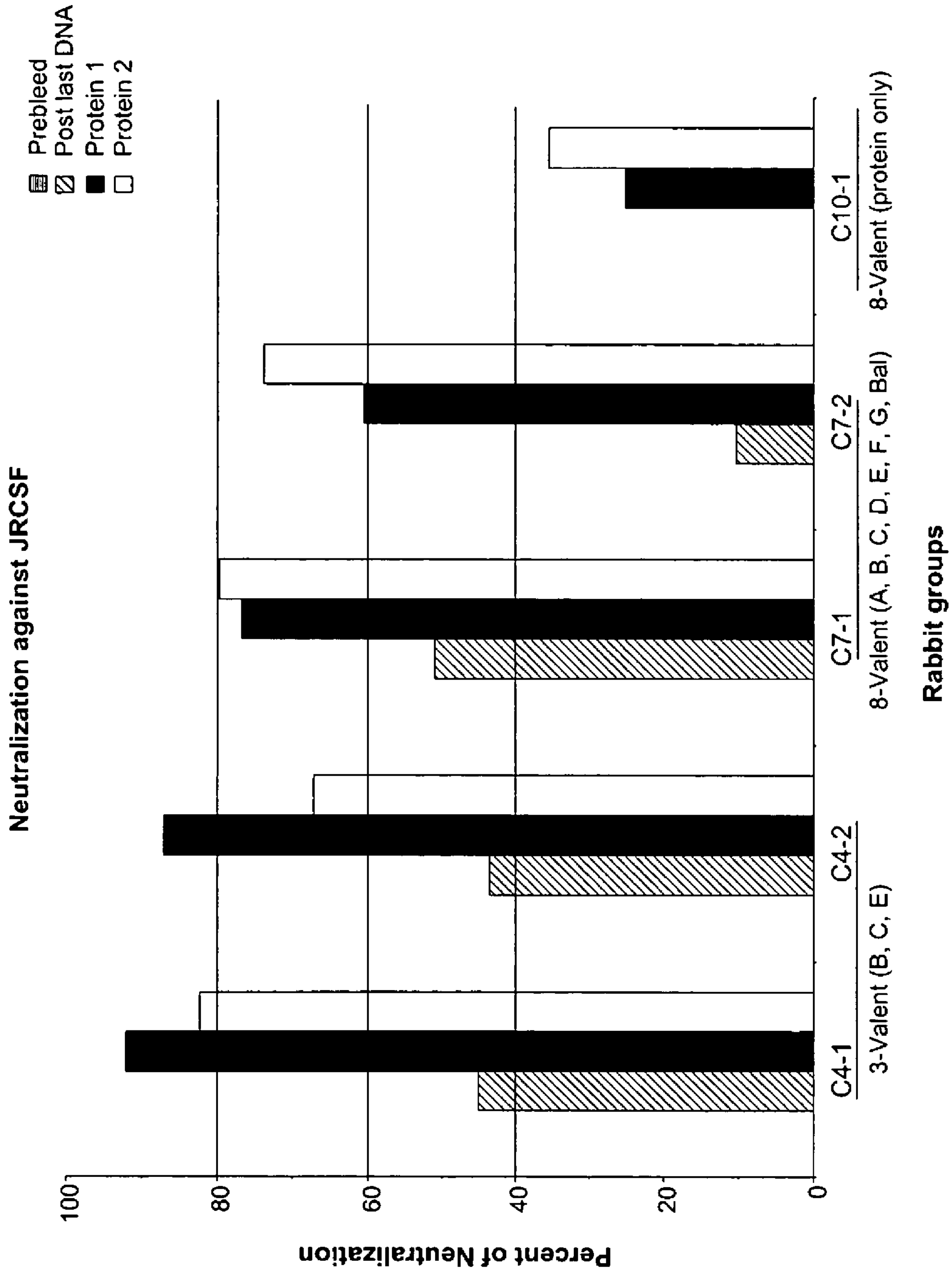
FIG. 12 is a graph depicting percent neutralization against HIV-1 JRCSF with rabbit sera obtained before immunization, after DNA immunization, after one protein boost, and after two protein boosts. Each group of animals was immunized with a different gp120 formulation as indicated.
Figure 13A:
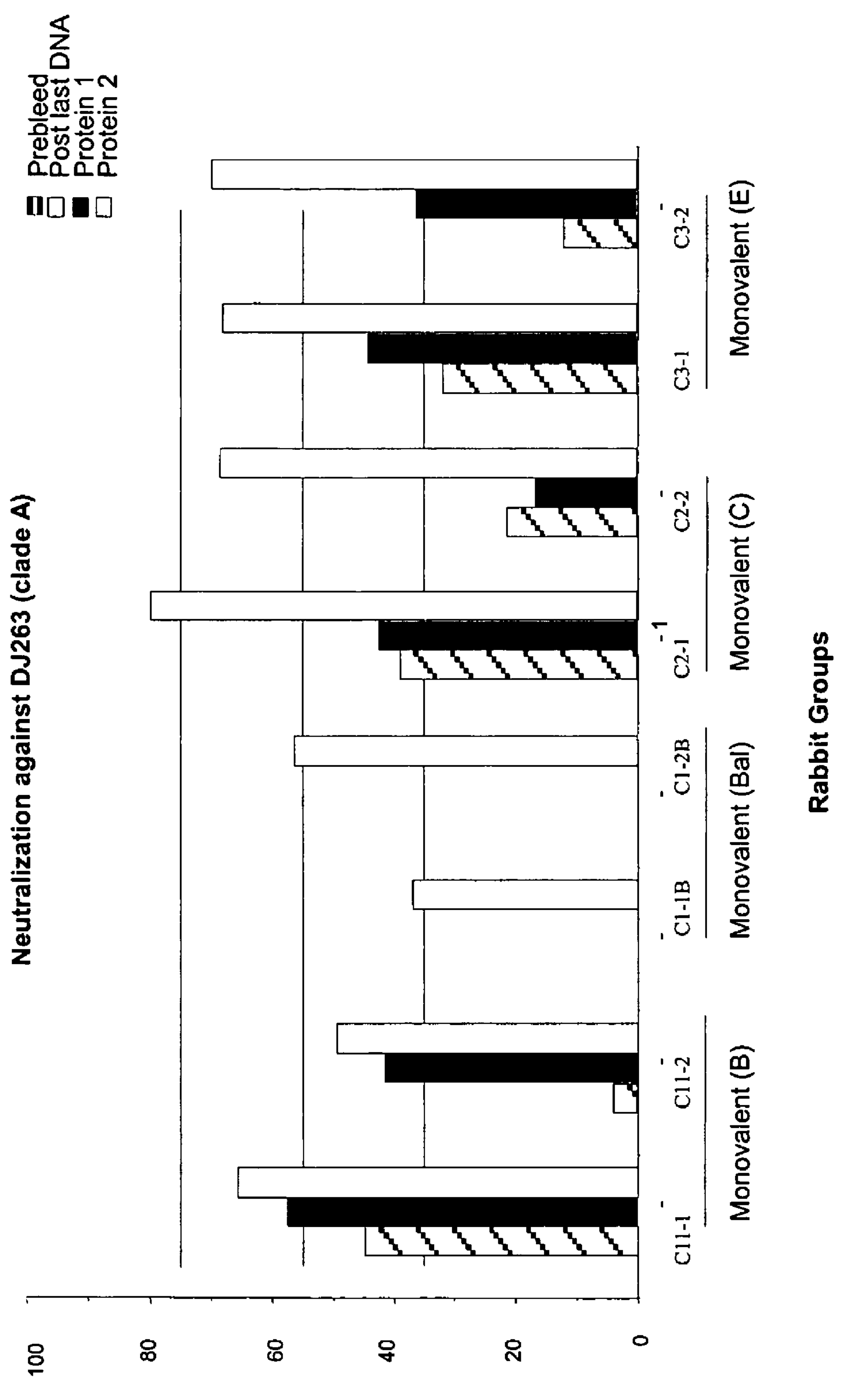
FIGS. 13A-D are a set of graphs depicting percent neutralization of HIV-1 lade A primary isolate DJ263 (FIGS. 8A and 8D) and clade C primary isolate TV1 (FIGS. 8B and 8C) with rabbit sera after DNA priming and protein boost. Each group of animals was immunized with a different gp120 formulation as indicated.
Figure 13B:
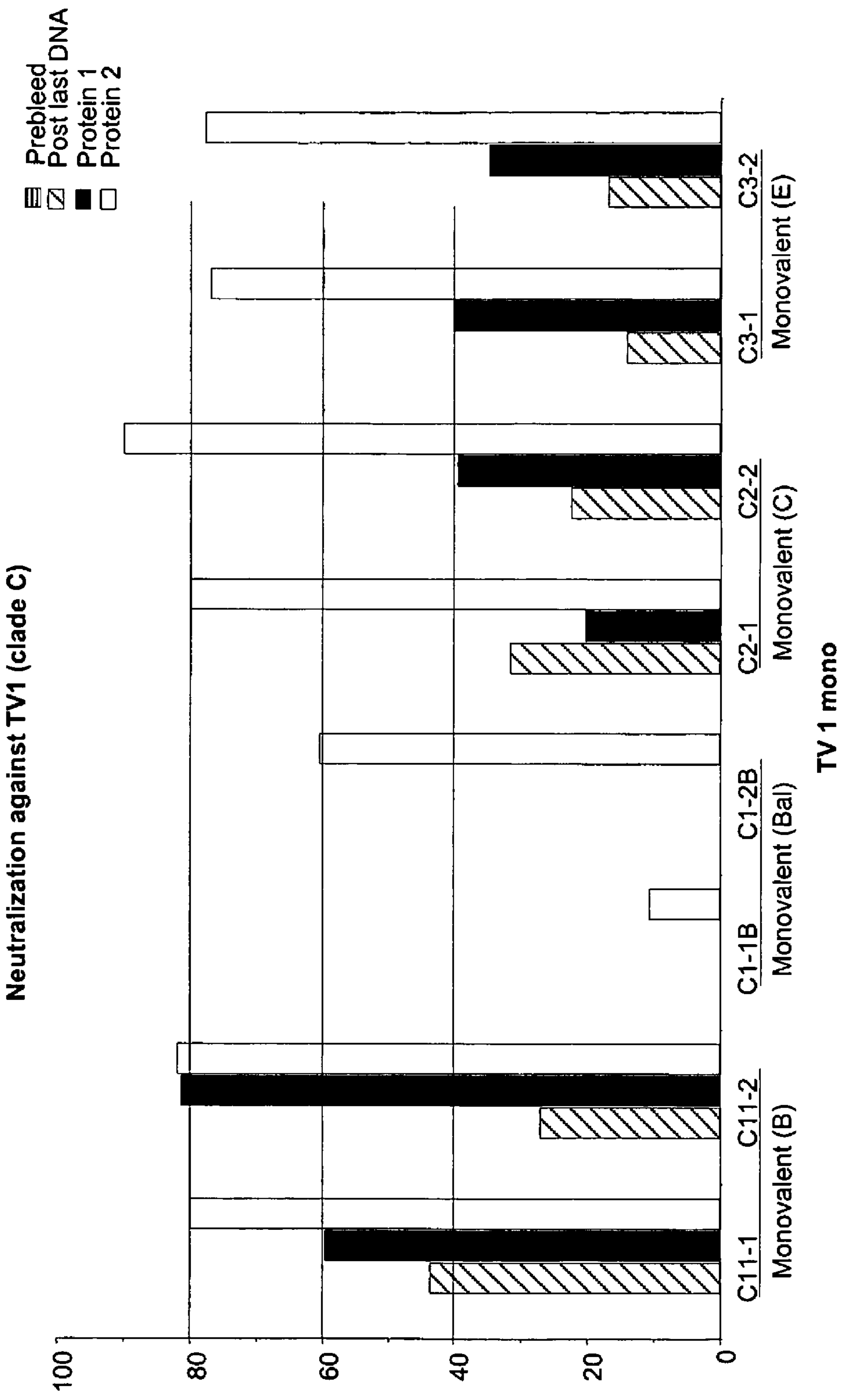
Figure 13C:
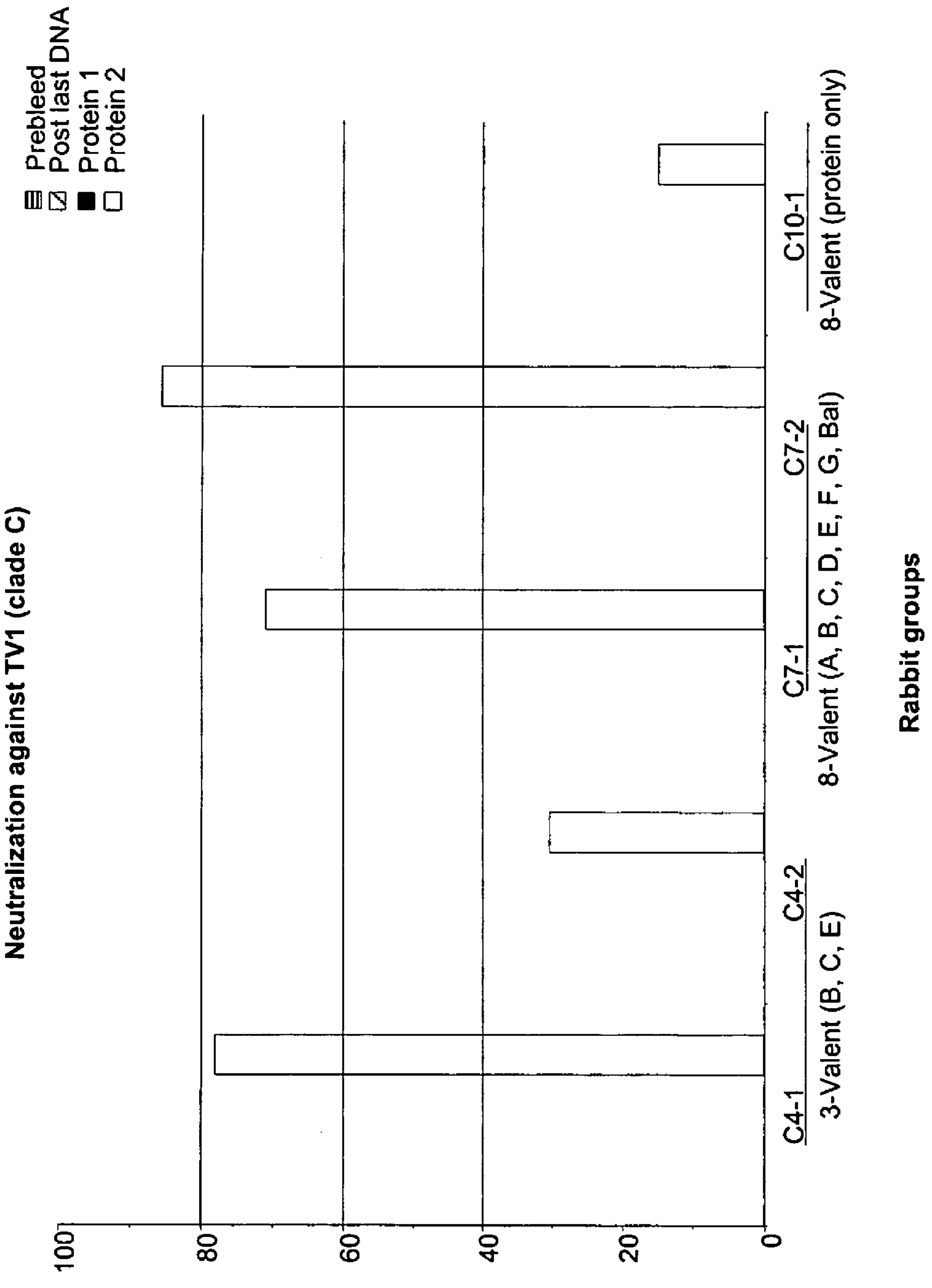
Figure 13D:
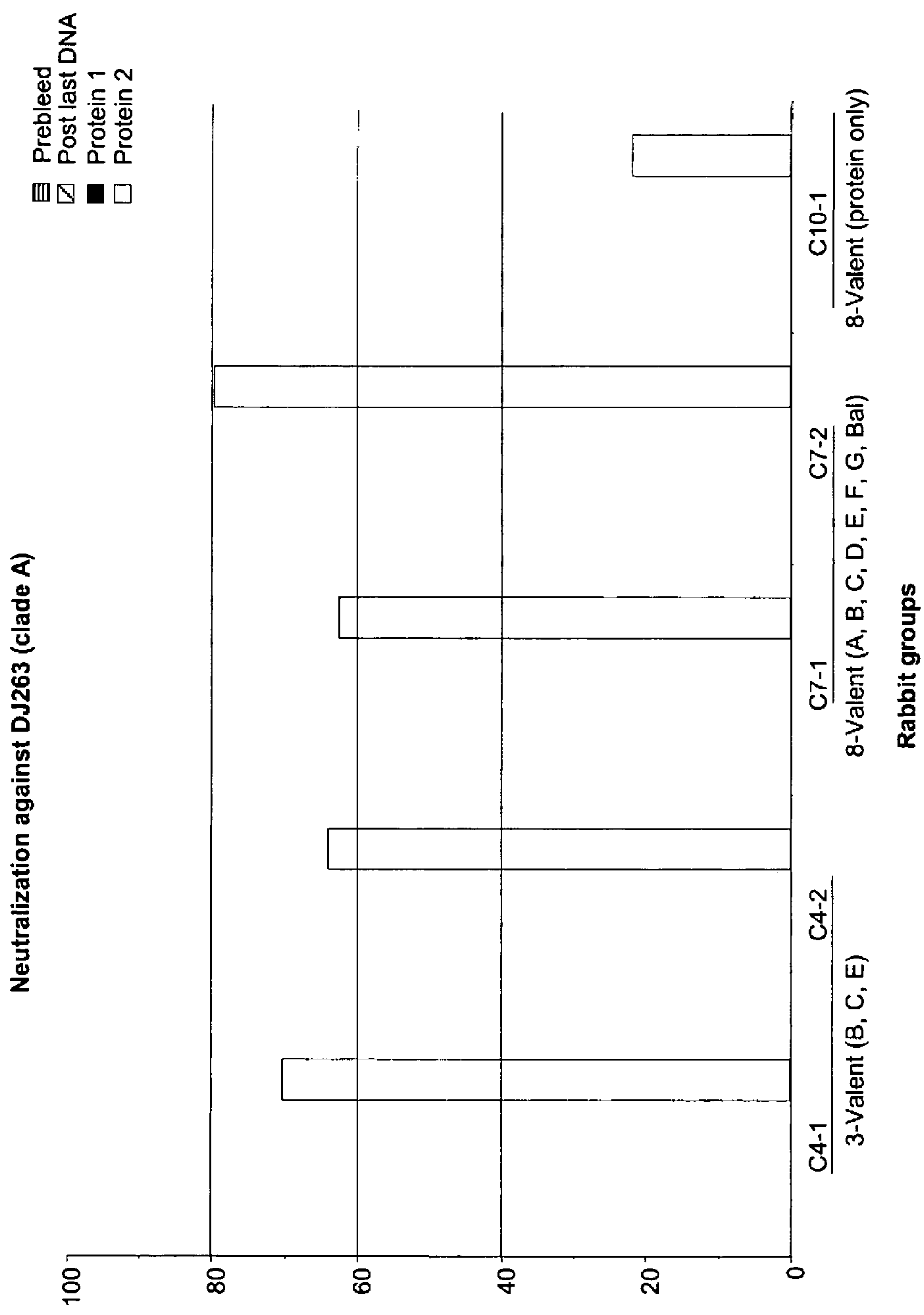

For Ba-L (FIG. 11) and JRCSF (FIG. 12), protein boosts were effective in generating higher levels of neutralizing activities than with DNA priming alone. As shown in FIGS. 11 and 12 high levels of neutralizing activity to primary HIV-1 strain Ba-L and JRCSF, respectively, were obtained in animals receiving the 3-valent vaccination protocol. The 8-valent group showed levels of approximately 60-80% after two protein boosts. With the conditions used, an 8-valent env DNA formulation did not result in a more robust antibody response than that elicited by the 3-valent formulation. It took one protein boost for the 3-valent group to reach the peak neutralizing antibody level while a second protein boost was needed for the 8-valent group. This finding is consistent with the solid phase binding antibody analysis results as shown in the examples below.

Serum from the control animal, 10-1, did not show any neutralizing activity after DNA priming. This animal only received empty DNA vector. However, the serum did show some low level neutralizing activities after one or two protein boosts. The levels of neutralizing activity were much lower than the DNA+protein approach, supporting the observation that DNA priming is very useful for the rapid induction of neutralizing antibody responses by 1-2 protein boosts, especially against the primary HIV-1 isolates, which are often difficult to neutralize.

Additional neutralization assays were conducted to examine whether these rabbit sera also neutralized primary viral isolates representing other HIV-1 clades. FIG. 13 shows data obtained after the second protein boost in animals receiving monovalent and polyvalent injections. After two protein boosts, several immunized rabbit sera (dilution 1:5) showed positive neutralizing activities against HIV-1 DJ263 (clade A) and TV1 (clade C) subtypes. In summary, these data show that the DNA prime/protein boost vaccination modality was effective in inducing neutralizing antibody responses against primary HIV-1 isolates across several subtypes.

Example 10

Rabbit Anti-Env IgG Responses with Codon Optimized Env Gene Inserts in Formulation DP6-001

Figure 14:
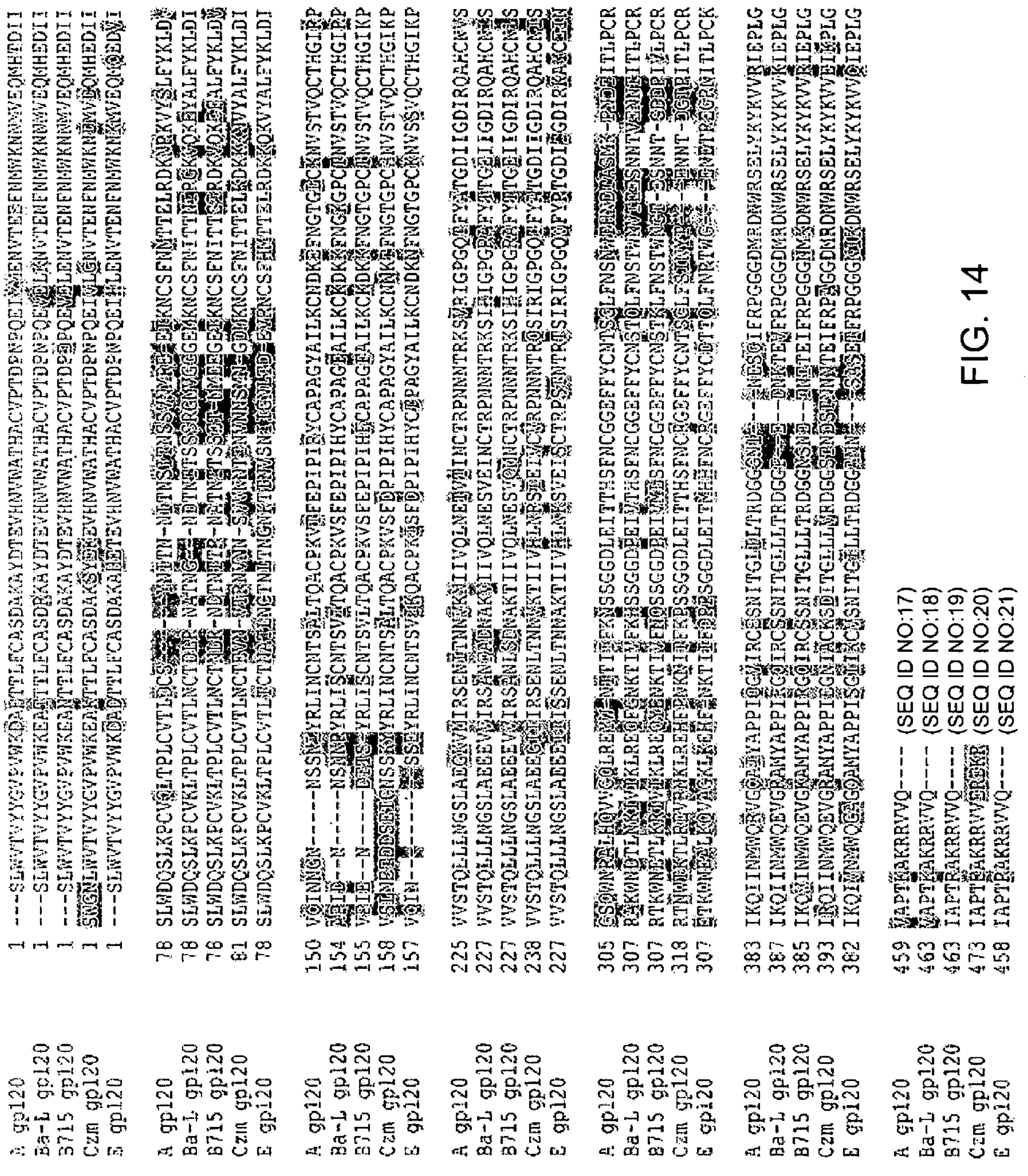
FIG. 14 depicts the amino acid sequences of gp120 from A, Ba-L, B715, Czm, and E isolates.
Figure 15A:
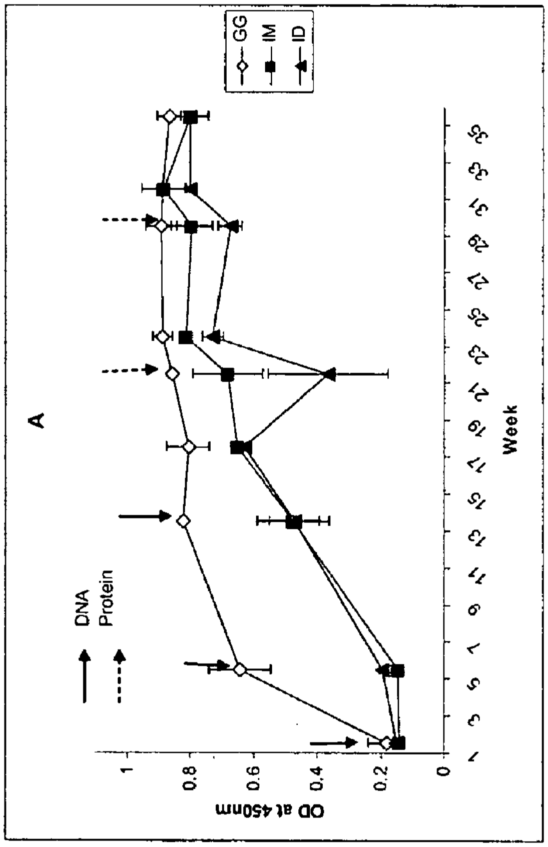
FIGS. 15A-E are a set of graphs depicting levels of anti-gp120 IgG responses after each DNA immunization and after each gp120 protein boost. The coating antigens for ELISA are shown on the top of each figure (clade A, B, Czm, and E for FIGS. 15A, 15B, 15C, and 15D, respectively). Times of administration of DNA and protein are depicted with solid and dashed arrows, respectively. “GG” refers to gene gun administration. “IM” refers to intramuscular administration. “ID” refers to intradermal administration.
Figure 15B:
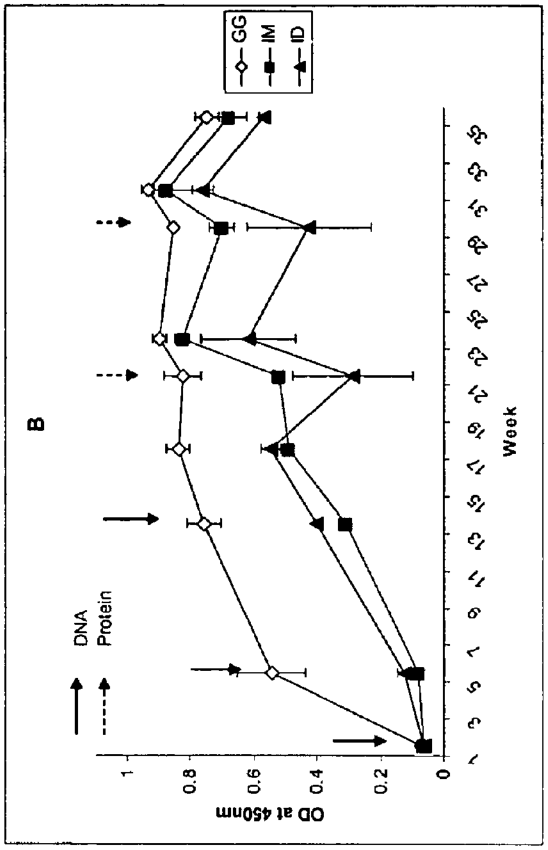
Figure 15C:
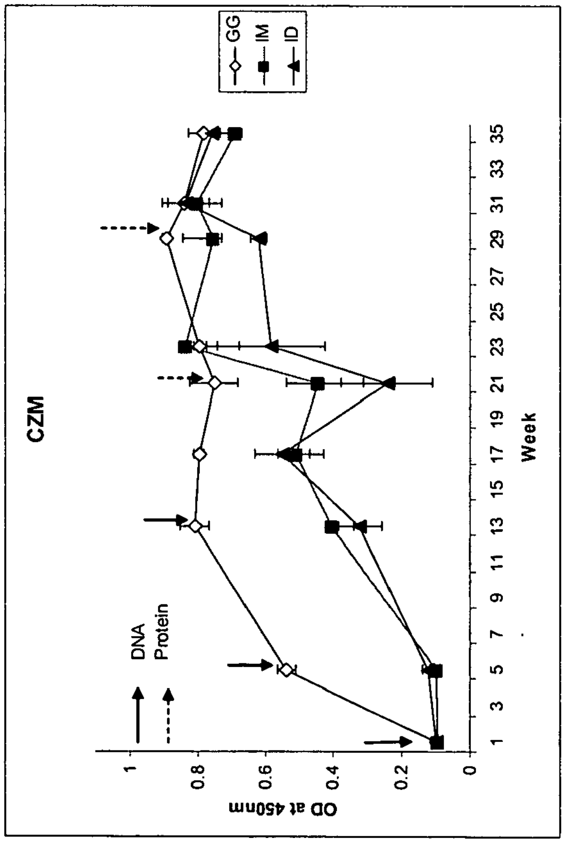
Figure 15D:
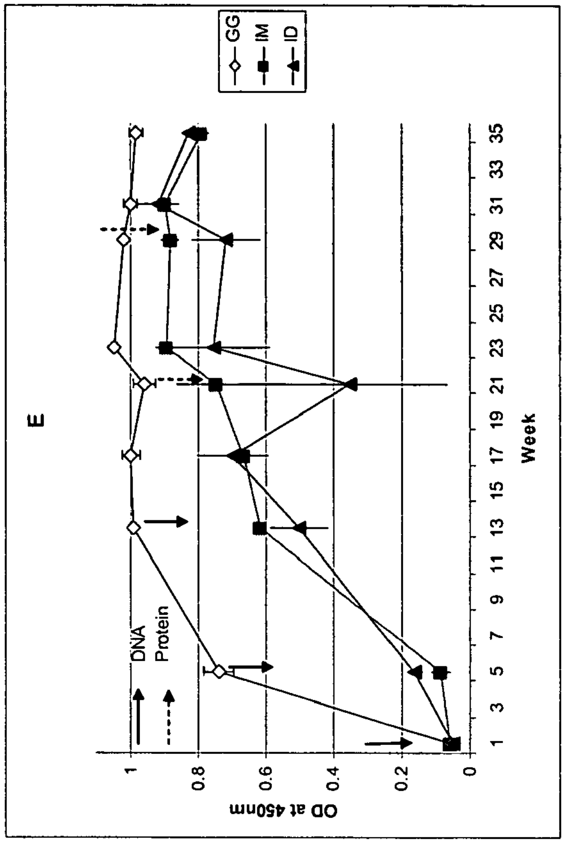
Figure 15E:
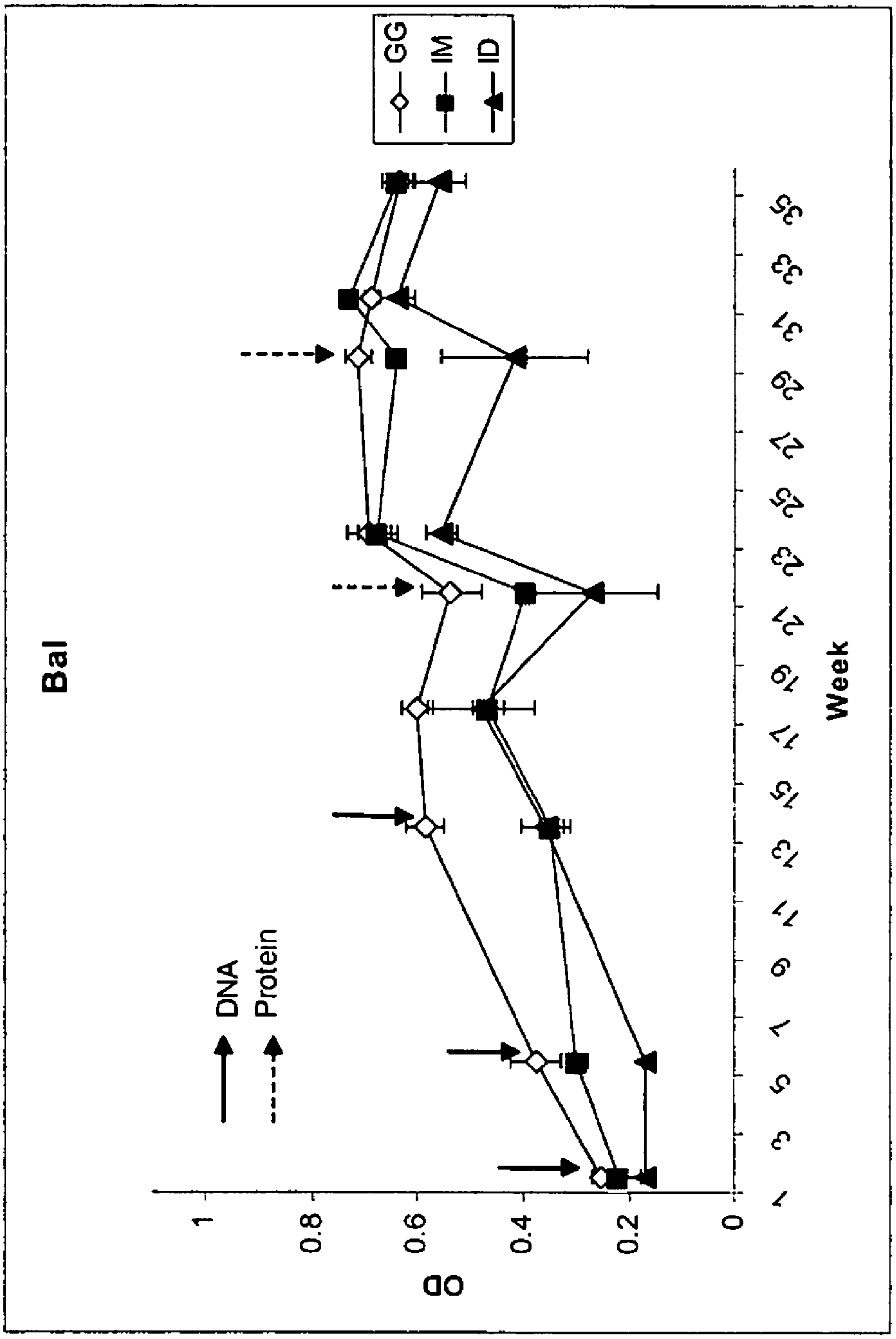

The immunogenicity of the codon optimized env and gag DNA vaccine components and the Env protein boost components to be used in the DP6-001 vaccine was examined. Rabbits were immunized with DNA components of DP6-001 vaccine by gene gun, ID or IM inoculation followed by gp120 protein boost by IM route so that anti-Env antibody responses could be compared. The amino acid sequences of the proteins used in the DP6-001 protein boosts are shown in FIG. 14, with the sequences aligned to each other. In previous rabbit studies, only non-codon optimized DNA vaccines were used.

For data presented in the previous studies, DNA plasmids were delivered by a gene gun immunization method. The study described in this example demonstrates the immunogenicity of DNA vaccines by intramuscular (IM) and intradernal (ID) injections.

Female rabbits were immunized with DNA vaccines expressing five primary HIV-1 Env antigens and one primary HIV-1 Gag antigen followed by two protein boosts including five primary gp120 antigens. The details of the immunization protocols are shown in Table 8. The DNA and protein components used in this study are the same as in the DP6-001 formulation. Each group of New Zealand White rabbits (two per group) received three DNA immunizations at weeks 1, 5, and 13, and two protein boosts at weeks 21 and 29. Animals received DNA immunization either by a gene gun (GG), IM or by ID injection. Proteins were formulated in QS-21 adjuvant and immunized by IM route. The total dose of immunogens for each immunization is listed in Table 8.

TABLE 8

Design of Rabbit Groups Immunized with Codon Optimized DNA Vaccines

| Groups | DNA priming | DNA Route | Total DNA Dose Per Immunization | Protein Boosting | Total Protein Dose Per Immunization |
|---|---|---|---|---|---|
| C30 | Env (A, B, Ba-L, Czm, E) + Gag (Czm) | Gene Gun | 36 µg (6 µg per individual DNA) | A, B, Ba-L, Czm, E | 100 µg (20 µg per protein) |
| C31 | Env (A, B, Ba-L, Czm, E) + Gag (Czm) | IM | 600 µg (100 µg/DNA) | A, B, Ba-L, Czm, E | 100 µg (20 µg per protein) |
| C32 | Env (A, B, Ba-L, Czm, E) + Gag (Czm) | ID | 600 µg (100 µg per DNA) | A, B, Ba-L, Czm, E | 100 µg (20 µg per protein) |

ELISA data showing anti-Env IgG responses in NZW rabbits that received DNA priming by different routes (gene gun, IM or ID) is depicted in FIGS. 15A-E. FIGS. 15A, 15B, 15C, 15D, and 15E depict responses against HIV-1 A, HIV-1B, HIV-1 Czm, HIV-1 E, and HIV-1 Ba-L isolates, respectively. Overall, the polyvalent formulation was able to induce broad antibody responses recognizing all five primary Env antigens.

While gene gun immunization remains the most effective approach in priming anti-Env antibody responses, both IM and ID routes were able to prime the animals and induced anti-Env IgG responses soon after one protein boost. It appears that ID had higher variations in antibody responses than the IM injection group. The antibody responses remained at relatively high level for more than 8 weeks after the last boost.

These data show that the DP6-001 formulation is immunogenic in NZW rabbits. Both IM and ID routes are effective in priming the anti-Env antibody responses, similar to the gene gun approach. Protein boosts are highly effective to bring the antibody responses to peak level primarily in animals immunized with DNA by ID and IM routes. Inclusion of a gag DNA construct did not appear to interfere with the immunogenicity of the polyvalent Env-expressing DNA plasmids.

Example 11

Serum Antibody Titers Elicited by a Repeat-dose Intramuscular, Intradermal, or Intramuscular and Intradermal DP6-001 Vaccine During a Toxicity Study in Rabbits The antibody responses elicited by repeated administration of DP6-001 vaccine in New Zealand White rabbits were evaluated to examine whether sera from rabbits that participated in a toxicity study had anti-Env and anti-Gag antibodies reactive to DP6-001 vaccine immunogens. For the DNA immunization phase, animals (at least five/sex/group total) were immunized four times every four weeks intramuscularly for a total animal dose of 7.2 mg per immunization (in 1.2 ml of diluent per DNA) or intradermally for a total animal dose of 3.6 mg per immunization (0.6 mg per DNA) of polyvalent DNA vaccine. Control animals were alternated (between dates of injection) between intradermal and intramuscular injections with the saline control. For the protein boost phase animals were immunized three times every four weeks intramuscularly for a total animal dose of 0.375 mg per immunization (0.075 mg per gp120). Each protein dose contained 0.05 mg of the adjuvant, QS-21, and 30 mg of excipient, cyclodextrin. QS-21 is a saponin adjuvant (a 3,28-O-bisglycoside quillaic acid) that can be obtained in high purity from Quillaja saponaria Molina extracts (Kensil, et al., 1998, Dev Biol Stand., 92:41-7). Sera were collected from each rabbit fourteen days after either four DNA or four DNA and three protein immunizations, and assayed by ELISA for antibodies to pooled gp120 (immunogens in DP6-001) and to Gag protein. Sera from control animals were also assayed for background reactivity.

Figures 16A, 16B:
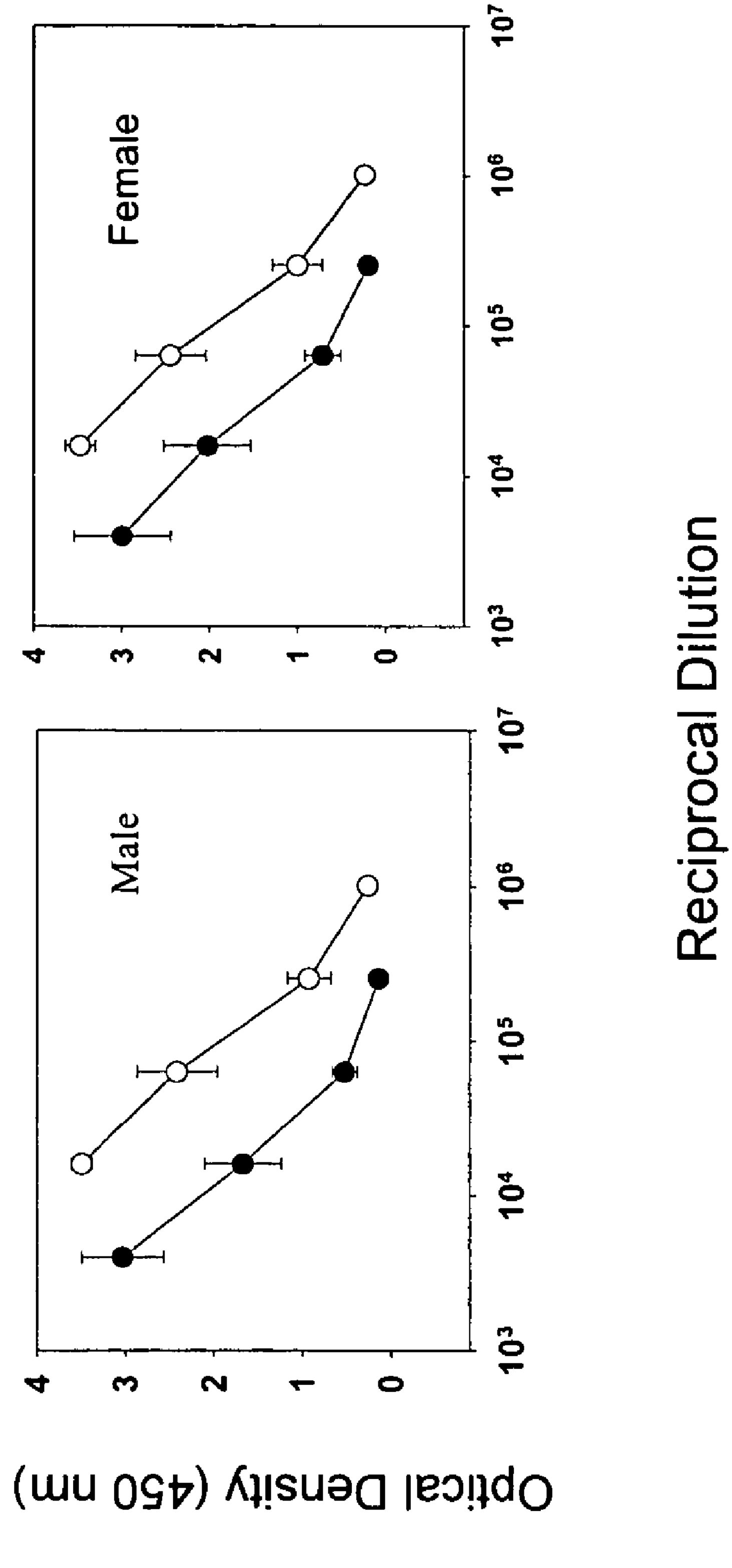
FIGS. 16A and 16B are a set of graphs depicting levels of anti-gp120 responses in rabbits immunized with DP6-001 vaccine in which DNA was delivered by an IM route. ELISA reactivity of sera from rabbits immunized with four DNA inoculations (IM) (closed circle) or four DNA (IM) and three protein inoculations (IM) (open circle) is shown. Sera were collected 14 days after last DNA or protein immunization and tested against pooled gp120 from clades B (B715 and Ba-L), C, E and A HIV-1 isolates. Data for males are shown in FIG. 16A. Data for females are shown in FIG. 16B.
Figures 17A, 17B:
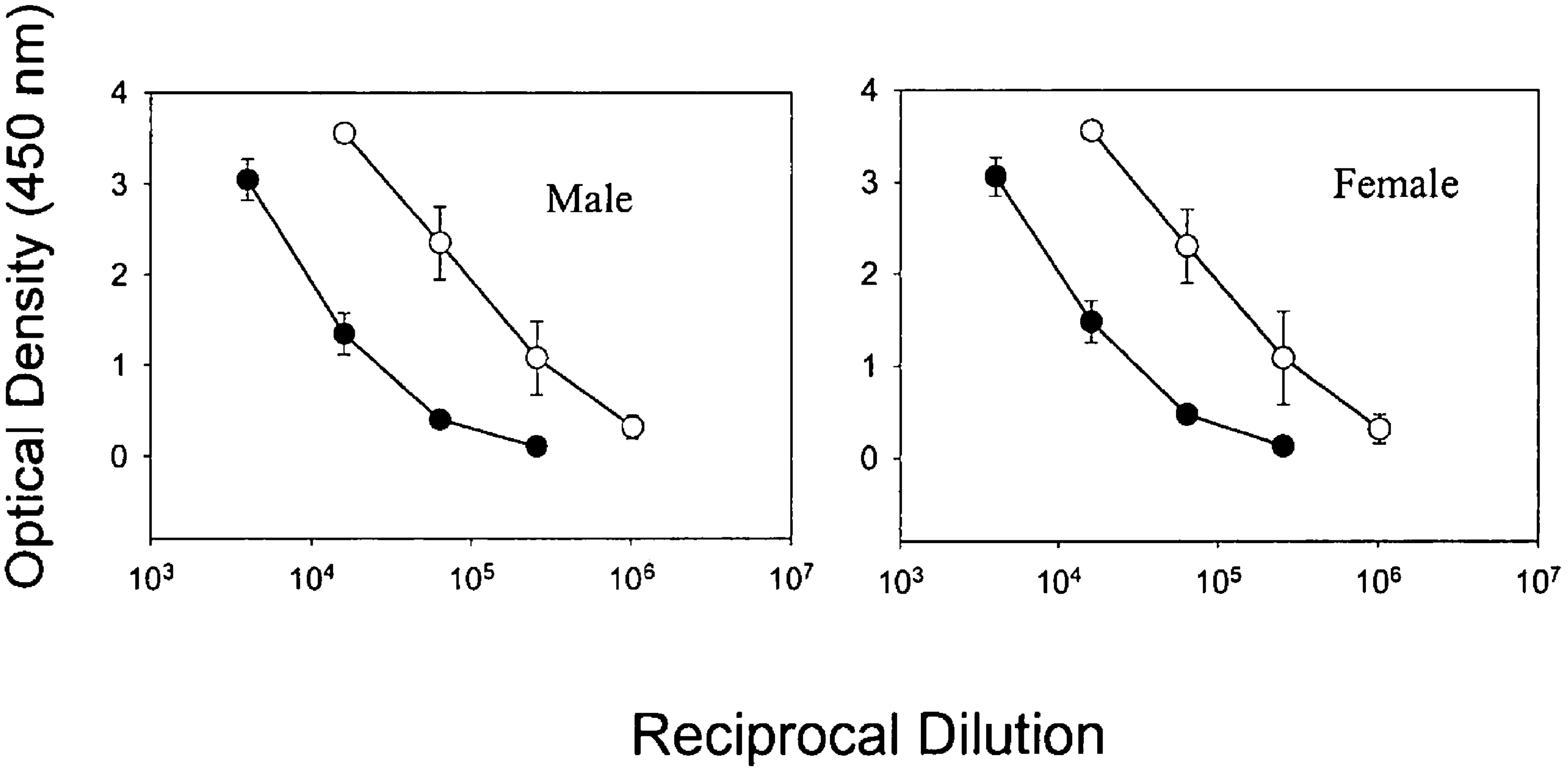
FIGS. 17A and 17B are a set of graphs depicting anti-gp120 response in rabbits immunized with DP6-001 formulation in which DNA was delivered by an ID route. ELISA reactivity of sera from rabbits immunized with four DNA inoculations (ID) (closed circle) or four DNA (ID) and three protein inoculations (IM) (open circle) is shown. Sera were collected 14 days after last DNA or protein immunization and tested against pooled gp120 from clades B (B715 and Ba-L), C, E and A HIV-1 isolates. Data for males are shown in FIG. 17A. Data for females are shown in FIG. 17B.
Figures 18A, 18B:
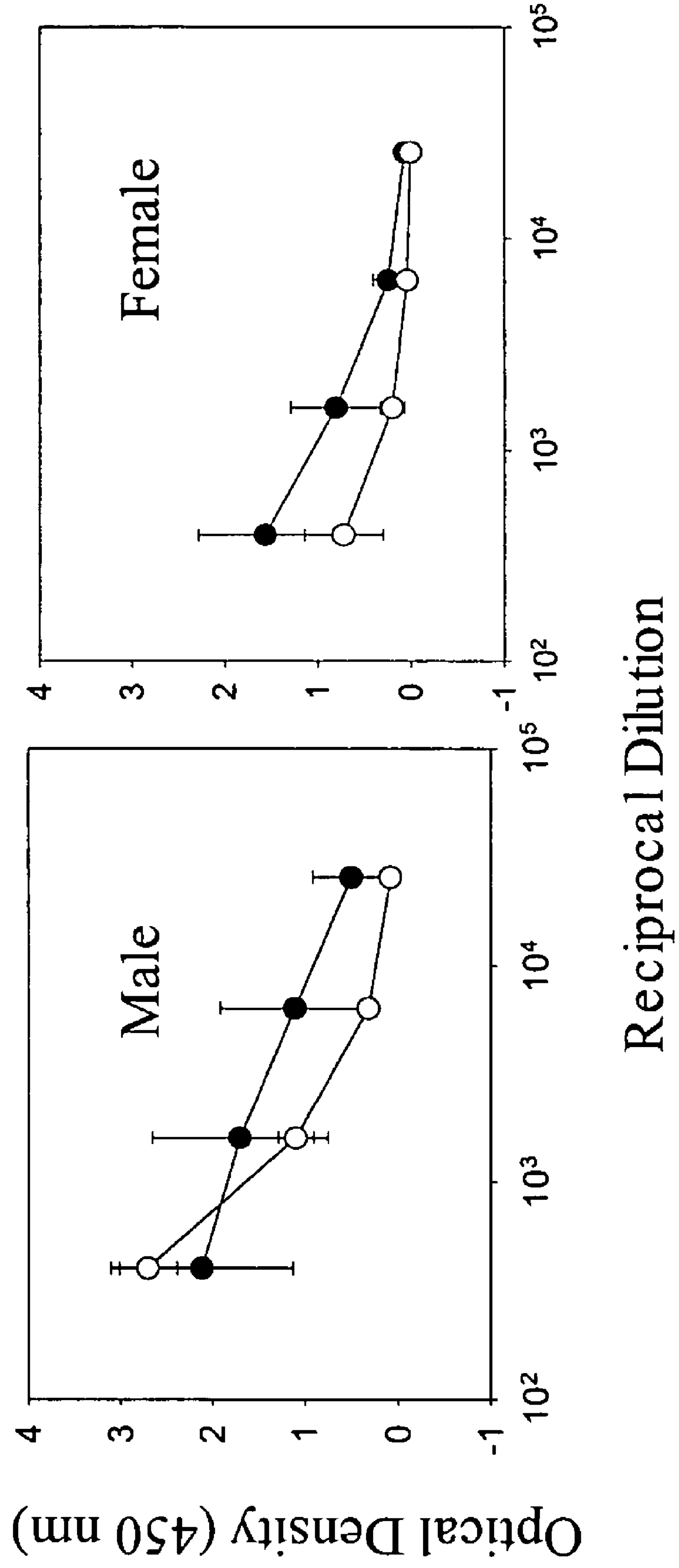
FIGS. 18A and 18B are a set of graphs depicting anti-gag responses in rabbits immunized with DP6-001 formulation in which DNA was delivered by an IM route. ELISA reactivity of sera from rabbits immunized with four DNA inoculations (IM) (closed circle) or four DNA (IM) and three protein inoculations (IM) (open circle) is shown. Sera were collected 14 days after last DNA or protein immunization and tested against Gag protein. Data for males are shown in FIG. 18A. Data for females are shown in FIG. 18B.
Figures 19A, 19B:
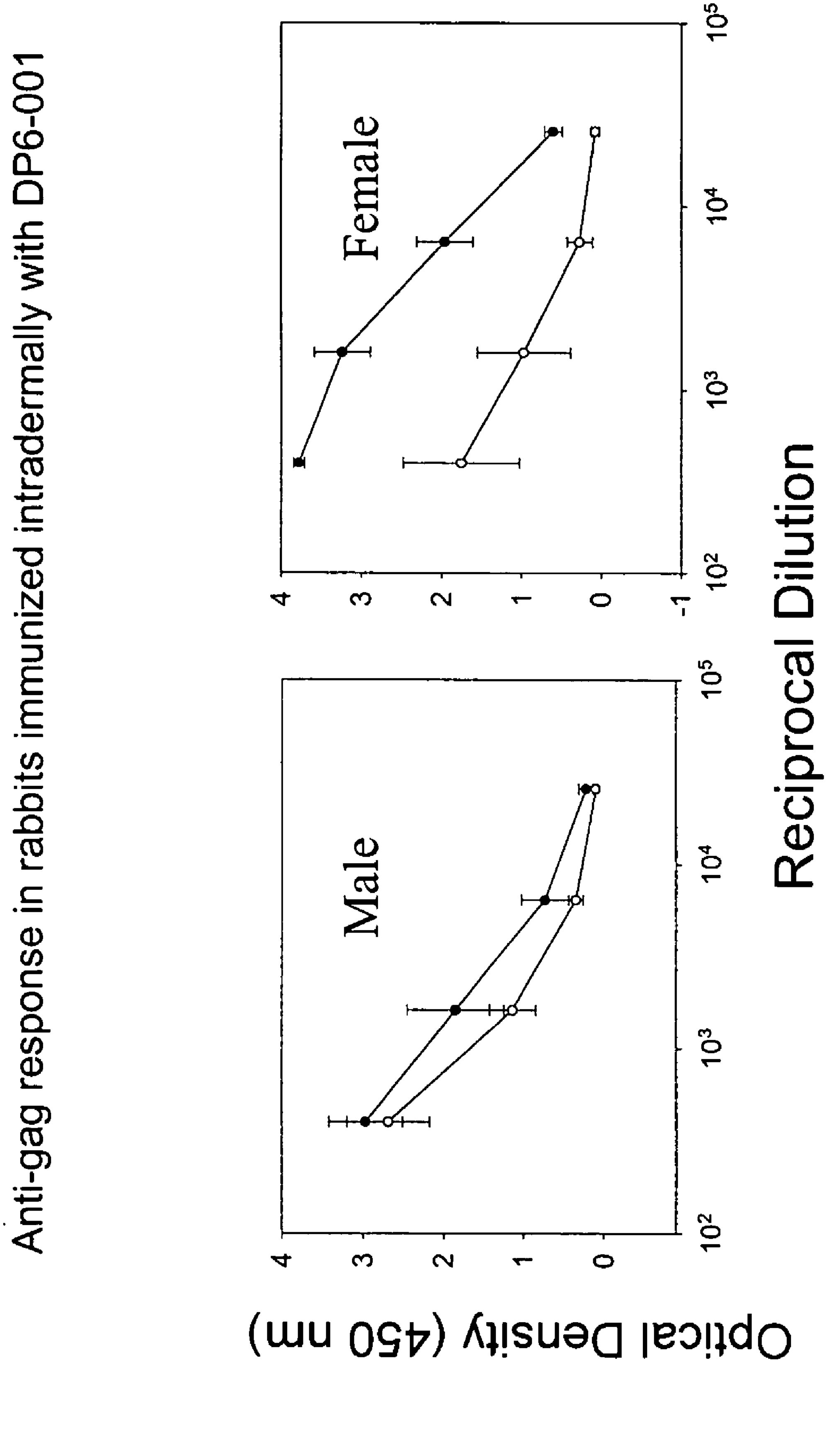
FIG. 19A and 19B are a set of graphs depicting anti-Gag responses in rabbits immunized with DP6-001 formulation in which DNA delivered by ID route. ELISA reactivity of sera from rabbits immunized with four DNA inoculations (ID) (closed circle) or four DNA (ID) and three protein inoculations (IM) (open circle) is shown. Sera were collected 14 days after last DNA or protein immunization and tested against Gag protein. Data for males are shown in FIG. 19A. Data for females are shown in FIG. 19B.
Figure 20A:
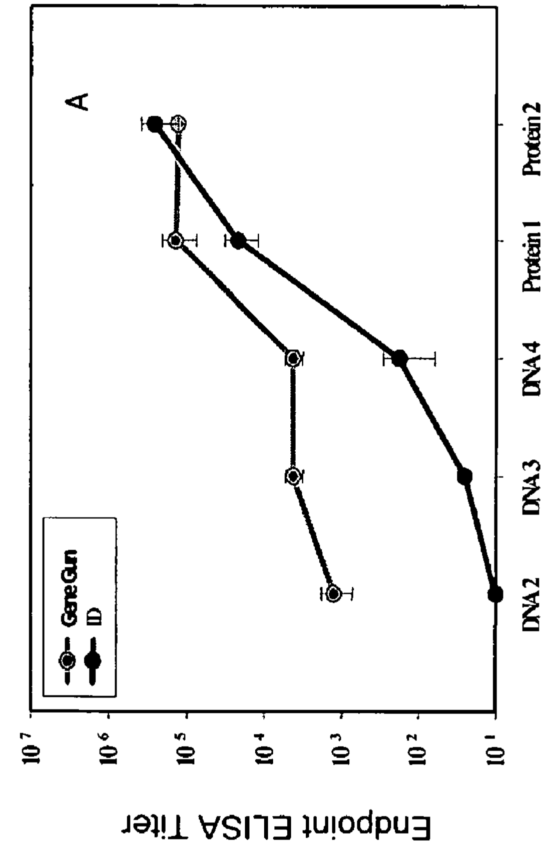
FIGS. 20A-E are a set of graphs depicting antibody titers in macaques immunized with polyvalent DNA and gp120 protein. Antibody titers in sera of macaques receiving two (DNA2), three (DNA3) and four (DNA4) DNA immunizations and one (Protein 1) and two (Protein 2) boosts were assayed by ELISA against B715 gp120 (A), Ba-L gp120 (B), Czm gp120 (C), E960 gp120 (D) and Gag (E) proteins. Serum was collected two weeks after each immunization. Antibody titers are based on end point ELISA titers and were obtained from the dilution of immune serum producing two times the optical density at 450 nm compared to the corresponding dilution of serum from a naive animal.
Figure 20B:
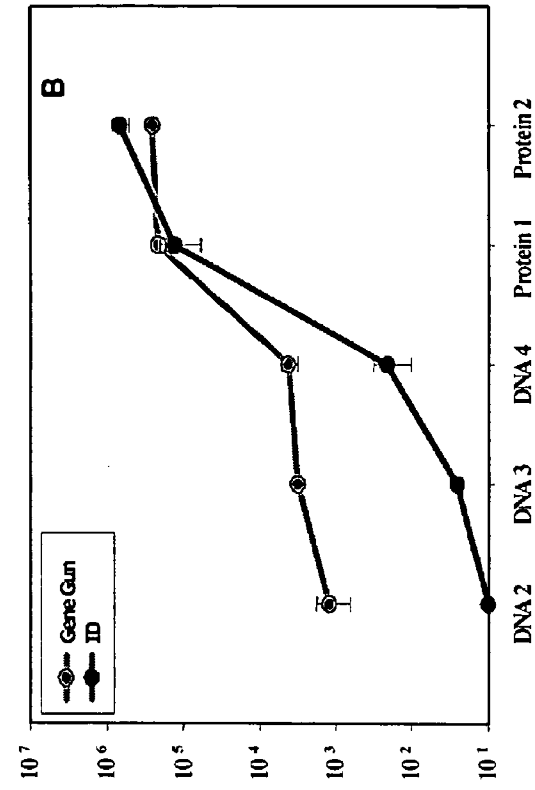
Figure 20C:
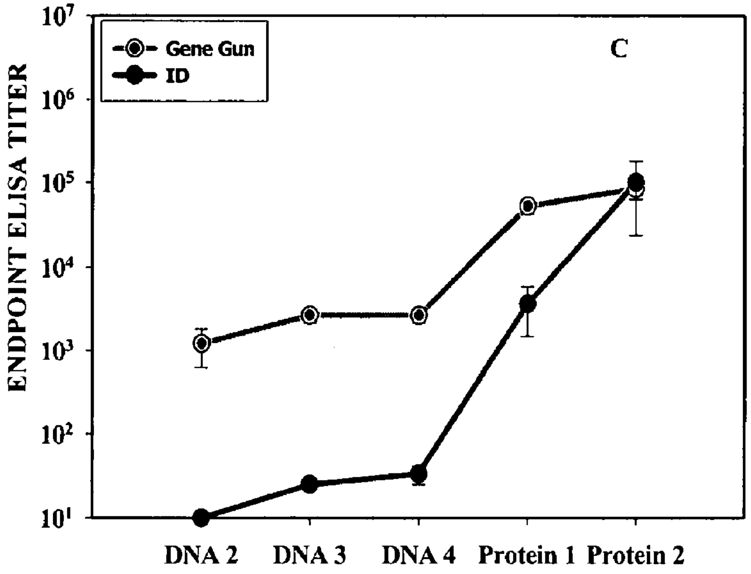
Figure 20D:
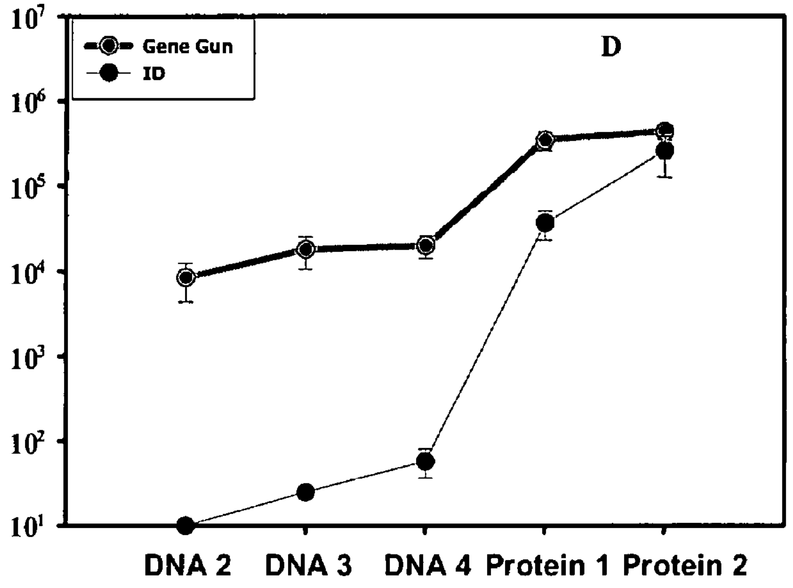
Figure 20E:
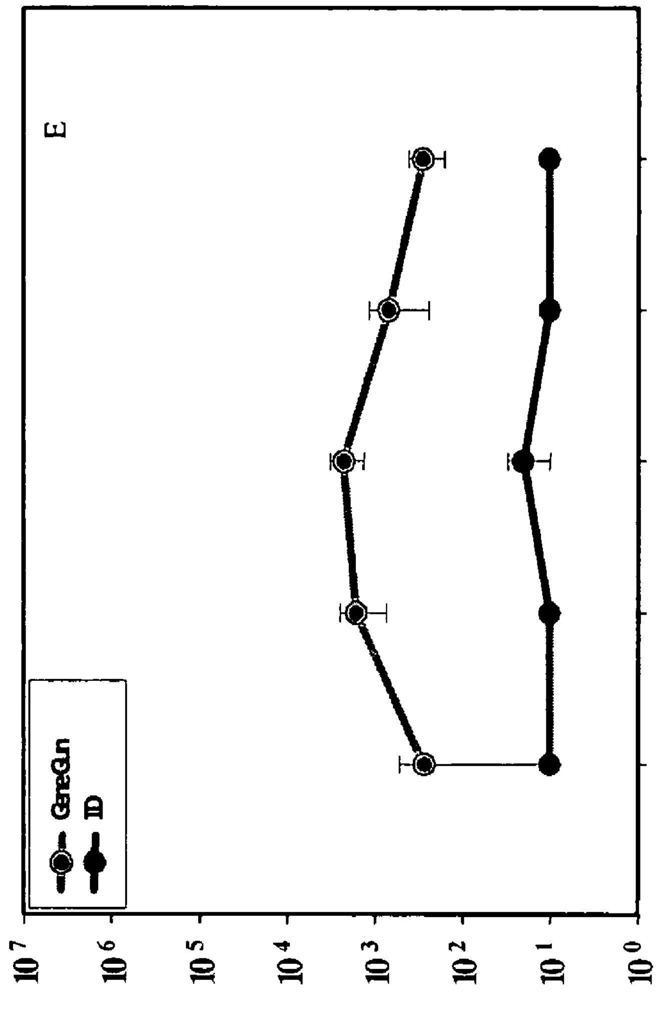

FIG. 16_shows anti-Env antibody titers in male and female rabbits immunized with 7.2 mg of DNA by IM route or 7.2 mg of DNA by IM route followed by 0.375 mg of gp120 boost intramuscularly. FIG. 17 shows anti-Env antibody titers in male and female rabbits immunized with 3.6 mg of DNA by ID route or 3.6 mg of DNA by ID route followed by 0.375 mg of gp120 boost intramuscularly. FIG. 18 depicts anti-Gag antibody titers in male and female rabbits immunized with 7.2 mg of DNA by IM route or 7.2 mg of DNA by IM route followed by 0.375 mg of gp120 boost intramuscularly. FIG. 19 shows anti-Gag antibody titers in male and female rabbits immunized with 3.6 mg of DNA by ID route or 3.6 mg of DNA by ID route followed by 0.375 mg of gp120 boost intramuscularly.

DNA delivered by both IM and ID routes were able to elicit strong antibody response in rabbits against both gp120 and Gag proteins. Antibody titers to gp120 were boosted significantly following gp120 protein boost. As expected, titers to Gag protein were not affected since the protein boost did not contain Gag protein. No significant difference in antibody titers was observed between groups receiving 3.6 or 7.2 mg of DNA. Sera from control animals did not show any reactivity with either gp120 or Gag protein (not shown).

Both DNA and gp120 protein immunizations of DP6-001 vaccine performed during the toxicology study elicited strong antibody response in rabbits. DNA immunizations had a very strong priming effect, which was significantly boosted following gp120 protein immunizations.

Examples 12 and 13

Immunogenicity of Polyvalent DNA Vaccines Encoding Codon Optimized env and gag Genes Followed by gp120 Protein Boost in Nonhuman Primates Two studies were conducted in nonhuman primates to evaluate immunogenicity of polyvalent DNA prime gp120 protein boost vaccines. In the first study (referred as DNA wt/Protein Study 1), immunogenicity of five DNA vaccines encoding wild type gp120 (B715, Ba-L, Czm and E) and gag (pNL4-3) genes were delivered either by ID or gene gun route. The protein boost consisted of gp120 from clades B715, Ba-L, Czm and E. This study revealed that DNA delivered by gene gun favored antibody over CMI response whereas DNA delivered by ID route had measurable CMI response. Antibody responses were markedly enhanced following gp120 boost in both ID and gene gun groups. To elicit both CMI and antibody responses, a second study (referred as DNA opt/Protein study 2) was conducted where immunogenicity of DP6-001 vaccine containing codon-optimized gp120 genes from A, B715, Ba-L, Czm and E isolates and Czm gag gene was examined. In this study DNA was delivered by either ID or IM route.

Example 12

DNA wt/Protein-Study 1 to Investigate the Immunogenicity of a Polyvalent Combination Vaccine of DNA Encoding four Wild Type gp120 Env Proteins and a Gag Protein and Boosts With Four gp120 Proteins in Rhesus Macaques The experiments in this example were undertaken to examine immune response in rhesus macaques elicited by priming with polyvalent DNA vaccines encoding a Gag protein and four Env proteins followed by boosting with four gp120 proteins homologous to the DNA vaccines. Six rhesus macaques (male) were included in this study. The polyvalent vaccine formulation tested in this study had one Gag and four Env antigens unlike the DP6-001 formulation, which has one Gag and five Env antigens. Animals were immunized four times with a mixture of five DNA plasmids (four plasmids encoding wild type env genes from clade B Ba-L, clade B B715, clade C Czm and clade E 976; and one plasmid encoding HIV-1 clade B gag gene) in saline. Three animals (961L, 963L and 969L) were immunized with DNA by gene gun, whereas the other three animals (971L, 974L and 975L) received DNA by ID route. Each animal was then boosted with purified gp120 from four isolates representing B, Ba-L, Czm and E two times by IM route. For each ID immunization, 500 μg of each plasmid DNA (2.5 mg total) was injected separately. For gene gun inoculation, 20 μg of each DNA (100 μg total) was delivered. Each animal received 75 μg of each gp120 (300 μg of pooled gp120) formulated in 100 μg of QS-21 adjuvant in PBS. Animals were immunized with DNA on weeks 0, 6, 12 and 18 followed by protein boosts on weeks 24 and 32. Serum was collected at designated times, generally two weeks after each immunization.

Serum antibody titers to all five envelope and the Gag proteins following each immunization of DNA and protein were assayed by ELISA (FIG. 20). These results clearly demonstrate that DNA delivered via gene gun elicited higher antibody response against gp120 and Gag proteins than DNA administered by ID inoculation, and antibody titers increased progressively following each DNA immunization. However, boosting of DNA primed animals with a single gp120 protein enhanced antibody titers markedly in both groups of animals to a comparable level. A slight increase in antibody response was noted following the second gp120 boost. As expected, no change in anti-gag antibody titers was noted following gp120 immunization (FIG. 20E).

Figure 21B:
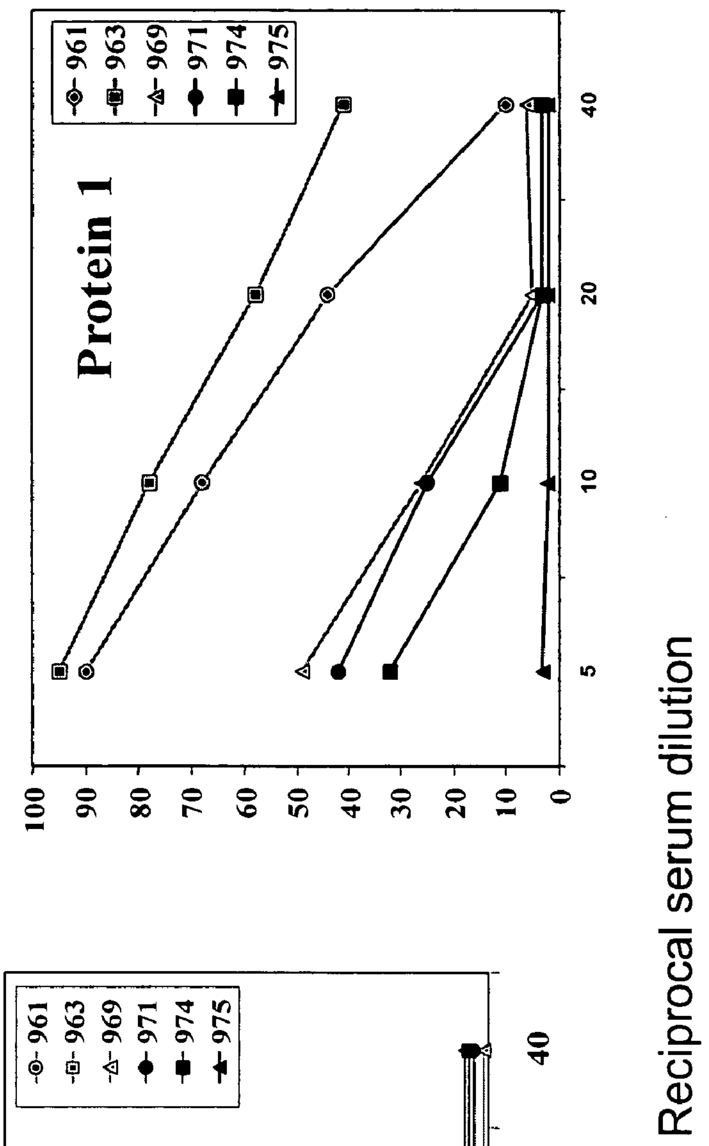
FIGS. 21A-21C are a set of graphs depicting percent neutralization of SHIV Ba-L by the serum of macaques immunized with DNA prime and protein boost. Serum from each animal collected after four DNA (DNA 4) and one (protein 1) and two (protein 2) boosts were assayed for neutralizing activity against $SHIV_{Ba-L}$ isolate in U373 cells. Percent inhibition of infection was based on the degree of infection observed in the presence of immune serum compared to untreated controls.
Figure 21A:
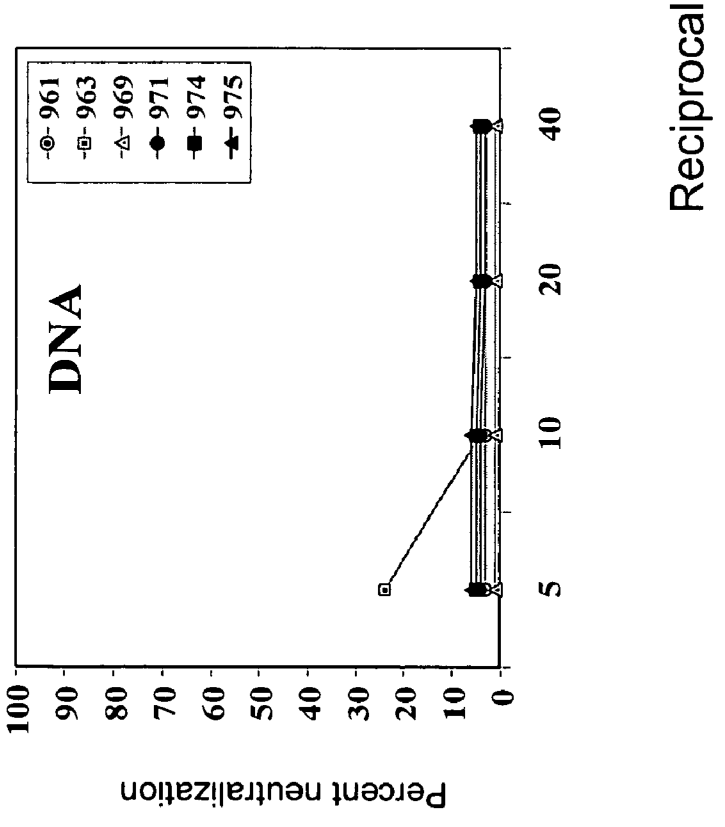
Figure 21C:
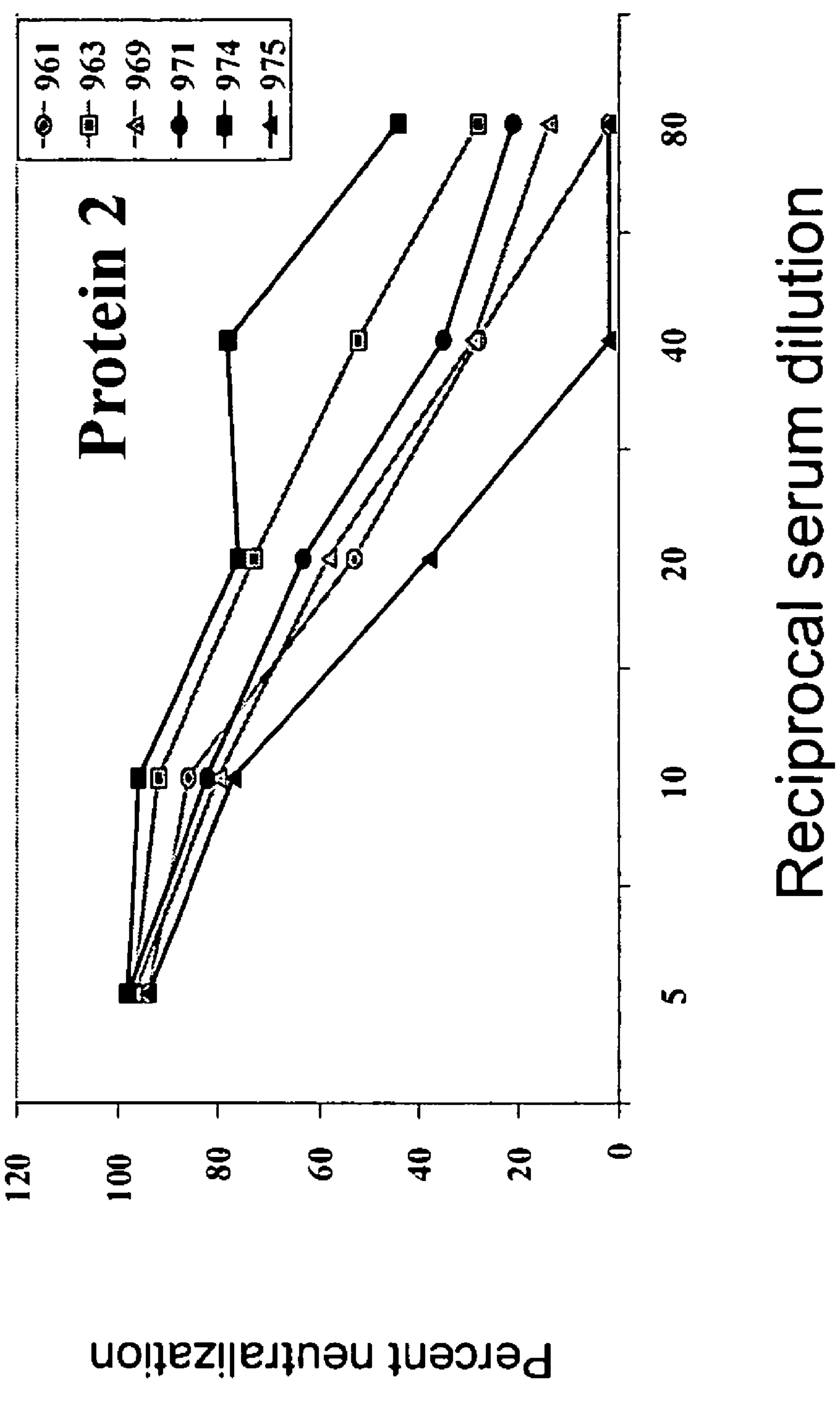
Figure 22A:
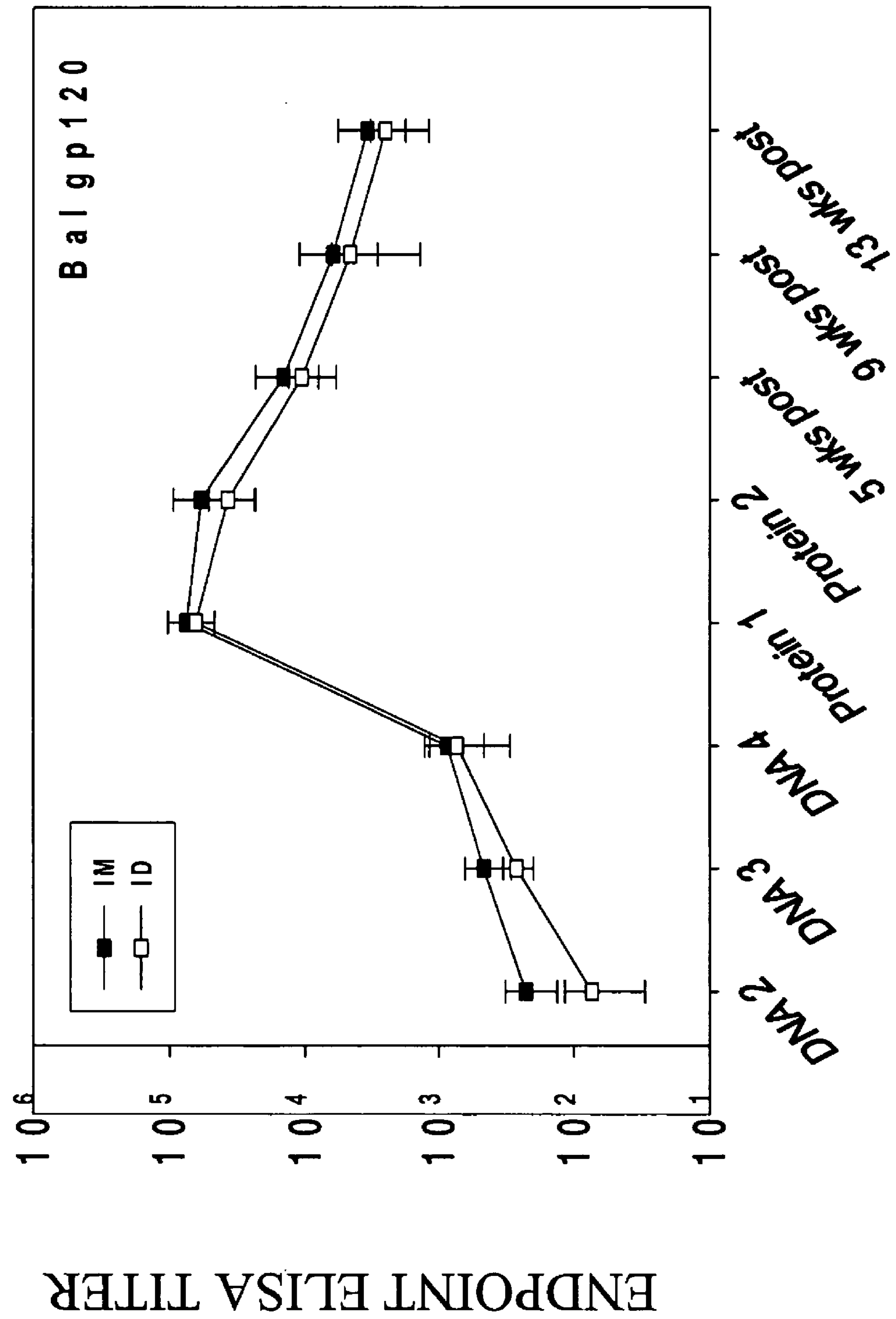
FIGS. 22A-22E are a set of graphs depicting serum end-point ELISA titers in macaques immunized with polyvalent DNA and gp120 Protein. Antibody titers in sera of macaques receiving two (DNA 2), three (DNA 3) and four (DNA 4) DNA immunizations and one (Protein 1) and two (Protein 2) boosts at 5, 9 and 13 weeks post protein boost sera were assayed by ELISA against Ba-L gp120 (A), A gp120 (B), E760 gp120 (C), B715 gp120 (D) and Czm gp120 (E) proteins. Serum was collected two weeks after each immunization and 5, 9 and 13 weeks after the second protein boost. Antibody titers are based on end point ELISA titers and were obtained from the dilution of immune serum producing two times the optical density at 450 nm compared to the corresponding dilution of serum from a naive animal.
Figure 22B:
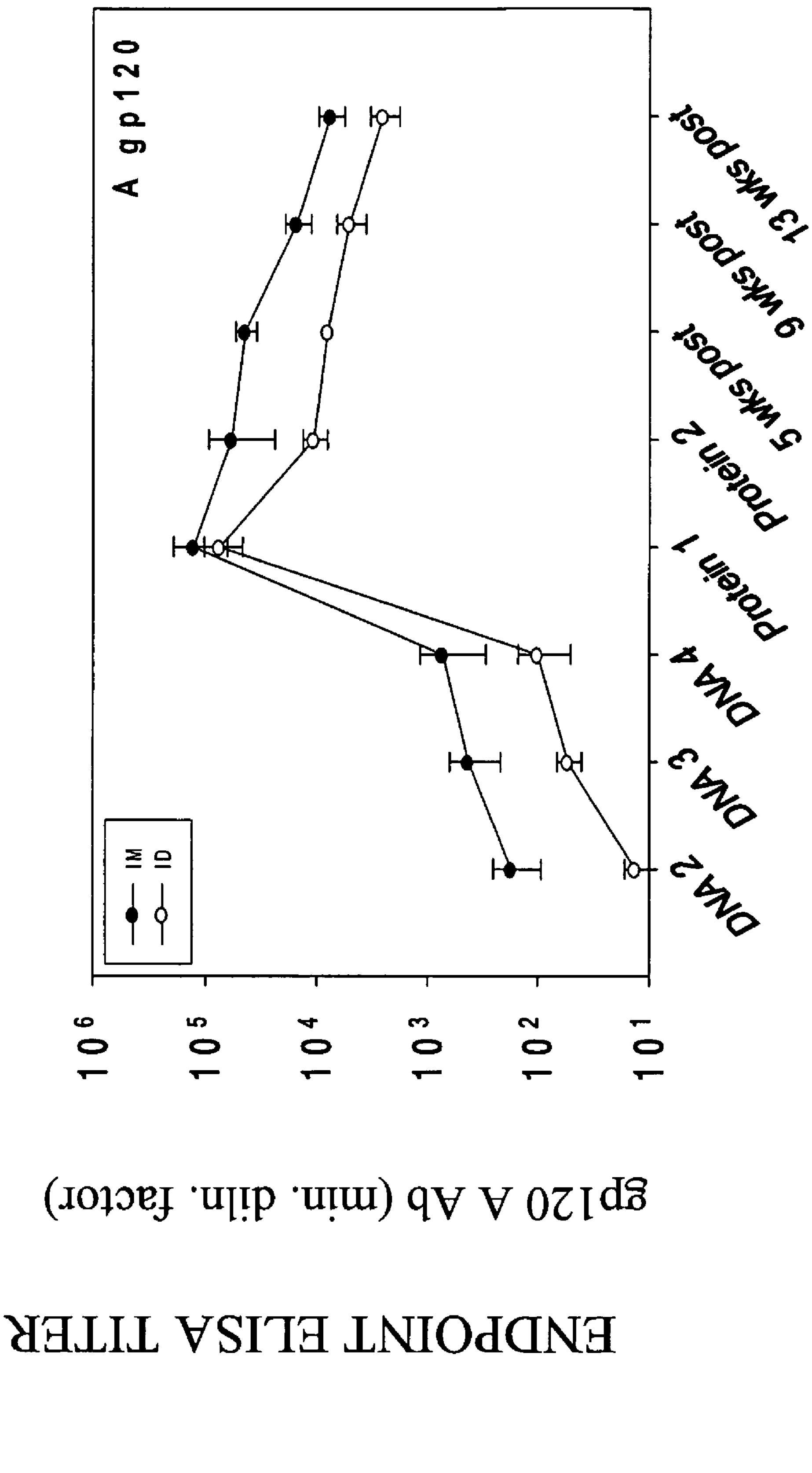
Figure 22C:
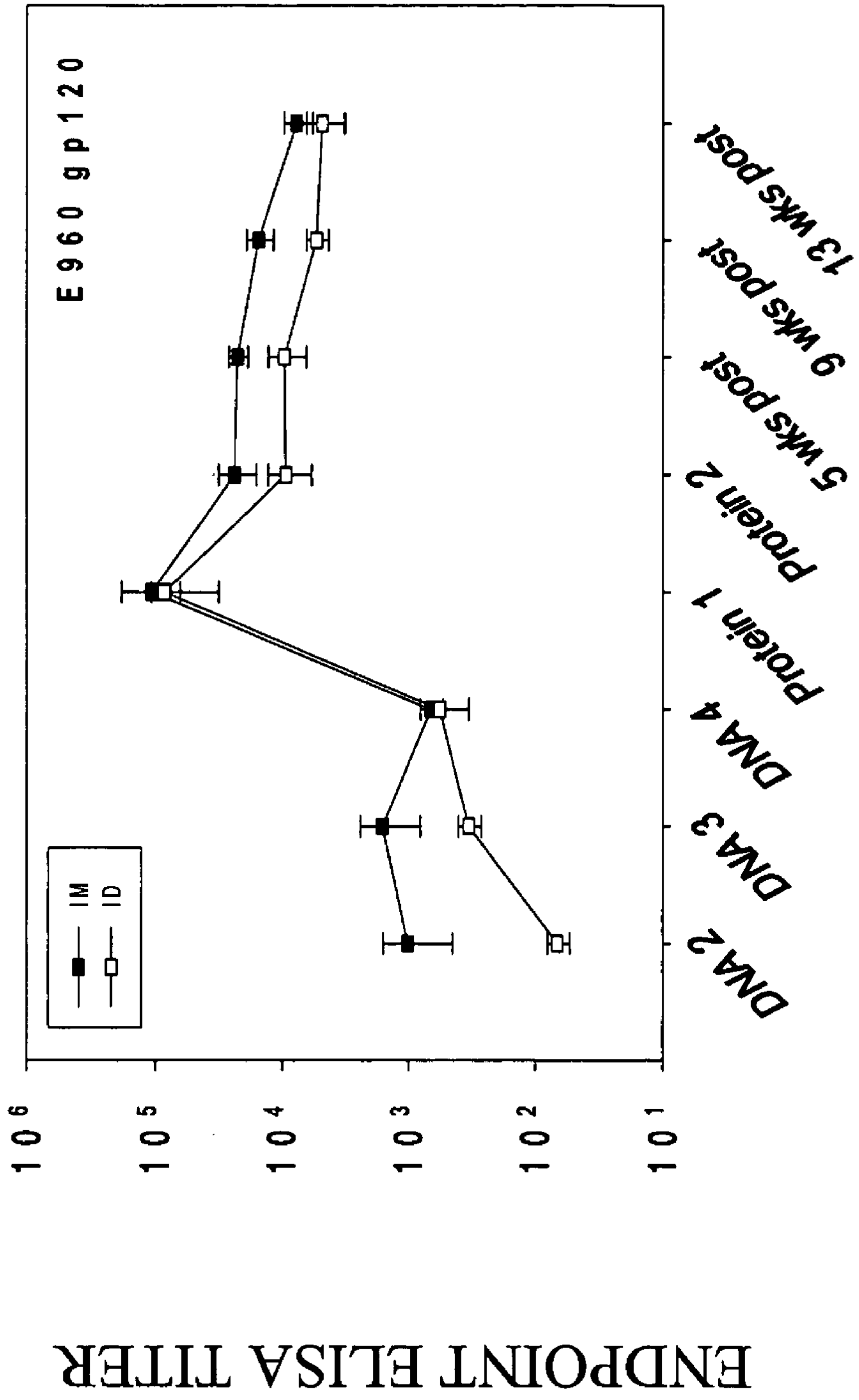
Figure 22D:
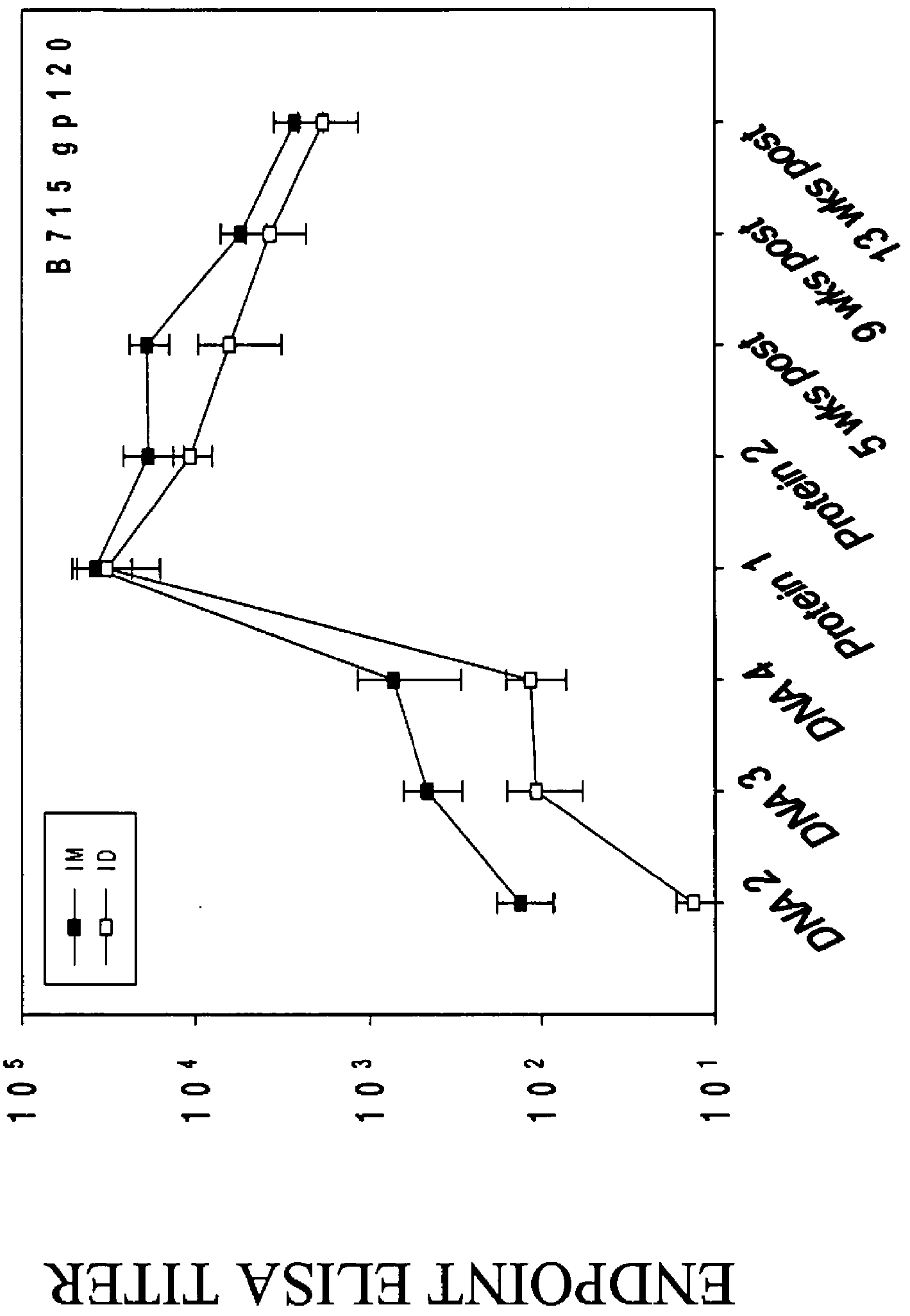
Figure 22E:
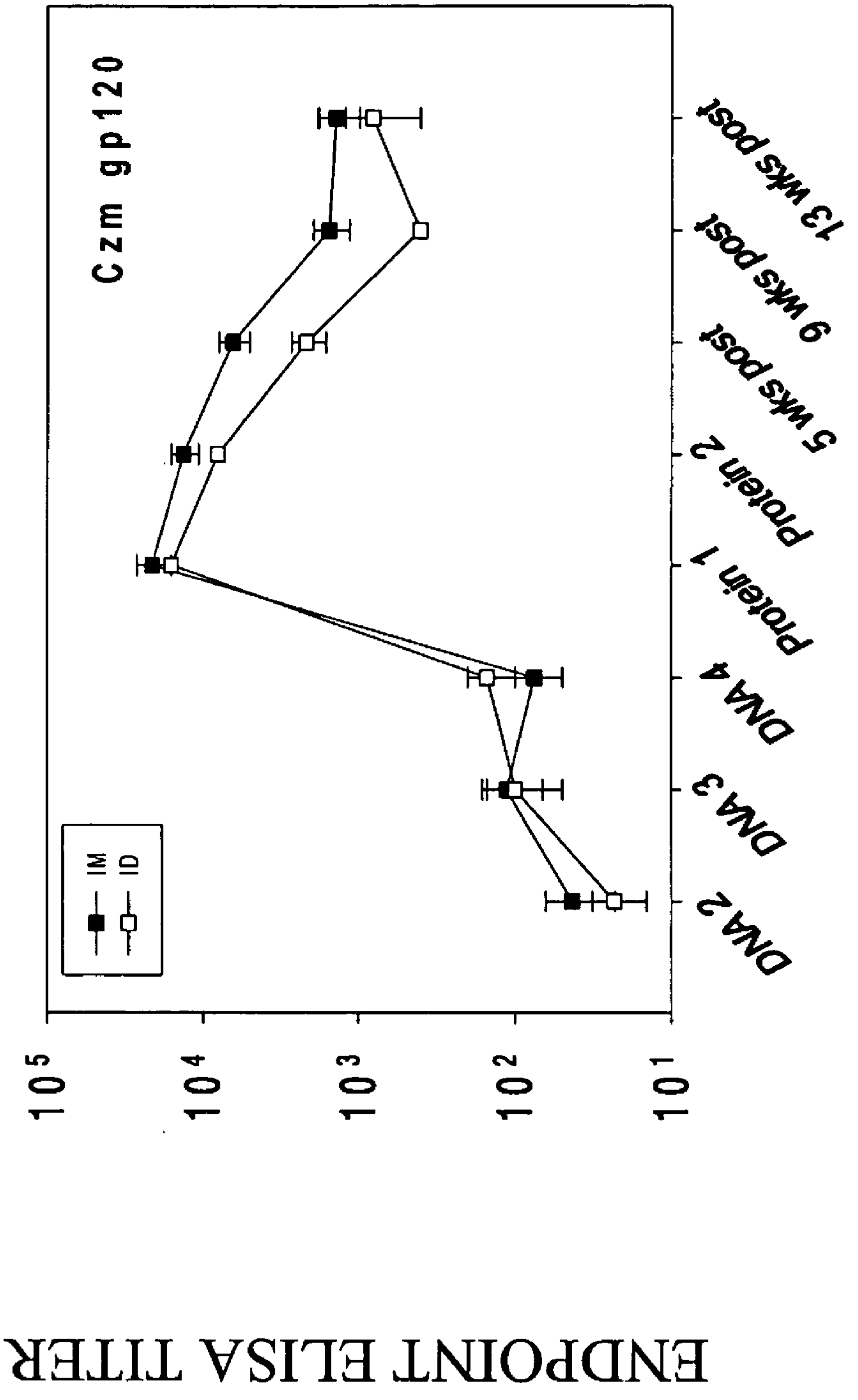

To determine whether antibodies elicited by this vaccine are functional, sera collected after the fourth DNA and two protein boost were assayed for neutralization of HIV-1 and SHIV isolates encoding env genes homologous to gp120 genes of DP6-001 vaccine. These viruses include both $SHIV_{Ba\text{-}L}$ and primary $HIV\text{-}1_{Ba\text{-}L}$ isolates encoding Ba-L env gene, $HIV\text{-}1_{Czm}$ encoding Czm env gene, and $HIV\text{-}1_{B715}$ encoding B715 env gene. Sera obtained from macaques after four DNA immunizations and gp120 boost neutralized $SHIV_{Ba\text{-}L}$ (FIG. 21). Four DNA immunizations did not elicit neutralizing activity against a $SHIV_{Ba\text{-}L}$ isolate (FIG. 21A). However, sera from the immunized animals harvested after each gp120 boost were able to inhibit $SHIV_{Ba\text{-}L}$ infection (FIGS. 21B and C). Neutralization titers of sera from these animals harvested after protein boost against a number of homologous and a few heterologous HIV-1 isolates are presented in Table 9A. Percent inhibition of infection by the sera is presented in Table 9B. Sera collected after four DNA inoculations did not neutralize any of these isolates (data not shown). However, a few of these isolates were neutralized by sera after protein boost.

TABLE 9A

Neutralization Titers of Serum from Immunized Animals Against HIV-1/SHIV Isolates

| Animal | Neutralization Titer | | | | | |
|---|---|---|---|---|---|---|
| | HIV-1 Clade B | | | | HIV-1 Clade C | |
| Number | SHIVBa-L | MN | 89.6 | B715 | 93MW160 | 931N101 |
| 961L | 23 | 41 | 6 | <5 | <5 | <5 |
| 963L | 41 | 100 | 6 | <5 | <5 | <5 |
| 969L | 24 | 48 | 15 | <5 | <5 | <5 |
| 971L | 27 | 54 | 8 | 5.5 | <5 | <5 |
| 974L | 78 | 100 | 8 | 10 | <5 | <5 |
| 975L | 17 | 51 | 7 | <5 | <5 | <5 |

Serum collected after 2 Protein boosts were assayed. Neutralization titers are calculated based on the dilution of immune serum inhibiting 50% of infection compared to untreated controls.

TABLE 9B

| Animal | % Inhibition of Infection HIV-1 Clade B | | | | | |
|---|---|---|---|---|---|---|
| Number | Ba-L | SF162 | ADA | 5768 | 515 | PVO |
| 961L | 80 | 63 | 0 | 0 | 0 | 0 |
| 963L | 77 | 87 | 0 | 0 | 0 | 0 |
| 969L | 16 | 81 | 10 | 0 | 0 | 0 |
| 971L | 67 | 66 | 0 | 0 | 0 | 0 |
| 974L | 89 | 93 | 0 | 0 | 0 | 0 |
| 975L | 47 | 76 | 0 | 0 | 0 | 0 |

Serum collected after 4 DNA and 2 Protein boosts were assayed. Each serum was tested at 1:16 dilution for neutralization of indicated HIV-1 isolates using human PBMC targets. Percent inhibition was based on the degree of infection observed in the presence of immune serum compared to untreated controls In summary, immunization of macaques with polyvalent DNA vaccines encoding four env genes and a gag gene primes the immune system significantly. Protein boosts are highly effective in eliciting a broad antibody response. This antibody response was able to neutralize homologous, and to lesser extent, heterologous primary HIV-1 isolates.

Example 13

DNA opt/Protein-Study 2: Immunogenicity of DP6-001 Vaccine in Rhesus Macaques

Humoral and cellular immune responses elicited by DP6-001 vaccine in rhesus macaques were examined. Six (five male and one female) rhesus macaques participated in this study. Animals were immunized with a mixture of six DNA plasmids: five plasmids encoding codon optimized env genes from clade A, B Ba-L, clade B B715, clade C Czm and clade E 976, and one plasmid encoding HIV-1 clade C gag gene, in saline four times. Three animals (51M, 978L, 980L) were immunized with DNA by IM route and three animals (991L, 997L, 998L) received DNA by ID route. Each animal was then boosted with purified gp120 from five isolates representing A, B, Ba-L, Czm and E two times by IM route. For each immunization, 500 μg of each plasmid DNA (3 mg total) was pooled and suspended in a total volume of 2 ml saline. Each animal received 3 mg of total DNA either by IM or by ID route. For ID immunization DNA was delivered into 19 sites (100 μl per site). For IM inoculation, DNA was delivered into 4 sites (500 μl per site). Animals received 375 μg of pooled gp120 (75 μg of each gp120) in 100 μg of QS-21 adjuvant in 1 ml of PBS. Animals were immunized with DNA on weeks 0, 6, 12 and 18 followed by protein boost on weeks 24 and 32. Serum was collected approximately two weeks after each immunization. Sera were collected up to week 49 for a binding antibody assay.

Antibody titers to all five envelope proteins following each immunization of DNA and protein were assayed by ELISA and the results are shown in FIG. 22. These results demonstrate that DNA delivered via the IM route elicited a higher antibody response against at least against three out of five envelope proteins as compared to DNA delivered via an ID route, and antibody titers increased progressively following each DNA immunization. However, boosting of DNA primed animals with gp120 protein enhanced antibody titers markedly in both groups of animals to a comparable level. Antibody levels decreased slightly following the second protein boost with progressive drop over time. Titers of anti-Gag antibodies were low in each animal during both DNA and protein immunization phase (data not shown).

To determine whether antibodies elicited by the DP6-001 vaccine are functional, sera collected after the fourth DNA administration and the protein boost were assayed for neutralization of a few HIV-1 and SHIV isolates encoding env genes homologous to gp120 genes of the DP6-001 vaccine. These viruses include both $SHIV_{Ba-L}$ and primary $HIV\text{-}1_{Ba-L}$ isolates including a Ba-L env gene, $HIV\text{-}1_{Czm}$ a Czm env gene and $HIV\text{-}1_{B715}$ including a B715 env gene. Neutralization of both cell-free and cell-to-cell transmission of HIV-1/SHIV by the hyperimmune sera was assayed. For assays with cell-free virus, heat inactivated serum was incubated at 37° C. with cell-free virus and the virus/serum mixture was subsequently used to infect a U373 cell line containing the reporter gene β-galactosidase. Neutralization of cell-to-cell transmission of HIV-1 was conducted by a syncytium inhibition assay in which chronically infected cells were cocultured with uninfected cells in the presence of the sera. Coculturing of cells induces syncytium formation which was inhibited by the neutralizing sera. Each neutralization assay included controls where infection assays were conducted with either no serum or pre-immune or normal rhesus serum.

Figure 23A:
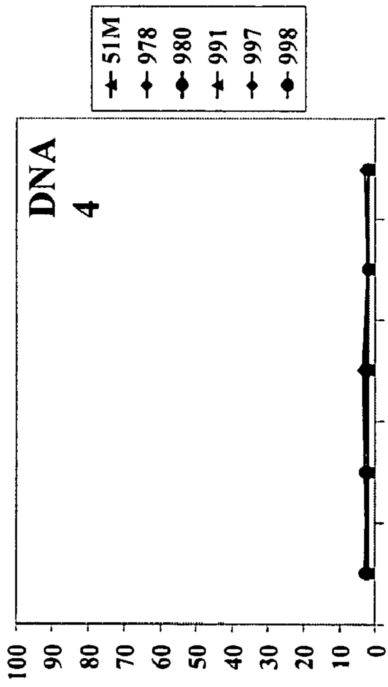
FIGS. 23A-23C are a set of graphs depicting percent neutralization of SHIV Ba-L by the serum of macaques immunized with DNA prime and protein boost. Serum from each animal collected after four DNA (DNA 4.
Figure 23B:
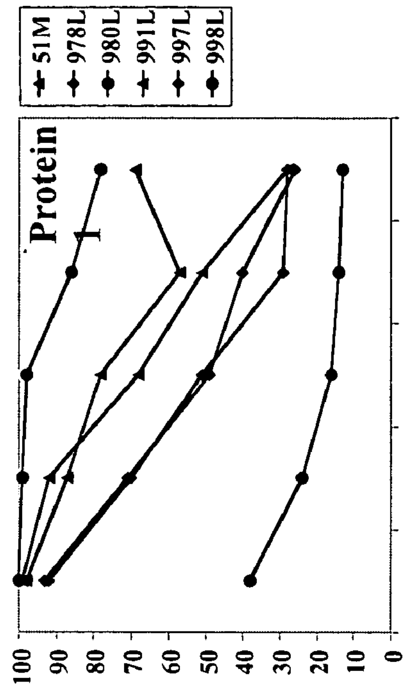
Figure 23C:
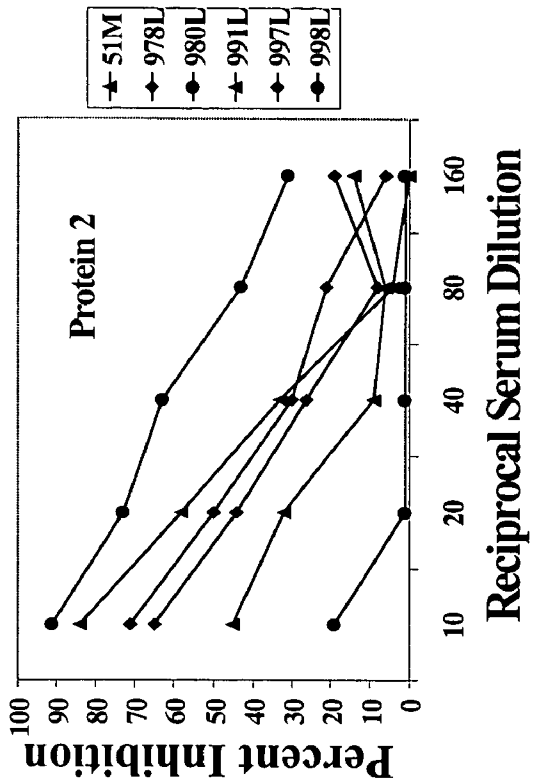
Figure 24A:
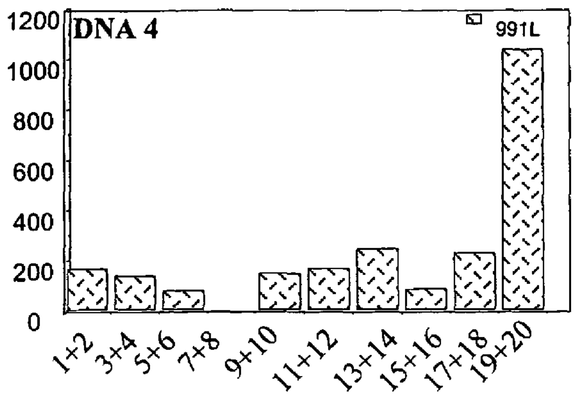
FIGS. 24A-24R are a set of graphs depicting numbers of IFN-γ Expressing PBMC from macaques immunized with DNA/Protein formulations, in which PBMC were stimulated with Gag peptides. ELISPOT assays were conducted using PBMC of macaques isolated after the fourth DNA (DNA 4), first (protein 1) and second (protein 2) gp120 protein boosts. Several pools of 15 mer peptides with 11 amino acid overlap from Gag protein from HIV-1HXB2 molecular clone were used for stimulation of PBMC for 18 hrs before the spots were developed and quantitated. Data for ID immunization are shown in FIG. 24A-24I. DNA for IM immunization are shown in FIGS. 24J-24R.
Figure 24B:
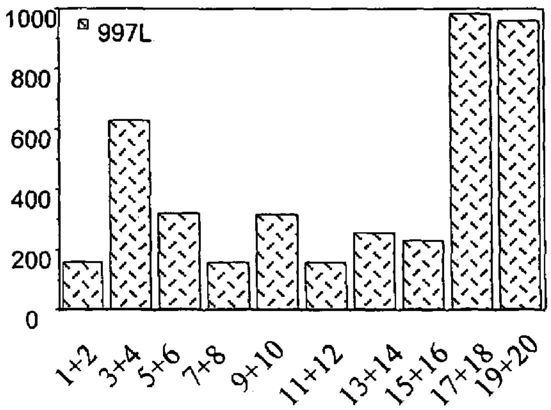
Figure 24C:
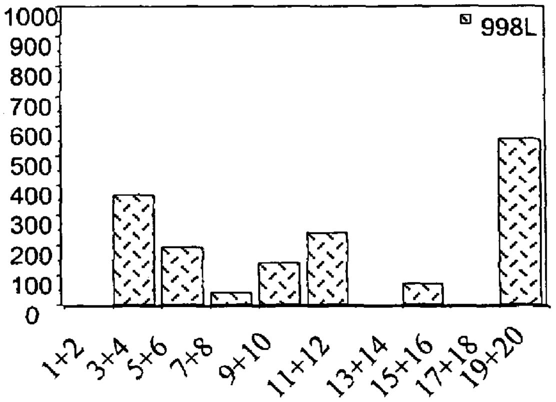
Figure 24D:
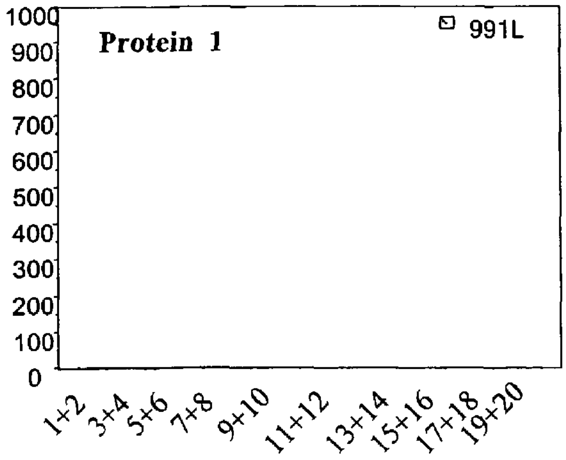
Figure 24E:
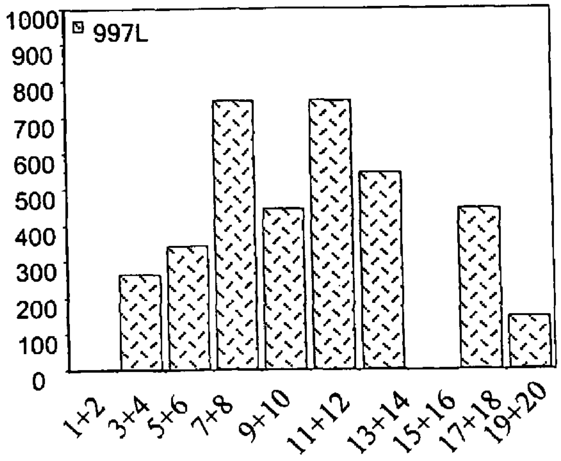
Figure 24F:
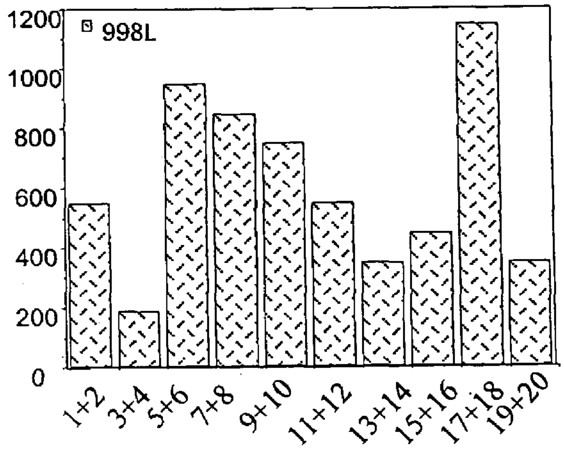
Figure 24G:
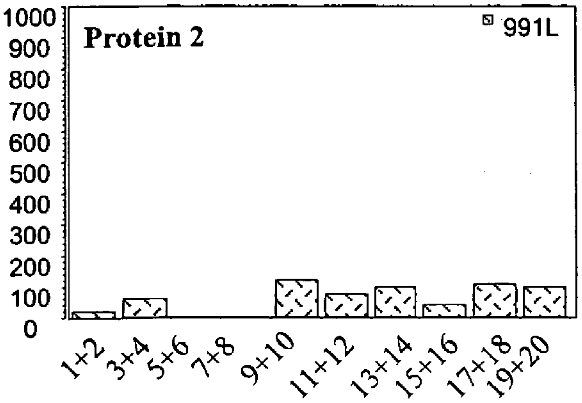
Figure 24H:
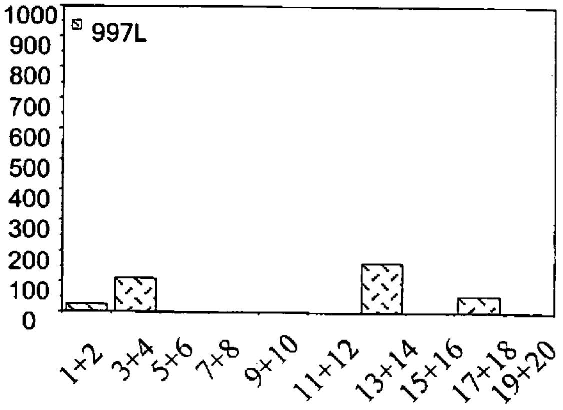
Figure 24I:
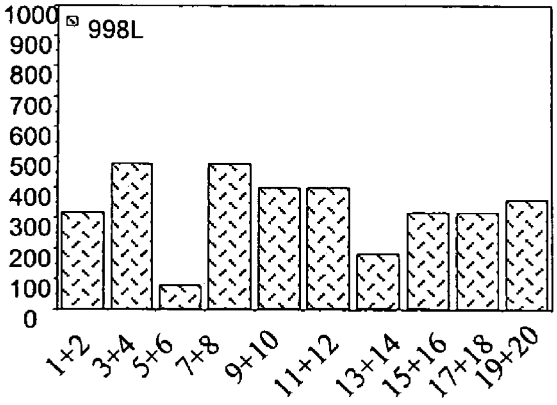
Figure 24J:
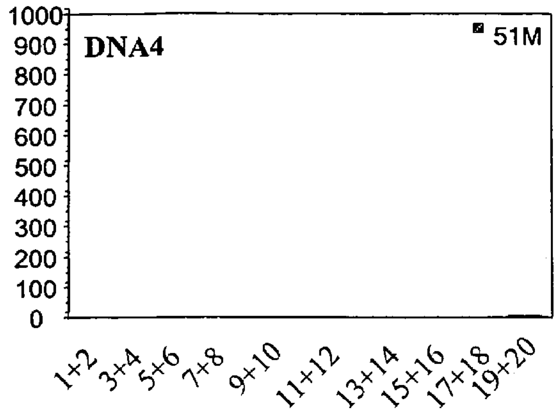
Figure 24K:
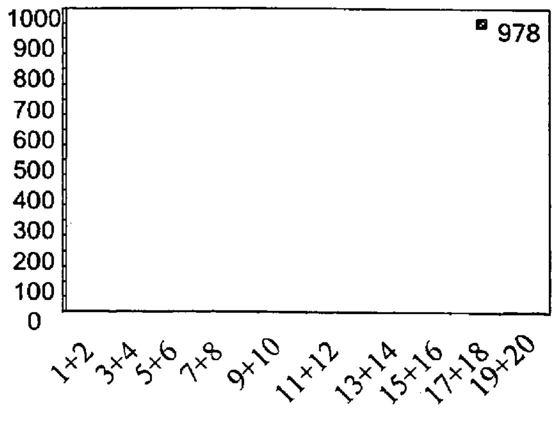
Figure 24L:
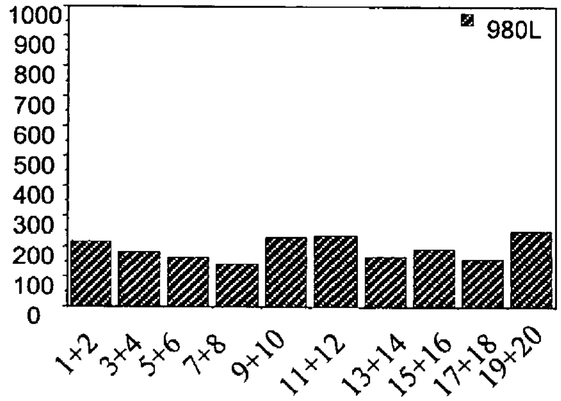
Figure 24M:
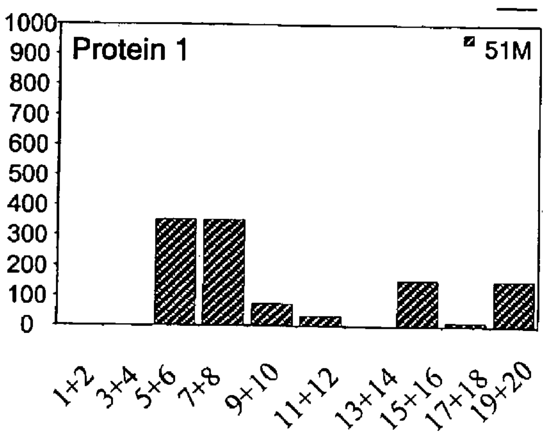
Figure 24N:
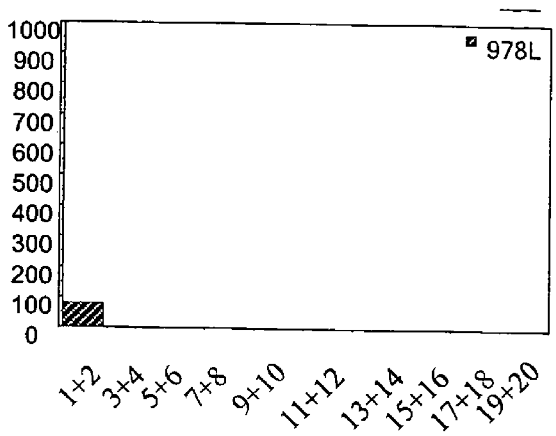
Figure 24O:
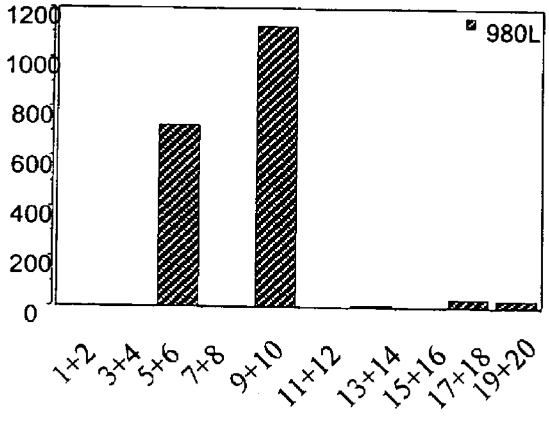
Figure 24P:
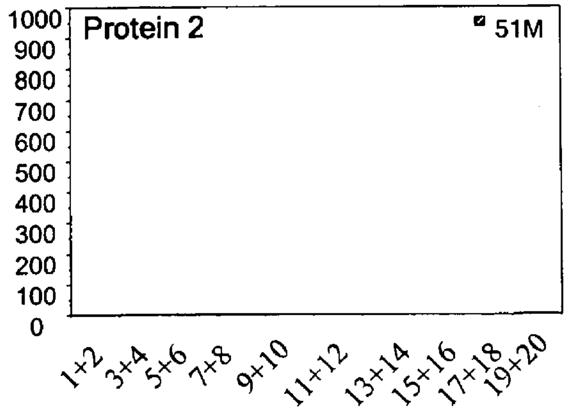
Figure 24Q:
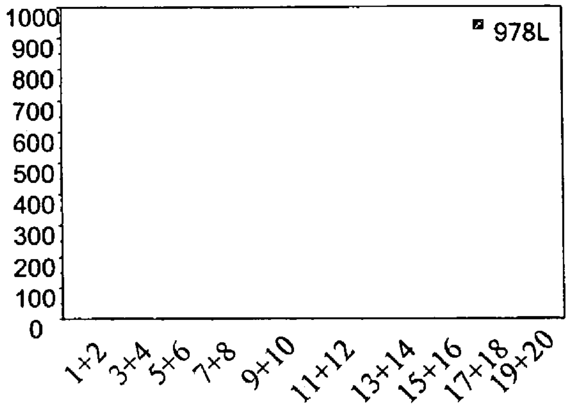
Figure 24R:
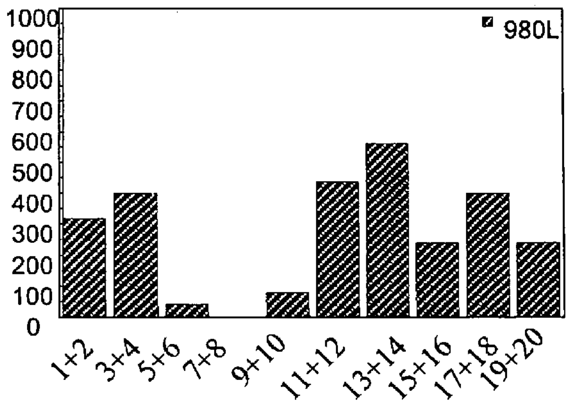

FIG. 23 demonstrates neutralization of a $SHIV_{Ba-L}$ isolate by sera from macaques after four DNA immunizations and gp120 boost. Four DNA immunizations did not elicit neutralizing activity against $SHIV_{Ba-L}$ isolate. However, sera from the immmunized animals collected after a gp120 boost were able to inhibit $SHIV_{Ba-L}$ infection. Serum collected after four DNA inoculations did not neutralize any of these isolates (data not shown). However, these homologous HIV-1 isolates were neutralized by sera after a protein boost. Neutralization titers of serum from these animals after the first protein boost against a number of homologous HIV-1 isolates are presented in Table 10. Sera after first protein boost were also tested for neutralization of a number of heterologous HIV-1 isolates, and the results are shown in Table 11. Additional neutralization assays were also conducted with serum collected after 4 DNA and first and second protein boosts against a broad range of primary HIV-1 isolates from clades A, B, C and E and the results are shown in Table 12.

TABLE 10

Neutralization Titers of Serum from Immunized Animals Collected after First Protein Boost Against Homologous HIV-1/SHIV Isolates

| Animal | Clade B $SHIV_{Ba-L}$[1] | Clade C $HIV\text{-}1_{Czm}$[1,2] | Clade B $HIV\text{-}1_{B715}$[1,2] |
|---|---|---|---|
| 51M | 82 | 83 | >1280 |
| 978L | 37 | 61 | >1280 |
| 980L | <10 | 38 | 89 |
| 991L | >160 | 44 | 952 |
| 997L | 41 | 46 | 840 |
| 998L | >160 | 54 | >1280 |

[1]Neutralization titers are calculated based on the dilution of immune serum inhibiting 50% of compared to untreated controls.
[2]Neutralization of $HIV\text{-}1_{Czm}$ and $HIV\text{-}1_{B715}$ were assayed by cell-to-cell transmission assay where CEM cells chronically infected with $HIV\text{-}1_{Czm}$ or $HIV\text{-}1_{B715}$ were cocultured with uninfected CEM cells in the presence of immune serum and syncytia were scored after 48 hrs.

TABLE 11

Neutralization Titers of Serum from Immunized Animals Collected after First Protein Boost against Heterologous HIV-1 Isolates

| Animal | MN clade B[1] | SF162 clade B[1] | Ba-L Clade B[2] | Bx08 clade B[2] | 6101 clade B[2] | 92RW020 clade A[2] | 92RW020 clade A[2] | Dul 79 clade C[2] | CM244 clade E[2] |
|---|---|---|---|---|---|---|---|---|---|
| 51M | 217 | 717 | 55 | 72 | 30 | 37 | 18 | 21 | 34 |
| 978L | 248 | 361 | 6 | 64 | 0 | 10 | 0 | 22 | 19 |
| 980L | 50 | 463 | 70 | 75 | 29 | 20 | 20 | 20 | 18 |
| 991L | 236 | 407 | 54 | 49 | 0 | 15 | 30 | 0 | 0 |
| 997L | 94 | 321 | 36 | 58 | 0 | 0 | 0 | 0 | 0 |
| 998L | 2455 | 4632 | 72 | 91 | 13 | 37 | 26 | 28 | 18 |

[1]Neutralization titers are calculated based on the dilution of immune serum inhibiting 50% of compared to untreated controls.
[3]Each serum was tested at 1:15 dilution for neutralization of indicated H1V-1 isolates using an indicator cell line. Percent inhibition was based on the degree of infection observed in the presence of immune serum compared to untreated controls as measured by chemiluminescence output.

TABLE 8-10

Neutralization of Primary HIV-1 Isolates by the Serum of Immunized Animals Collected after 4 DNA and First and Second Protein Boosts

| | | Neutralization of HIV-1 (% Inhibition of Infection) | | | | | | | | | |
|---|---|---|---|---|---|---|---|---|---|---|---|
| | Immune | Clade B | | | | Clade C | | | Clade A | | Clade E |
| Animal | Serum | SF162 | JRCSF | ADA | BAL | TV1 | DU151 | S007 | DJ263 | RW020 | CM235 |
| 51M | Post 4 DNA | 24 | 14 | 31 | −3 | 5 | 2 | −13 | 15 | −50 | −58 |
| | Post-1 Protein | 94 | 46 | 47 | 27 | 74 | 2 | −9 | 50 | 14 | −66 |
| | Post-2 Protein | 86 | 41 | 33 | 20 | 60 | 25 | −20 | 45 | 2 | −136 |
| 978L | Post 4 DNA | 33 | 29 | 18 | −34 | 21 | 2 | −8 | 35 | −26 | −19 |
| | Post-1 Protein | 79 | 33 | 39 | 7 | 18 | 11 | −7 | 40 | −37 | −61 |
| | Post-2 Protein | 64 | 81 | 28 | 8 | −44 | 9 | −16 | 51 | −13 | −130 |
| 980L | Post 4 DNA | 12 | 0 | 8 | −18 | −16 | 15 | 25 | 36 | −50 | −21 |
| | Post-1 Protein | 62 | 23 | 32 | 1 | 41 | 22 | 8 | 56 | −7 | −3 |
| | Post-2 Protein | 37 | −17 | 19 | −18 | −47 | 30 | 33 | 54 | −29 | −1 |
| 991L | Post 4 DNA | −37 | −34 | 33 | −37 | −34 | −9 | −35 | −21 | −17 | −68 |
| | Post-1 Protein | 76 | 32 | 59 | 3 | −34 | −2 | −23 | 26 | −57 | −51 |
| | Post-2 Protein | 44 | 13 | 46 | −23 | −99 | −31 | −31 | 25 | −101 | −153 |
| 997L | Post 4 DNA | 29 | −6 | 32 | −30 | −28 | −28 | 2 | 19 | −99 | −7 |
| | Post-1 Protein | 87 | 33 | 52 | 6 | −3 | 15 | 12 | 57 | −90 | −25 |
| | Post-2 Protein | 58 | 0 | 36 | −32 | 8 | 15 | 23 | 62 | −79 | −54 |
| 998L | Post 4 DNA | 51 | 0 | 20 | −31 | −9 | −10 | −9 | 16 | −67 | −68 |
| | Post-1 Protein | 96 | 82 | 63 | 59 | 67 | 20 | 3 | 68 | 16 | −90 |
| | Post-2 Protein | 85 | 76 | 46 | −11 | −2 | 5 | 2 | 56 | −33 | −122 |

Serum was tested at 1:5 dilution. Assay was conducted as described elsewhere (Mascola, et al., 2002, J. Virol. 76, 4810-4821).

The anti-Gag specific CMI response elicited by DP6-001 vaccine was assayed by ELISPOT for the production of IFN-γ. In this assay Gag peptide pools each containing six 15-mer peptides with 11 amino acid overlaps were used and two consecutive peptide pools were mixed for stimulation. Gag sequences were from an HIV-1 HXB-2 isolate. As shown in FIG. 24, a number of animals had anti-Gag-specific positive ELISPOT responses after four DNA immunizations, with ID inoculation appearing to be more effective than IM inoculation in inducing a cell mediated immune response.

Figures 25A, 25B:
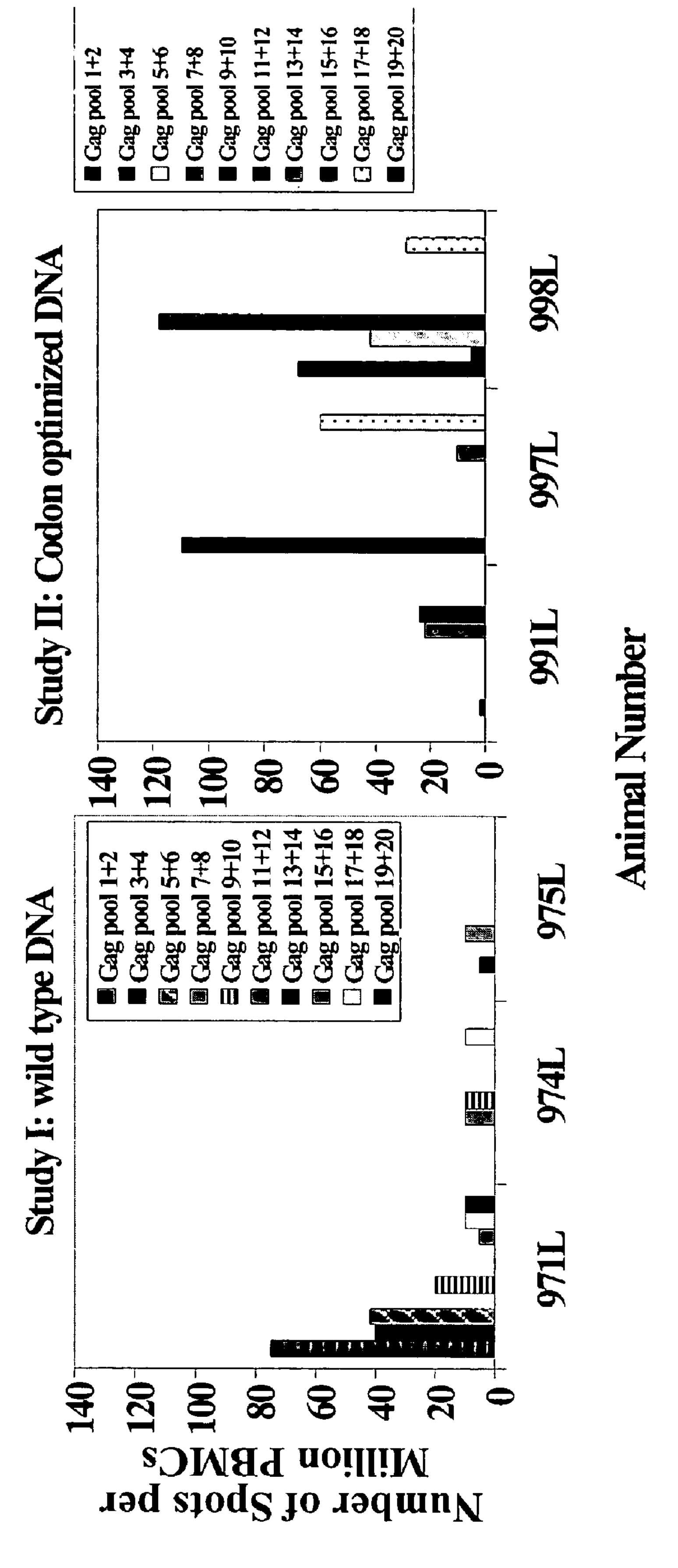
FIGS. 25A and 25B are a set of graphs depicting numbers of IFN-γ Expressing PBMC from macaques immunized with DNA formulations encoding wild type and codon optimized gag gene, in which PBMC were stimulated with Gag peptides. Comparison of IFN-γ expressing PBMC as measured by ELISPOT against Gag protein in macaques immunized with DNA encoding wild type and codon optimized gag gene by intradermal route (Study 1 in FIG. 25A, and Study 2 in FIG. 25B).

The anti-Gag specific CMI response elicited by wild type and codon optimized gag vaccines (Study 1 and Study 2) was also compared. As shown in FIG. 25, immunization of macaques with a codon-optimized gag gene elicits significantly higher ELISPOT response compared to DNA encoding wild type gag gene.

Figures 26A, 26B, 26C, 26D:
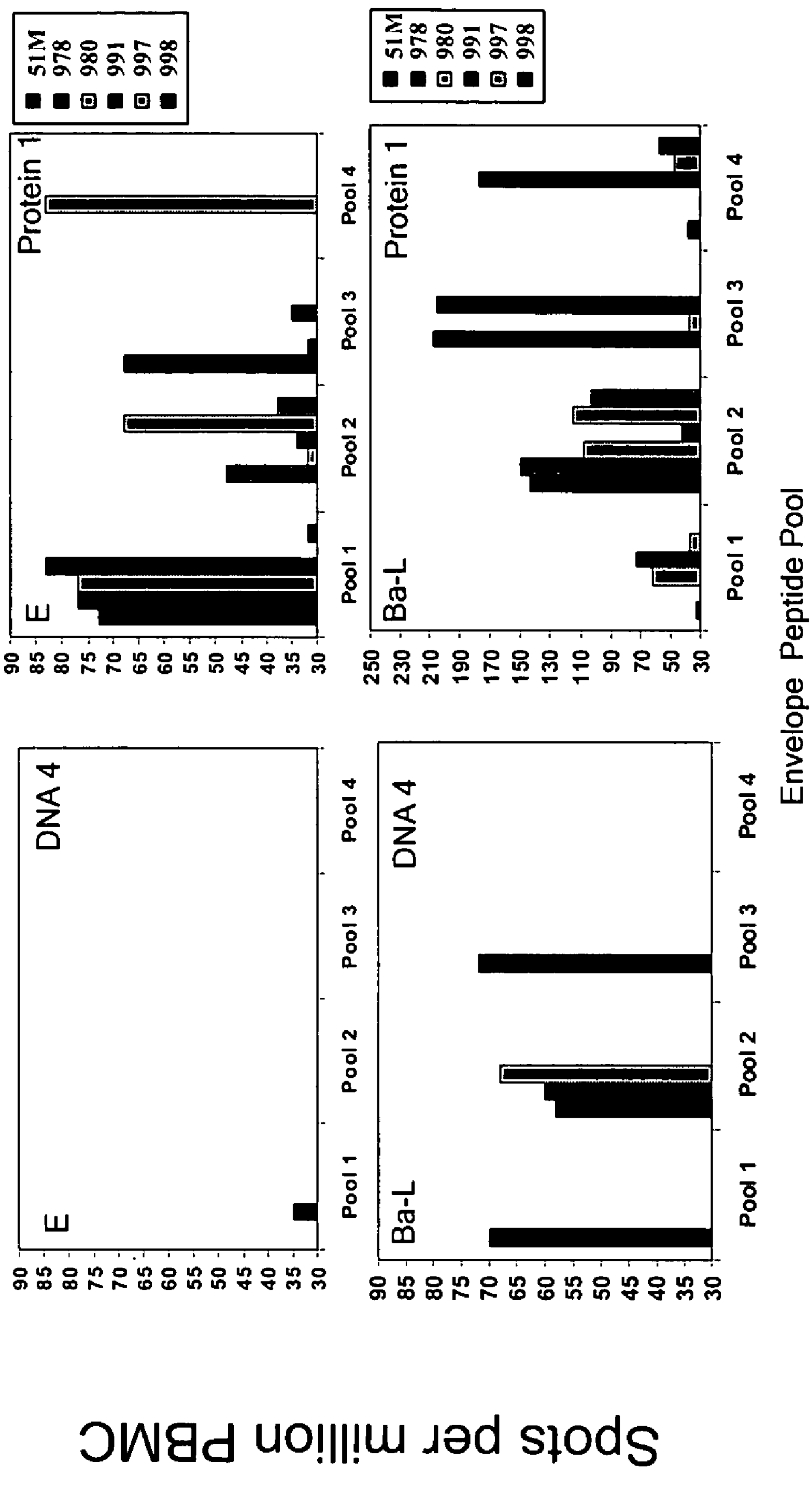
FIGS. 26A-26D are a set of graphs depicting numbers of IFN-γ expressing PBMC from macaques immunized with DNA/Protein formulations, in which the PBMC were stimulated with Clade E and Ba-L Env Peptides. ELISPOT assays were conducted using PBMC of macaques isolated after fourth DNA (DNA 4.

Anti-Env specific CMI responses elicited by the DP6-001 vaccine against Ba-L and clade E envelopes were assayed by ELISPOT for the production of IFN-γ. The results are shown in FIG. 26. Although a weak ELISPOT response was elicited in animals following four DNA immunizations, boosting of DNA primed animals with the polyvalent gp120 proteins markedly enhanced such response.

Immunization of macaques with DP6-001 DNA vaccines significantly primes the immune systems. Protein boosts are highly effective in eliciting a broad antibody response. CMI responses against the Gag antigen as measured by ELISPOT assay was observed following DNA immunization primarily by ID route. Taken together these results demonstrate that immunization of macaques with the DP6-001 vaccine elicits CMI and a broad binding antibody response, which is able to neutralize a number of HIV-1 isolates.

Example 14

DP6-001—63-day Repeat-Dose Intradermal or Intramuscular Biodistribution and Integration Study in New Zealand White Rabbits The biodistribution of DNA over a course of 64 days following single immunization of DNA via IM or ID route was examined. A total of 54 rabbits (27/sex) were used in this study. The animals were divided equally into three groups. Animals were initially accepted into the randomization pool based upon body weight and physical examination. They were assigned to study groups using computer-generated random numbers. At randomization, the mean body weight for each group was not statistically different from the control mean. Animals were assigned to three groups as shown in Table 13. Control animals (Group 1) were injected once with saline intradermally and intramuscularly. Group 2 animals were administered intramuscularly with a single dose of 7.2 mg of HIV Vaccine (Plasmid) DP6-001 (2.4 ml total at 1.2 ml per injection site), while Group 3 rabbits received a single immunization of 3.6 mg HIV Vaccine (Plasmid) DP6-001 via an intradermal route (1.2 mls total with 0.12 mls per injection site). The intramuscular dose was equally distributed between 2 injection sites on the left and right thigh muscles (1.2 ml administered per thigh). The intradermal dose was equally distributed between 10 injection sites, located in the dorsal area (approximately 0.12 ml per injection site). All injection sites were shaved and marked. The overall study design is described in Table 13.

TABLE 13

| Design of Study Conducted to Examine Biodistribution of DNA in Rabbits | | | | | | | | |
|---|---|---|---|---|---|---|---|---|
| | Test | Clinical | Dose | Dates of | | Dose Volume[3] | Number of Animals | |
| Group | Article | Dose | Mg | Dose | Route[2] | mL | Male | Female |
| 1 | Saline Control | | NA | SDI | IM/ID | 2.4/1.2 | 9 | 9 |
| 2 | DNA plasmid | IX | 7.2 | SDI | IM | 2.4 | 9 | 9 |
| 3 | DNA plasmid | IX | 3.6 | SDI | ID | 1.2 | 9 | 9 |

[2]IM: Intramuscular;
IM/ID: Intramuscular and Intradermal combination (Intramuscular and Intradermal route of administration will alternate between dates of dosing);
ID; Intradermal;
NA: Not applicable
[3]Dose Volume is constant regardless of animals' body weights Cageside observations included observations for mortality, moribundity, general health and signs of toxicity. Clinical observations included evaluation of skin and fur characteristics, eye and mucous membranes, respiratory, circulatory, autonomic and central nervous systems, and somatomotor and behavior patterns.

Six animals (three per sex per timepoint) were sacrificed on study day (SD) 8, 29, and 64 by sodium pentobarbital injection and the following tissues were removed, snap frozen in liquid nitrogen, and stored at −70±10°: blood (prior to euthanasia, ~1 mL was collected by puncture of the medial auricular artery into EDTA tubes, inverted several times and transferred into cryovial tubes); ovaries/testes; thymus; heart; lung; liver; gastrointestinal (small intestine section); kidney; spleen; subcutis (at intradermal injection site only); skin at intradermal injection site only (representative sample); intradermal injection site muscle, both sites (representative sample; an extra ~2 g sample was taken on SD 64 for integration analysis); intramuscular injection site muscle, both sites (an extra ~2 g sample was taken on SD 64 for integration analysis); contra lateral popliteal or mesenteric lymph node; bone marrow (isolated from the femur); and brain.

All tissues were processed (except skin samples) and analyzed by qPCR for the presence of the plasmids using a Good Laboratory Practice (GLP) validated method for biodistribution.

No test article-related changes in mortality, clinical signs of toxicity, body weights, body weight changes, or food consumption were observed. Biodistribution qPCR (Quantitative Polymerase Chain Reaction) analysis determined that the HIV Vaccine (Plasmid) DP6-001 was present in the muscle and subcutis at the intradermal injection sites and muscle at the intramuscular injection sites. Frequency of findings and copy number were greatest at the SD 8 necropsy and decreased progressively through the SD 29 and 64 necropsies. Only a few sporadic findings were evident in other tissues and these were considered the result of biological variation. Since the plasmid persisted at the intradernal and intramuscular injection sites through SD 64, integration analysis was performed on representative injection site muscle samples. Integration analysis was performed by extracting DNA from sites of administration and performing qPCR to determine if vaccine sequences were present in high molecular weight (i.e., chromosomal) DNA. If this assay tested positive, chromosomal DNA was extracted from the tissue and purified using field inversion gel electrophoresis, and retested for the presence of vaccine DNA. No integration was detected on samples for this study.

In summary, single intramuscular or intradermal injection of HIV Vaccine (Plasmid) DP6-001 in New Zealand White rabbits did not exhibit any obvious signs of toxicity under the study conditions used. The plasmid distributed into the intradermal injection site muscle, subcutis, and the intramuscular injection site muscle without any integration at the injection site.

Example 15

Tolerability and Safety of DP6-001

The tolerability and safety profile of the DP6-001 vaccine formulation was examined in the rabbit model. Since this vaccine formulation contains both DNA and protein components, the potential toxicity of both of these components was examined using the highest dose to be used in the phase I trials, with each animal receiving an additional inoculation compared to the clinical protocol. As proposed in the clinical trial, DNA was delivered either by IM or ID route whereas protein was inoculated by IM route in the toxicology study. Since protein immunization can be formulated with QS-21 adjuvant and with the excipient cyclodextrin, the potential toxicity of QS-21/cyclodextrin mixture was also examined in an additional arm of the study using the dose to be used in the clinical trial. The salient features of the toxicity study and the overall conclusions are discussed below.

The potential toxicity of a plasmid prime and protein boost HIV Vaccine DP6-001 when administered repeatedly at multiple dose levels by the intramuscular or intradermal route during a 26-week study period to male and female New Zealand rabbits were examined. The rabbit model was selected because it is recommended by FDA for use in vaccine preclinical studies. The intramuscular and intradermal routes of immunization were selected since these are the potential routes for administration to humans. The DNA vaccine component is a mixture of six different DNA plasmids in equal concentrations expressing six different HIV protein variants and was used for the DNA prime phase of the study. The protein component of the DP6-001 vaccine is a mixture of five different proteins in equal concentrations expressing five different HIV protein variants and was used for the protein boost phase of the study. The dose (7.2 mg of pooled DNA) selected for the plasmid immunogens to be delivered intramuscularly were based on expected clinical dose. However, for intradermal immunization, toxicity dose (3.6 mg) of plasmid DNA was three times the proposed clinical dose. The protein dose used in toxicity study was comparable to the clinical dose.

Animals were initially accepted into the randomization pool based upon body weight and physical examination. They were assigned to study groups using computer-generated random numbers. At randomization the mean body weight for each group was not statistically different from the control mean. Animals were assigned to groups as shown in Table 14.

TABLE 14

Design of Toxicology Study Conducted with DP6-001 Vaccine

| Group | Test Article | Clinical Dose[1] | Dose[2] mg | Dates of Dose | Route[3] | Dose Volume[4] ml | Number of Animals Male | Number of Animals Female |
|---|---|---|---|---|---|---|---|---|
| 1 | Saline Control | IX | NA | SD | IM/ID | 2.4/1.2 | 8 | 8 |
| | PBS Control | IX | | SD | IM | 1.0 | | |
| 2 | Saline Control | IX | NA | SD | IM/ID | 2.4/1.2 | 8 | 8 |
| | PBS Control | IX | | SD | IM | 1.0 | | |
| 3 | QS-21 | IX | NA | SD | IM | 1.0 | 10 | 10 |
| 4 | DNA plasmid | IX | 7.2 | SD | ID | 2.4 | 5 | 5 |
| 5 | DNA plasmid | 3X | 3.6 | SD | ID | 1.2 | 5 | 5 |
| | DNA plasmid | IX | 7.2 | SD | IM | 2.4 | 5 | 5 |
| | Protein | IX | 0.375 | SD | | 1.0 | | |
| 7 | DNA plasmid | 3X | 3.6 | SD | ID | 1.2 | 5 | 5 |
| | Protein | IX | 0.375 | SD | IM | 1.0 | 5 | 5 |
| 8 | DNA plasmid | IX | 7.2 | SD | IM | 2.4 | 5 | 5 |
| 9 | DNA plasmid | 3X | 3.6 | SD | ID | 1.2 | 5 | 5 |
| 10 | DNA plasmid | IX | 7.2 | SD | IM | 2.4 | 5 | 5 |
| | Protein | IX | 0.375 | SD | | 1.0 | | |
| 11 | DNA plasmid | 3X | 3.6 | SD | ID | 1.2 | 5 | 5 |
| | Protein | IX | 0.375 | SD | IM | 1.0 | | |

[1]The values supplied are the multiple of the highest expected human clinical dose

[2]Protein to be given with QS-21 at 50 μg and cyclodextrin at 30 mg

[3]IM: Intramuscular;

IM/ID; Intramuscular and Intradermal combination (Intramuscular and Intradermal route of administration will alternate between dates of dosing);

UDL: Intradermal;

NA: Not Applicable

[4]Dose Volume is constant regardless of the animals' body weights

The dose administration scheme for both DNA and protein immunogens are shown in Table 15.

TABLE 15

| Dose Administration Scheme of DNA and Protein Immunogens in Toxicology Study | |
|---|---|
| Route of Administration | Intramuscular, Intradermal, or combination<br>Intramuscular and Intradermal (alternated between dates of dosing starting with Intramuscular) |
| Frequency of Dosing | Once daily on SD 1, 29, 57, 85, 113, 141, 169 as designated in Table 14 |
| Dose Volume | Plasmid IM: 2.4 mL split between two dosing sites<br>Protein IM: 1.0 mL into one site Plasmid ID: 1.2 split between 10 dosing sites |
| Dose Sites[a] | Intramuscular: right and left thighs for plasmid and right thigh for protein<br>Intradermal: dorsal scapular area |
| Equipment | Intramuscular: 23 gauge, 5/8 inch needle with 3 mL syringe<br>Intradermal: 0.5 mL syringe with 27 gauge 1/8 inch needle |
| Dosing Conditions | Formulations were maintained on wet ice until administered |

[a]Injections were administered at a shaved/marked site. The sites were re-shaved and re-marked as needed.

IM—Intramuscular

ID—Intradermal

New Zealand White rabbits (5/sex/group minimum) received intramuscular (2.4 ml dose volume, resulting in a 7.2 mg/animal dose) or intradermal (1.2 ml dose volume, resulting in a 3.6 mg/animal dose) administration of the DP6-001 HIV DNA vaccine or saline control on Study Day (SD) 1, 29, 57, and 85. For the protein boost phase of the study, rabbits received intramuscular (1.0 ml dose volume, resulting in a 0.375 mg/animal dose) administration of the DP6-001 HIV protein vaccine, Phosphate Buffered Saline control, or QS-21 and cyclodextrin adjuvant control (50 μg and 30 mg per injection, respectively) on SD 113, 141, and 169. Animals were then necropsied on SD 87 (acute DNA necropsy), SD 99 (recovery DNA necropsy), SD 171 (acute protein necropsy) or SD 183 (recovery protein necropsy). Parameters evaluated included mortality, clinical observations, draize observations, body weights, food consumption, clinical pathology, organ weights, gross pathology, and histopathology. Binding antibody titers elicited by DNA and protein immunizations were also measured.

No test article-related changes in mortality, clinical observations, body weights, food consumption, organ weights, clinical pathology findings, gross observations, and histopathology were observed. Both DNA priming and protein boosts elicited strong serum antibody response as measured by ELISA. An increased frequency of recoverable Draize findings at the intradermal DNA vaccine injection site was observed. Some specific observations made under each parameter examined are given below.

Mortality and clinical observations: Treatment with HIV Vaccine DP6-001 did not result in mortality, and had no effect on clinical observations or cageside observations. One Group 3 male had an abrasion on the nose on SD 64 and 78. One Group 10 male had swelling of the scrotum on SD 92 that was not observed in any other Group 10 or Group 6 animals. One male in each of Groups 3, 4, 5, 7, 9, and 10 was observed as being thin at various times during the study. These observations resolved within three weeks or less of the first observation, and the low incidence suggested a lack of any test article effect. One Group 1 male animal was found to have abrasions/abscesses on the front and rear paws. Since this was a control animal, these finding were not considered test article-related. Due to these abscesses, the animal had appetite loss and was observed as pale during this period. Several animals had intermittent observations of lacrimation throughout the study.

Draize Observations: Intramuscular treatment with HIV Plasmid Vaccine DP6-001 had no effect on dermal observations. For the Intramuscular injections of plasmid (treated sites 1 and 2), primarily minimal erythema and edema scores were seen, with the exception of a few mild scores. Since these observations were also seen in the control groups (Groups 1 and 2), they were not considered test article-related and were attributed to the injection procedure.

Intradermal treatment with HIV Plasmid Vaccine DP6-001 had an effect on dermal observations. For the intradermal plasmid administration (treated site 3), erythema and edema scores for the controls (Groups 1 and 2 on SD 29 and 85) reached mild levels of intensity. For groups 5, 7, 9, and 11, the intensity and frequency of observations were increased as compared to the controls, suggesting a test article-mediated increase in dermal reactivity. However, while test article mediated, these observations did recover with time.

For Intramuscular injection with HIV Protein Vaccine DP6-001, minimal to mild findings for erythema and edema were evident in the control (Groups 1-3) and protein immunized groups (Groups 6, 7, 10, and 11). Since the findings were comparable between control and protein immunized groups, these were not considered to be test article related and were instead attributed to the injection procedure.

Body weight and food consumption: No treatment-related effects on body weight or body weight gains gains were observed in any groups. Further there were no treatment-related effects on food consumption in any group.

Clinical Pathology: There were no apparent test article-related effects due to repeated multiple dose levels of HIV vaccine DP6-001 in the rabbit. The higher globulin observed in some groups on SD31 and 87 were very slight and may be due to antibody production, but were most likely due to individual animal variation. All other minor changes were attributed to individual animal variation, and they had no biological significance.

Hematology, clinical chemistry, coagulation: No statistical differences between control and immunized groups were noted and all differences were due to individual animal variation.

Gross Pathology: There were no treatment-related effects on gross pathology. Since there were no histopathological correlates, no dose response was observed, and most of the findings seen were also seen in the control animals, these findings were not considered test article related.

Organ Weights: There were no treatment-related changes in organ weights in any group. Statistically significant changes in organ weights, organ to body weight, and organ to brain weight ratios include: a decrease in the brain weight of the Group 4 females on SD 87, decrease in the thymus weight of the Group 3 females on SD 171, decreases in the adrenal, heart, and spleen weights of the Group 3 females on SD 183, and a decrease in the spleen to body weight ratio and heart to brain weight ratio of the Group 3 females on SD 183. These changes were not considered to be test article-related since no obvious pattern was observed and they involve changes in tissue weights or ratios in the Group 3 adjuvant control animals as compared to the Group 1 or 2 saline control.

Histopathology: There were no treatment-related effects on histopathology in any Groups.

Inflammatory responses, foreign material, and occasional hemorrhage observed at injection sites were considered related to the dosing procedure. There were no histopathological changes considered to be toxic effects of the administration of the test article(s) or vehicle(s). Findings at injection sites included inflammatory cellular infiltration or inflammation at minimal and mild severities, with infrequent hemorrhage and comparatively low incidence of focal refractive deposits of foreign material. These findings occurred in both control and treated rabbits, with no apparent treatment group-related differences and all were considered to be related to dosing procedures.

In kidneys, nephropathy (recognized as scattered microfoci of tubular epithelial cell regenerative and/or degenerative changes with tubular disorganization, hyperchromatic cells, tubular cell vacuolization, and the collection of pale flocculent material and cellular debris in lower segments of collecting tubules) was seen at minimal severity across all groups. Multifocal tubular mineralization or tubular cell vacuolization occurred separately or in combination with nephropathy. These renal findings are typical of spontaneous pathology in kidneys of New Zealand White rabbits of this age; they showed no apparent relationship to administration of the test article(s).

Fatty change and vacuolation of hepatocytes as well as focal mixed cell or mononuclear cell infiltrate(s) in the liver correlated microscopically with enlargement and discoloration observed grossly. These hepatic findings occur spontaneously in rabbits, and were seen without apparent relationship to dosage.

The sporadic occurrence of hemosiderin deposits in the spleen, focal inflammatory responses in the lung, fatty change in the subepicardium of the heart, and other low incidence sporadic findings in other organs showed no apparent relationship to dose and were considered unrelated to test article administration.

Therefore, under these study conditions, repeat intramuscular administration of HIV Vaccine DP6-001 to New Zealand White rabbits did not exhibit any specific signs of systemic toxicity but resulted in reversible Draize observations at the injection site.

Example 16

Phase I Clinical Study of DP6-001

Human clinical trials are conducted for the purpose of determining safety of a vaccine and for determining efficacy of a vaccine. To determine safety, normal volunteers are immunized with the vaccine. The incidence of side effects is noted. To determine efficacy, NIH established protocols are followed. High-risk population (e.g., drug users, populations with high-risk sexual activity, populations in which the incidence of HIV is high). To test a high risk population, the incidence of HIV infection in the negative control group who are immunized with a DNA vaccine containing the vector alone is compared to the incidence of HIV infection in the test group receiving the polyvalent DNA vaccine containing primary isolate sequences (e.g., sequences of gp120, gp140, gp160 and/or gp41). A double blind trial is conducted. The immunization regimen is, for example, three DNA vaccine immunizations by gene gun, each administered a month apart. Sera are drawn during the regimen to monitor immune status by experiments such as described in Examples 2-4, above. Additionally, cell-mediated immunity (CTL response) is tested in human patients by isolating PBMCs followed by in vitro functional testing of these cells as described for splenocytes in Example 4, above. The presence of neutralizing antibodies in the patient's sera is then tested as described in Example 3, above. Infection by HIV is tested and statistical analysis is done to determine if the incidence is significantly different between control and test groups.

A phase I clinical study to assess DP6-001 is conducted as follows. The objectives of the study are to assess the safety of multiple dosing levels of DP6-001, to assess the ability of DP6-001 to induce humoral immune responses to vaccine components, and to assess the ability of DP6-001 to induce cell-mediated immune responses.

Approximately 36 human subjects participate in the study. These subjects are healthy, HIV-uninfected adult volunteers of 18-55 years of age. They are at low or minimal risk for HIV infection as defined by HVTN Risk Status. They have no history of previous experimental HIV vaccine inoculations.

Each participant receives one of three dose regimes in which DP6-001 is administered via ID or IM routes. Administration is randomized, with a rising DNA component, multiple doses, with a follow-on protein vaccine boost. One test program of administration to humans is as follows: administer approximately 50 μg/kg of the DP6-001 DNA composition at week 0, week 4, and week 12, (i.e., 3 doses per person, approx. 2.5 mg dose for a person of 50 kg); and administer 7 μg/kg of the DP6-001 protein composition at week 20 and week 28.

To assess the ability of DP6-001 to induce humoral responses to vaccine components, ELISA is performed using a pool of the gp120 glycoproteins used for vaccination. ELISA using HIV-1 Czm Gag protein is also performed. Neutralizing antibody assays against panels of laboratory adapted and primary HIV-1 isolates are performed by HVTN-certified laboratories. Additional solid-phase assays such as Western blots, can be used to further confirm immunity and characterize immune responses and distinguish between vaccination and potential new infection. For example, if the vaccine does not include gp41, the vaccinated subject would not exhibit a response to gp41. Detection of gp41-reactivity in the subject would then be indicative of potential new infection.

To assess the ability of DP6-001 to induce cell-mediated immune responses, IFN-γ ELISPOT assays specific for HIV-1 Gag or Env epitopes can be performed. Bulk culture cytotoxic T-cell assays and flow cytometric intracellular cytokine staining assays can also be used.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of inducing an immune response against human immunodeficiency virus (HIV) or an HIV epitope in a primate, the method comprising:

administering to the primate a nucleic acid composition comprising (a) at least four sets of nucleic acid molecules encoding wild-type HIV gp120 envelope glycoproteins, wherein the sets of nucleic acid molecules encode glycoproteins from primary isolates B715, Ba-L, and Czm, and from a clade E primary isolate, and (b) a set of nucleic acid molecules encoding a wild-type HIV gag protein from a primary isolate; and thereafter administering to the primate a protein composition comprising a plurality of sets of isolated wild-type HIV envelope glycoprotein molecules of each of the primary isolates in (a), wherein the nucleic acid composition and the protein composition are administered in amounts sufficient to induce an immune response against HIV or an HIV epitope in the primate.

2. The method of claim 1, further comprising isolating immune cells from the primate; and testing an immune response of the isolated immune cells in vitro.

3. The method of claim 1, wherein the protein composition is administered between 4 and 8 weeks after the nucleic acid composition.

4. The method of claim 1, further comprising testing for a cell-mediated immune response.

5. The method of claim 1, further comprising testing for a humoral immune response.

6. The method of claim 5, wherein a neutralizing humoral response is tested.

7. The method of claim 1, wherein a cell-mediated immune response is induced.

8. The method of claim 1, wherein a humoral immune response is induced.

9. The method of claim 8, wherein a neutralizing humoral immune response is induced.

10. The method of claim 1, wherein the nucleic acid molecules comprise DNA plasmids.

11. The method of claim 1, wherein one or more of the sets of nucleic acid molecules comprises optimized codons.

12. The method of claim 1, wherein the set of nucleic acid molecules encoding the gag protein comprises optimized codons.

13. The method of claim 1, wherein the protein composition is administered with an adjuvant.

14. The method of claim 13, wherein the adjuvant is QS-21.

15. The method of claim 1, wherein the clade E primary isolate is 93TH976.17.

16. The method of claim 1, wherein the wild-type HIV gag protein is a gag protein of NL4-3.

17. A method of inducing an immune response against human immunodeficiency virus (HIV) or an HIV epitope in a human, the method comprising:

administering to the human a nucleic acid composition comprising (a) at least four sets of nucleic acid molecules encoding wild-type HIV gp120 envelope glycoproteins, wherein the sets of nucleic acid molecules encode glycoproteins from primary isolates B715, Ba-L, and Czm, and from a clade E primary isolate, and (b) a set of nucleic acid molecules encoding a wild-type HIV gag protein from a primary isolate; and thereafter administering to the human a protein composition comprising a plurality of sets of isolated wild-type HIV envelope glycoprotein molecules of each of the primary isolates in (a), wherein the nucleic acid composition and the protein composition are administered in amounts sufficient to induce an immune response against HIV or an HIV epitope in the human.

18. The method of claim 17, wherein the nucleic acid composition further comprises a set of nucleic acid molecules encoding gp120 envelope glycoprotein of a primary isolate from clade A, and the protein composition further comprises a set of isolated envelope glycoprotein molecules of a primary isolate from clade A.

19. The method of claim 18, wherein the clade A primary isolate is 92UG037.8.

20. The method of claim 17, wherein the clade E primary isolate is 93TH976.17.

21. The method of claim 17, wherein the wild-type HIV gag protein is a gag protein of a Czm isolate.

22. The method of claim 17, further comprising isolating immune cells from the human; and testing an immune response of the isolated immune cells in vitro.

23. The method of claim 17, wherein the protein composition is administered between 4 and 8 weeks after the nucleic acid composition.

24. The method of claim 17, further comprising testing for a cell-mediated immune response.

25. The method of claim 17, further comprising testing for a humoral immune response.

26. The method of claim 25, wherein a neutralizing humoral response is tested.

27. The method of claim 17, wherein a cell-mediated immune response is induced.

28. The method of claim 17, wherein a humoral immune response is induced.

29. The method of claim 28, wherein a neutralizing humoral immune response is induced.

30. The method of claim 17, wherein the nucleic acid molecules comprise DNA plasmids.

31. The method of claim 17, wherein one or more of the sets of nucleic acid molecules comprises optimized codons.

32. The method of claim 17, wherein the set of nucleic acid molecules encoding the gag protein comprises optimized codons.

33. The method of claim 17, wherein the protein composition is administered with an adjuvant.

34. The method of claim 33, wherein the adjuvant is QS-21.

* * * * *

UNITED STATES PATENT AND TRADEMARK OFFICE

CERTIFICATE OF CORRECTION

PATENT NO. : 7,901,690 B2
APPLICATION NO. : 10/728195
DATED : March 8, 2011
INVENTOR(S) : Shan Lu et al.

It is certified that error appears in the above-identified patent and that said Letters Patent is hereby corrected as shown below:

Column 1, line 13:

Add:

STATEMENT AS TO FEDERALLY SPONSORED RESEARCH

This invention was made with government support under grant no. AI040337 awarded by the National Institutes of Health. The government has certain rights in the invention.

Signed and Sealed this
Nineteenth Day of April, 2011

David J. Kappos
*Director of the United States Patent and Trademark Office*

UNITED STATES PATENT AND TRADEMARK OFFICE

CERTIFICATE OF CORRECTION

PATENT NO. : 7,901,690 B2
APPLICATION NO. : 10/728195
DATED : March 8, 2011
INVENTOR(S) : Shan Lu et al.

It is certified that error appears in the above-identified patent and that said Letters Patent is hereby corrected as shown below:

Title Page, Item (56) column 2 (other publications), line 7:
delete "immunodeficiecy" and replace with -- immunodeficiency --.

Title Page, Item (56) column 2 (other publications), lines 40-42:
After "2009;4(2):e4505.*" delete "Haynes "Critical issues in mucosal immunity for HIV-1 vaccine development" (J. Allergy Clin Immunol. 122:3-9,2008).*" and insert the same on Page 1, Col. 2, Line 41 as a new entry.

Item (57) column 2 (abstract), line 3:
delete "composition" and replace with -- compositions --.

Item (57) column 2 (abstract), line 11:
delete "fro" and replace with -- for --.

Signed and Sealed this
Tenth Day of May, 2011

David J. Kappos
*Director of the United States Patent and Trademark Office*

UNITED STATES PATENT AND TRADEMARK OFFICE

CERTIFICATE OF CORRECTION

PATENT NO. : 7,901,690 B2
APPLICATION NO. : 10/728195
DATED : March 8, 2011
INVENTOR(S) : Lu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this
Twenty-sixth Day of July, 2011

David J. Kappos
*Director of the United States Patent and Trademark Office*

SEQUENCE LISTING

```
<160> NUMBER OF SEQ ID NOS: 21

<210> SEQ ID NO 1
<211> LENGTH: 30
<212> TYPE: DNA
<213> ORGANISM: Artificial Sequence
<220> FEATURE:
<223> OTHER INFORMATION: PCR primer

<400> SEQUENCE: 1

cttgtgggtc acagtctatt atggggtacc                                    30


<210> SEQ ID NO 2
<211> LENGTH: 35
<212> TYPE: DNA
<213> ORGANISM: Artificial Sequence
<220> FEATURE:
<223> OTHER INFORMATION: PCR primers

<400> SEQUENCE: 2

ggtcggatcc ttactccacc actcttctct ttgcc                              35


<210> SEQ ID NO 3
<211> LENGTH: 35
<212> TYPE: DNA
<213> ORGANISM: Artificial Sequence
<220> FEATURE:
<223> OTHER INFORMATION: PCR primer

<400> SEQUENCE: 3

cgacggatcc ttatgttatg tcaaaccaat tccac                              35
```

-continued

<210> SEQ ID NO 4
<211> LENGTH: 47
<212> TYPE: DNA
<213> ORGANISM: Artificial Sequence
<220> FEATURE:
<223> OTHER INFORMATION: PCR primer

<400> SEQUENCE: 4
gtcgctccgc tagcgcagtg ggaataggag ctgtgttcct tgggttc 47

<210> SEQ ID NO 5
<211> LENGTH: 1485
<212> TYPE: DNA
<213> ORGANISM: Human immunodeficiency virus

<400> SEQUENCE: 5
atgggtgcga gagcgtcaat attaagaggg ggaaaattag ataaatggga aaaaattagg 60
ctaaggccag gggggaaagaa acgctatatg ataaaacacc tagtatgggc aagcagggag 120
ctggaaagat ttgcgcttaa ccctggcctt ttagaaacat cagaaggctg taaacaaata 180
atgaaacagc tacaaccagc tcttcagaca ggaacggagg aacttagatc attatacaac 240
acagtagcaa ctctctattg tgtacatgaa ggggtagagg tacgagacac caaggaagcc 300
ttagacagga tagaggaaga acaaaacaaa attcagcaaa aaatacagca aaaaacacag 360
caagcggctg acggaaaggt cagtcaaaat tatcctatag tgcagaatct ccaagggcaa 420
atggtacacc agaaactatc acctagaact ttgaatgcat gggtaaaagt aatagaagaa 480
aaagctttta gcccagaggt aatacccatg tttacagcat tatcagaagg agccacccca 540
caagatttaa acaccatgtt aaatacagtg gggggacatc aagcagccat gcaaatgtta 600
aaagatacta tcaatgagga ggctgcagaa tgggatagat tacatccagt gcatgcaggg 660
cctattgcac caggccaaat gagagaacca aggggaagtg atatagcagg aactactagt 720
accctccaag aacagatagc atggatgaca agtaatcccc ctattccagt gggagacatc 780
tataaaagat ggataattct ggggttaaat aaaatagtaa gaatgtatag ccctgtcagc 840
attttggaca taaaacaagg gccaaaggaa ccctttagag actatgtaga ccggttcttc 900
aaaactttaa gagctgaaca ggctacacaa gaagtaaaaa attggatgac agacaccttg 960
ttggtccaaa atgcaaaccc agattgcaag accattttaa aagcattagg accaggggct 1020
acattagaag aaatgatgac agcatgtcaa ggagtgggag gacctagcca caaagcaaga 1080
gtgttggctg aggcaatgag ccaaacaaat agtgtaaaca tactgatgca gaaaagcaat 1140
tttaaaggaa ataaaagaat ggttaaatgt tttaactgtg gtaaggaagg gcacatagcc 1200
agaaattgca gggcccctag gaaaaagggc tgttggaaat gtggaaagga gggacaccaa 1260
atgaaagact gtactgagag gcaggctaat tttttaggga aaatttggcc ttcccacaag 1320
ggaaggccag ggaatttcct tcagaacagg ccagagccaa cagccccacc agcagagagc 1380
ttcaggttcg aggagacaac ccccgctccg aagcaggagt cgaaagacag ggaagcctta 1440
acttccctca aatcactctt tggcagcgac cccttgtctc aataa 1485

<210> SEQ ID NO 6
<211> LENGTH: 1485
<212> TYPE: DNA
<213> ORGANISM: Artificial Sequence
<220> FEATURE:
<223> OTHER INFORMATION: Codon optimized Gag.Czm DNA sequence

<400> SEQUENCE: 6
atgggagcca gagccagcat cctgagagga ggcaaactgg acaagtggga gaagattaga 60

```
ctgcggcctg gaggcaagaa acggtacatg atcaagcacc tggtgtgggc cagcagagag     120
ctggagcggt tcgcactgaa tcctggcctc ctggagacca gcgaaggatg caaacagatc     180
atgaagcagc tccaaccagc tctgcagacc ggcactgagg aactgagaag cctgtacaac     240
accgtggcca ccctgtactg cgtgcacgag ggcgtggaag tgcgggacac caaggaggcc     300
ctggaccgga tcgaggaaga gcagaacaag atccagcaaa agatccagca gaagacccaa     360
caggccgctg atggaaaggt gagccagaac taccccatcg tccagaacct ccagggccag     420
atggtgcacc agaagctgag ccctcggaca ctgaacgcct gggtcaaggt gatcgaagag     480
aaggccttca gccctgaagt gatccccatg ttcacagctc tgagcgaagg cgccactcct     540
caggacctga acaccatgct gaacaccgtg ggaggccacc aagctgcaat gcagatgctg     600
aaggacacca tcaacgagga agctgccgag tgggacagac tgcatccagt ccacgccgga     660
cccatcgctc ctggccagat gcgggaacct agaggaagcg atatcgctgg cactacctcc     720
accctgcaag agcagatcgc ttggatgacc agcaaccccc ctatccccgt cggcgacatc     780
tacaagcggt ggatcatcct gggcctgaac aagatcgtga gaatgtacag ccccgtgagc     840
atcctggaca tcaagcaagg acctaaggag cccttcagag actacgtcga ccggttcttt     900
aagactctga gagccgagca ggcaacccag gaggtgaaga actggatgac cgacacactg     960
ctggtccaga acgccaaccc cgactgcaag accatcctga aggctctggg acccggcgcc    1020
acactggaag agatgatgac agcatgccag ggcgtcggag gaccaagcca caaagcaaga    1080
gtgctcgccg aggccatgag ccagaccaac agcgtgaata tcctgatgca gaagagcaac    1140
ttcaaaggca acaagcggat ggtcaagtgc ttcaactgtg gcaaggaagg acacatcgca    1200
cggaactgca gagctccacg gaagaaaggc tgctggaagt gcggcaagga aggacaccag    1260
atgaaggact gcacagagcg gcaagcaaac ttcctcggaa agatctggcc aagccacaag    1320
ggaagacccg gcaatttcct gcagaacaga cctgagccca ccgcccccacc tgctgagagc    1380
ttccggttcg aagagaccac acccgccccc aagcaggaga gcaaggacag agaagcactg    1440
accagcctga agagcctgtt cggcagcgat cccctgagcc agtga                    1485
```

<210> SEQ ID NO 7
<211> LENGTH: 1422
<212> TYPE: DNA
<213> ORGANISM: Human immunodeficiency virus

<400> SEQUENCE: 7

```
ttgtgggtca cagtctatta tggggtacct gtgtggaaag aagcaaccac cactctattt      60
tgtgcatcag atgctaaagc atatgataca gaggtacata atgtttgggc cacacatgcc     120
tgtgtaccca cagaccccaa cccacaagaa gtagaattgg aaaatgtgac agaaaatttt     180
aacatgtgga aaaataacat ggtagaacag atgcatgagg atataatcag tttatgggat     240
caaagcctaa agccatgtgt aaaattaact ccactctgtg ttactttaaa ttgcactgat     300
ttgaggaatg ctactaatgg gaatgacact aataccacta gtagtagcag ggaaatgatg     360
gggggaggag aaatgaaaaa ttgctctttc aaaatcacca caaacataag aggtaaggtg     420
cagaaagaat atgcactttt ttatgaactt gatatagtac caatagataa taatagtaat     480
aatagatata ggttgataag ttgtaacacc tcagtcatta cacaggcctg tccaaagata     540
tcctttgagc caattcccat acattattgt gccccggctg gttttgcgat tctaaagtgt     600
aaagataaga agttcaatgg aaaaggacca tgttcaaatg tcagcacagt acaatgtaca     660
catgggatta ggccagtagt atcaactcaa ctgctgttaa atggcagtct agcagaagaa     720
```

```
gaggtagtaa ttagatccga aaatttcgcg gacaatgcta aaaccataat agtacagctg    780
aatgaatctg tagaaattaa ttgtacaaga cccaacaaca atacaagaaa aagtatacat    840
ataggaccag gcagagcatt atatacaaca ggagaaataa taggagatat aagacaagca    900
cattgtaacc ttagtagagc aaaatggaat gacactttaa ataagatagt tataaaatta    960
agagaacaat ttgggaataa aacaatagtc tttaagcatt cctcaggagg ggacccagaa   1020
attgtgacgc acagttttaa ttgtggaggg gaatttttct actgtaattc aacacaactg   1080
tttaatagta cttggaatgt tactgaagag tcaaataaca ctgtagaaaa taacacaatc   1140
acactcccat gcagaataaa acaaattata aacatgtggc agaaagtagg aagagcaatg   1200
tatgcccctc ccatcagagg acaaattaga tgttcatcaa atattacagg gctgctatta   1260
acaagagatg gtggtccaga ggcaaacaag accgaggtct tcagacctgg aggaggagat   1320
atgagggaca attggagaag tgaattatat aaatataaag tagtaaaaat tgaaccatta   1380
ggagtagcac ccaccaaggc aaagagaaga gtggtggagt aa                      1422
```

<210> SEQ ID NO 8
<211> LENGTH: 1422
<212> TYPE: DNA
<213> ORGANISM: Artificial Sequence
<220> FEATURE:
<223> OTHER INFORMATION: Codon optimized gp120.Bal DNA sequence

<400> SEQUENCE: 8

```
ctgtgggtga ccgtgtacta cggcgtgccc gtgtggaagg aggccaccac caccctgttc     60
tgcgccagcg accgcaaggc ctacgacacc gaggtgcaca acgtgtgggc cacccacgcc    120
tgcgtgccca ccgaccccaa cccccaggag gtggagctga agaacgtgac cgagaacttc    180
aacatgtgga agaacaacat ggtggagcag atgcacgagg acatcatcag cctgtgggac    240
cagagcctga agccctgcgt gaagctgacc cccctgtgcg tgaccctgaa ctgcaccgac    300
ctgcgcaacg ccaccaacgg caacgacacc aacaccacta gtagcagccg cggcatggtg    360
ggcggcggcg agatgaagaa ctgcagcttc aacatcacca ccaacatccg cggcaaggtg    420
cagaaggagt acgccctgtt ctacaagctg gacatcgccc ccatcgacaa caacagcaac    480
aaccgctacc gcctgatcag ctgcaacacc agcgtgatca cccaggcctg ccccaaggtg    540
agcttcgagc ccatccccat ccactactgc gcccccgccg gcttcgccat cctgaagtgc    600
aaggacaaga agttcaacgg caagggcccc tgcaccaacg tgagcaccgt gcagtgcacc    660
cacggcatcc gccccgtggt gagcacccag ctgctgctga acggcagcct ggccgaggag    720
gaggtggtga tccgcagcgc caacttcgcc gacaacgcca aggtgatcat cgtgcagctg    780
aacgagagcg tggagatcaa ctgcacccgc cccaacaaca acacccgcaa gtccatccac    840
atcggccccg gccgcgcctt ctacaccacc ggcgagatca tcggcgacat ccgccaggcc    900
cactgcaacc tgagccgcgc caagtggaac gacaccctga acaagatcgt gatcaagctg    960
cgcgagcagt tcggcaacaa gaccatcgtg ttcaagcaca gcagcggcgg cgaccccgag   1020
atcgtgaccc acagcttcaa ttgcggcggc gagttcttct actgcaacag cacccagctg   1080
ttcaacagca cctggaacgt gaccgaggag agcaacaaca ccgtggagaa caacaccatc   1140
accctgccct gccgcatcaa gcagatcatc aacatgtggc aggaggtggg ccgcgccatg   1200
tacgcccccc ccatccgcgg ccagatccgc tgcagttcga acatcaccgg cctgctgctg   1260
acccgcgacg gcggccccga ggacaacaag accgaggtgt tccgccccgg cggcggcgac   1320
atgcgcgaca actggcgcag cgagctgtac aagtacaagg tggtgaagat cgagcccctg   1380
```

ggcgtggccc ccaccaaggc caagcgccgc gtggtggagt aa 1422

<210> SEQ ID NO 9
<211> LENGTH: 1422
<212> TYPE: DNA
<213> ORGANISM: Human immunodeficiency virus

<400> SEQUENCE: 9
ttgtgggtca cagtctatta tggggtacct gtgtggaaag aagcaaacac cactctattt 60
tgtgcatcag atgctaaagc atatgataca gaggtacata atgtttgggc cacacatgcc 120
tgtgtaccca cagaccccga tccacaagaa gtagaattgg aaaatgtgac agaaaatttt 180
aacatgtgga aaaataacat ggtagaacag atgcatgagg atataattag tttatgggat 240
caaagcctaa agccatgtgt aaaattaacc ccactctgtg ttactctaaa ttgcaccaat 300
ctgaggaatg atactaatac cacgaggaat gctactaata ccacgagtag tgagacaatg 360
atggaggagg gagaaataaa aaattgctct ttcaatatca ccacaagcat aagagataag 420
gtgcaaaaag aatttgcact tttttataaa cttgatgtag taccaataga aaatgatact 480
actagctata ggttgataag ttgtaatacc tcagtcctta cacaggcctg cccaaaggta 540
tcctttgagc caattcccat acatttttgt gccccggctg gttttgcaat tctaaagtgt 600
aaagataaga agttcaatgg aacaggacca tgtacaaatg tcagcacagt acaatgcaca 660
catggaatta agccagtagt atcaactcaa ctgctgttaa atggcagtct agcagaagaa 720
gaggtagtaa ttaggtccgc caatctctcg gacaatgcta aaaccataat agtacagctg 780
aatgaatctg tacaaatgaa ttgtacgaga cccaacaaca atacaagaaa aagtatacat 840
ataggaccag gcagagcatt ttatacaaca ggagaaataa taggagatat aagacaagca 900
cattgtaacc ttagtagaac aaaatggaat gaaactttaa aaaggatagt tataaaatta 960
agagagcaat atgagaataa aacaatagtc tttaatcaat cctcaggagg ggacccagaa 1020
attgtaatgc tcagctttaa ttgtggaggg gaatttttct actgtaattc aacaaaactg 1080
tttaatagta cttggaatgg tactgagtca aataacacag gagatgaccc aatcgtactc 1140
ccatgcagaa taaaacaagt tataaacatg tggcaagaag taggaaaagc aatgtatgcc 1200
cctcccatca gaggacaaat tagatgctca tcaaatatta caggactgct attaacaaga 1260
gatggtggta acagtaacga gaccaatacc accgagatct tcagacctgg gggaggaaat 1320
atgaaggaca attggagaag tgaattatat aaatataaag tagtaagaat tgaaccatta 1380
ggaatagcac ccaccagggc aaagagaaga gtggtggagt aa 1422

<210> SEQ ID NO 10
<211> LENGTH: 1422
<212> TYPE: DNA
<213> ORGANISM: Artificial Sequence
<220> FEATURE:
<223> OTHER INFORMATION: Codon optimized gp120.B DNA sequence

<400> SEQUENCE: 10
ctgtgggtga ccgtctacta tggggtgcct gtgtggaagg aggccaacac cactctgttc 60
tgcgcttctg acgctaaggc ctacgatacc gaggtgcaca atgtgtgggc cacccacgcc 120
tgtgtgccca ccgaccccga ccctcaggag gtggagctgg agaacgtgac cgaaaacttc 180
aacatgtgga agaataacat ggtggagcag atgcatgagg atatcattag cctgtgggac 240
cagagcctaa agccctgcgt gaagctgacc cccctgtgtg tgactctgaa ctgcaccaac 300
ctgaggaatg atactaacac caccaggaac gccactaata cgaccagcag cgagaccatg 360
atggaggagg gcgagatcaa gaactgctct ttcaacatca ccacgagcat cagagacaag 420
gtgcagaagg agtttgccct tttctataaa cttgatgtgg tgcctatcga gaatgacact 480
actagctaca ggctgatcag ctgcaacacc agcgtcctga cacaggcctg ccccaaggtg 540
tccttcgagc caattcccat ccacttttgt gccccggctg gtttcgccat tctaaagtgc 600
aaggataaga agttcaacgg caccggtcct tgtaccaatg tcagcaccgt acaatgcacc 660
cacggcatta agcccgtggt gagcactcag ctgctgctga acggcagcct ggccgaggaa 720
gaggtggtga ttcgctccgc caacctctct gacaatgcta agaccataat cgtgcagctg 780
aacgagtctg tgcagatgaa ctgcacgagg cccaacaaca ataccaggaa gagtatccat 840
atcggtcccg gcagggcatt ctataccacc ggcgagatca tcggcgacat caggcaggcc 900
cactgtaacc ttagcaggac aaagtggaac gagactctga agaggatcgt gatcaagctg 960
agggagcagt acgagaacaa gaccatcgtc tttaatcaat ccagcggcgg ggaccctgag 1020
attgtgatgc tgagcttcaa ctgcggtggg gagttcttct actgtaactc aaccaagctg 1080
tttaatagca cttggaacgg cactgagtct aacaacaccg gtgatgaccc catcgtgctg 1140
ccatgcagga tcaagcaggt gatcaacatg tggcaggaag tgggcaaggc catgtatgcc 1200
cctcccatca ggggtcagat taggtgcagc agcaatatta ccggcctgct actgacccgc 1260
gacggcggta acagcaacga gaccaacacc accgagatct tcaggcctgg gggcggcaac 1320
atgaaggaca attggaggag cgagttatac aaatataagg tggtgaggat tgagcctctg 1380
ggtatcgccc ccaccagggc caagaggagg gtggtgcagt aa 1422

<210> SEQ ID NO 11
<211> LENGTH: 1443
<212> TYPE: DNA
<213> ORGANISM: Human immunodeficiency virus

<400> SEQUENCE: 11
ttgtgggtca cagtctatta tggggtacct gtgtggaaag aagcaaaaac tactctattc 60
tgtgcatcag atgctaaatc atatgagaaa gaagtgcata atgtctgggc tacacatgcc 120
tgtgtaccca cagaccccaa cccacaagaa atagttttgg gaaatgtaac agaaaatttt 180
aacatgtgga aaaatgacat ggtggatcag atgcatgagg atataatcag tttatgggat 240
caaagcctaa agccatgtgt aaagttgacc ccactctgtg tcactttaaa ttgtacagag 300
gttaatgtta ccagaaatgt taataatagc gtggttaata ataccacaaa tgttaataat 360
agcatgaatg gagacatgaa aaattgctct ttcaacataa ccacagaact aaaagataag 420
aaaaagaatg tgtatgcact tttttataaa cttgatatag tatcacttaa tgagactgac 480
gactctgaga ctggcaactc tagtaaatat tatagattaa taaattgtaa tacctcagcc 540
ctaacacaag cctgtccaaa ggtctctttt gacccaattc ctatacatta ttgtgctcca 600
gctggttatg cgattctaaa gtgtaataat aagacattca atgggacagg accatgccat 660
aatgtcagca cagtacaatg tacacatgga attaagccag tggtatcaac tcaactactg 720
ttaaatggta gcctagcaga agaagggata ataattagat ctgaaaatct gacaaacaat 780
gtcaaaacaa taatagtaca tcttaataga tctatagaaa ttgtgtgtgt aagacccaac 840
aataatacaa gacaaagtat aagaatagga ccaggacaaa cattctatgc aacaggagac 900
ataataggag acataagaca agcacattgt aacattagta ggactaactg gactaagact 960
ttacgagagg taaggaacaa attaagagaa cacttcccta ataaaaacat aacatttaaa 1020
ccatcctcag gaggggacct agaaattaca acacatagct ttaattgtag aggagaattt 1080
ttctattgca atacatcggg cctgtttagt ataaattata cagaaaataa tacagatggt 1140
acacccatca cactcccatg cagaataaga caaattataa atatgtggca ggaagtagga 1200
cgagcaatgt acgcccctcc cattgaagga aacatagcat gtaaatcaga tatcacaggg 1260
ctactattgg ttcgggatgg aggaagcaca aatgatagca caaataataa cacagagata 1320
ttcagacctg caggaggaga tatgagggac aattggagga gtgaattgta taagtataaa 1380
gtggtagaaa ttaagccatt gggaatagca cccactgagg caaaaaggag agtggtggag 1440
taa 1443

<210> SEQ ID NO 12
<211> LENGTH: 1464
<212> TYPE: DNA
<213> ORGANISM: Artificial Sequence
<220> FEATURE:
<223> OTHER INFORMATION: Codon optimized gp120.Czm DNA sequence

<400> SEQUENCE: 12
tggggcaacc tgtgggtgac cgtgtactac ggcgtgcccg tgtggaagga ggccaagacc 60
accctgttct gcgccagcga cgccaagagc tacgagaagg aggtgcacaa cgtgtgggcc 120
acccacgcct gcgtgcccac cgaccccaac ccccaggaga tcgtgctggg caacgtgacc 180
gagaacttca acatgtggaa gaacgacatg gtggaccaga tgcacgagga catcatcagc 240
ctgtgggacc agagcctgaa gccctgcgtg aagctgaccc ccctgtgcgt gaccctgaac 300
tgcaccgagg tgaacgtgac ccgcaacgtg aacaacagcg tggtgaacaa caccaccaac 360
gtgaacaaca gcatgaacgg cgacatgaag aactgcagct tcaacatcac caccgagctg 420
aaggacaaga agaagaacgt gtacgccctg ttctacaagc tggacatcgt gagcctgaac 480
gagaccgacg acagcgagac cggcaacagc agcaagtact accgcctgat caactgcaac 540
accagcgccc tgacccaggc ctgccccaag gtgagcttcg accccatccc catccactac 600
tgcgcccccg ccggctacgc catcctgaag tgcaacaaca agaccttcaa cggcaccggc 660
ccctgccaca acgtgagcac cgtgcagtgc acccacggca tcaagcccgt ggtgagcacc 720
cagctgctgc tgaacggcag cctggccgag gagggcatca tcatccgcag cgagaacctg 780
accaacaacg tgaagaccat catcgtgcac ctgaaccgca gcatcgagat cgtgtgcgtg 840
cgccccaaca acaacacccg ccagagcatc cgcatcggcc ccggccagac cttctacgcc 900
accggcgaca tcatcggcga catccgccag gcccactgca acatcagccg caccaactgg 960
accaagaccc tgcgcgaggt gcgcaacaag ctgcgcgagc acttccccaa caagaacatc 1020
accttcaagc ccagcagcgg cggcgacctg gagatcacca cccacagctt caactgccgc 1080
ggcgagttct tctactgcaa caccagcggc ctgttcagca tcaactacac cgagaacaac 1140
accgacggca cccccatcac cctgccctgc cgcatccgcc agatcatcaa catgtggcag 1200
gaggtgggcc gcgccatgta cgcccccccc atcgagggca acatcgcctg caagagcgac 1260
atcaccggcc tgctgctggt gcgcgacggc ggcagcacca acgacagcac caacaacaac 1320
accgagatct tccgccccgc cggcggcgac atgcgcgaca actggcgcag cgagctgtac 1380
aagtacaagg tggtggagat caagcccctg ggcatcgccc ccaccgaggc caagcgccgc 1440
gtggtggagc gcgagaagcg ctga 1464

<210> SEQ ID NO 13
<211> LENGTH: 1407
<212> TYPE: DNA
<213> ORGANISM: Human immunodeficiency virus

<400> SEQUENCE: 13

```
ttgtgggtca cagtctatta tggggtacct gtgtggaaag atgcagatac caccctattt     60
tgtgcatcag atgccaaagc acatgagaca gaagtgcaca atgtctgggc cacacatgcc    120
tgtgtaccca cagaccccaa cccacaagaa atacacctgg aaaatgtaac agaaaatttt    180
aacatgtgga aaaataaaat ggtagagcag atgcaggagg atgtaatcag tttatgggat    240
caaagtctaa agccatgtgt aaagttaact cctctctgcg ttactttgac ttgtaccaat    300
gctactctga attgtaccaa tttgaccaat ggcaataaga caactaatgt ctctaacata    360
ataggaaatc taacagatga agtaagaaac tgttcttttc atatgaccac agaactaaga    420
gataagaagc agaaggtcta tgcacttttt tataagcttg atatagtaca aattaatagt    480
agtgagtata ggttaataaa ttgtaatact tcagtcatta agcaggcttg tccaaagata    540
tcctttgatc caattcctat acattattgt actccagctg gttatgcgat tttaaagtgt    600
aatgataaga atttcaatgg gacagggcca tgtaaaaatg tcagctcagt acaatgcaca    660
catggaatta agccagtggt atcaactcaa ttgctgttaa atggcagtct agcagaagaa    720
gagataataa tcagctctga aaatctcaca aacaatgcca aaaccataat agtgcacctt    780
aataaatctg tagaaatcag ttgtaccaga ccctccacca atacaagaac aagtatacgt    840
ataggaccag gacaagtatt ctatagaaca ggagacataa caggagatat aagaaaagca    900
tattgtgaga ttaatgaaac aaaatggaat gaagctttaa aacaggtagc tgggaaatta    960
aaagaacact ttaataagac aataatcttt caaccaccct caggaggaga tctagaaatt   1020
acaatgcatc attttaattg tagaggggaa tttttctatt gcgatacaac acaactgttt   1080
aatagaactt ggggagaaaa tgaaaccaga gaggggcgta atatcacact tccatgcaag   1140
ataaagcaaa ttgtaaacat gtggcaggga gcagggcaag caatgtatgc tcctcccatc   1200
agtggaataa ttaagtgtgt atcaaatatt acaggaatac tattgacaag agatggtggt   1260
gctaataatt cggctagtga gaccttcaga cctggaggag gaaatataaa ggacaattgg   1320
agaagtgaat tatataaata taaagtagta caaattgaac cactaggaat agcacccacc   1380
agggcaaaga gaagagtggt ggagtaa                                       1407
```

<210> SEQ ID NO 14
<211> LENGTH: 1407
<212> TYPE: DNA
<213> ORGANISM: Artificial Sequence
<220> FEATURE:
<223> OTHER INFORMATION: Codon optimized gp120.E DNA sequence

<400> SEQUENCE: 14

```
ctgtgggtga ccgtgtacta cggcgtgccc gtgtggaagg acgccgacac caccctgttc     60
tgcgccagcg acgccaaggc ccacgagacc gaggtgcaca acgtgtgggc cacccacgcc    120
tgcgtgccca ccgaccccaa cccccaggag atccacctgg agaacgtgac cgagaacttc    180
aacatgtgga agaacaagat ggtggagcag atgcaggagg acgtgatcag cctgtgggac    240
cagagcctga agccctgcgt gaagctgacc cccctgtgcg tgaccctgac ctgcaccaac    300
gccaccctga actgcaccaa cctgaccaac ggcaacaaga ccaccaacgt gagcaacatc    360
atcggcaacc tgaccgacga ggtgcgcaac tgcagcttcc acatgaccac cgagctgcgc    420
gacaagaagc agaaggtgta cgccctgttc tacaagctgg acatcgtgca gatcaacagc    480
agcgagtacc gcctgatcaa ctgcaacacc agcgtgatca agcaggcctg ccccaagatc    540
agcttcgacc ccatccccat ccactactgc acccctgctg gctacgccat cctgaagtgc    600
```

-continued aacgacaaga acttcaacgg caccggaccc tgcaagaacg tgagcagcgt gcagtgcacc 660
cacggcatca agcccgtggt gagcacccag ctgctgctga acggcagcct ggccgaggag 720
gagatcatca tcagcagcga gaacctgacc aacaacgcca agaccatcat cgtgcacctg 780
aacaagagcg tggagatcag ctgcactcgc cccagcacca acacccgcac cagcatccgc 840
atcggacctg gccaggtgtt ctaccgcacc ggcgacatca ccggcgacat ccgcaaggcc 900
tactgcgaga tcaacgagac caagtggaac gaggccctga agcaggtggc cggcaagctg 960
aaggagcact tcaacaagac catcatcttc cagcctccca gcggaggcga cctggagatc 1020
accatgcacc acttcaactg cagaggcgag ttcttctact gcgacaccac ccagctgttc 1080
aaccgcacct ggggcgagaa cgagacccgc gagggcagga acatcaccct gccctgcaag 1140
atcaagcaga tcgtgaacat gtggcaggga gctggccagg ccatgtacgc cccacccatc 1200
agcggcatca tcaagtgcgt gagcaacatc accggcatcc tgctgacccg cgacggcggt 1260
gccaacaaca gcgccagcga gaccttcagg ccaggcggtg gcaacatcaa ggacaactgg 1320
cgcagcgagc tgtacaagta caaggtggtg cagatcgagc ccctgggcat cgcccccact 1380
cgcgccaagc gccgcgtggt ggagtaa 1407

<210> SEQ ID NO 15
<211> LENGTH: 1410
<212> TYPE: DNA
<213> ORGANISM: Human immunodeficiency virus

<400> SEQUENCE: 15
ttgtgggtca cagtctatta tggggtacct gtgtggaaag atgcagagac taccttattt 60
tgtgcatcag atgcgaaagc atatgataca gaagtgcata atgtctgggc tacgcatgcc 120
tgtgtaccta cagaccccaa cccacaagaa atatatatgg aaaatgtgac agaagagttt 180
aacatgtgga aaaataacat ggtagagcag atgcatacag atataatcag tctatgggac 240
caaagcctaa aaccatgtgt acagttaacc cctctctgcg ttactttaga ttgtagctat 300
aacatcacca ataatatcac caatagcatc accaatagct cagttaacat gagagaagaa 360
ataaaaaact gctctttcaa tatgaccaca gaattaaggg ataagaatcg gaaggtatat 420
tcactttttt ataaacttga tgtagtacaa attaataatg gtaataacag tagtaatctg 480
tatagattaa taaattgtaa tacctcagcc cttacacagg cttgtccaaa ggtaaccttt 540
gagccaattc ccatacgtta ttgtgcccca gctggttatg cgattctaaa atgtaatgat 600
aaggagttca atggaacagg gctatgcaaa aatgtcagca cagtgcaatg cacacatgga 660
atcaggccag tagtatcaac tcaactgctg ttaaatggca gtttagcaga aggaaaggta 720
atgattagat ctgaaaatat cacaaacaat gtcaaaaaca taatagtaca acttaacgag 780
actgtaacaa ttaattgtac cagacctaac aacaatacaa gaaaaagtgt acgtatagga 840
ccaggacaaa cattctatgc aacaggtgat ataatagggg atataagaca agcacattgt 900
aatgtcagtg ggtcacaatg gaatagagct ttacaccagg tagttggaca attaagagaa 960
tactggaaca caacaataat ctttaaaaac tcctcaggag gggatttaga aattacaaca 1020
catagtttta attgtggagg agaatttttc tattgtaata catcaggcct gtttaatagt 1080
aattggacac ataatgacac tgccagcatg aaaccaaatg acactataac actcccatgc 1140
agaataaagc aaattataaa tatgtggcag agagtaggac aagcaatata tgcccctccc 1200
attcaaggag taataaggtg tgaatcaaac attacaggac taatattaac aagagatggt 1260
gggggtaaca tcaatgaaag tcaaatcttc agacctggag gaggagatat gagggacaat 1320

```
tggagaagtg aattatataa gtataaggta gtaagaattg aaccactagg agtagcaccc   1380

accaaggcaa agagaagagt ggtggagtaa                                    1410


<210> SEQ ID NO 16
<211> LENGTH: 1410
<212> TYPE: DNA
<213> ORGANISM: Artificial Sequence
<220> FEATURE:
<223> OTHER INFORMATION: Codon optimized gp120.A DNA sequence

<400> SEQUENCE: 16

ctgtgggtga ccgtgtacta cggcgtgccc gtgtggaagg acgccgagac caccctgttc     60

tgcgccagcg acgccaaggc ctacgacacc gaggtgcaca acgtgtgggc cacccacgcc    120

tgcgtgccca ccgaccccaa cccccaggag atctacatgg agaacgtgac cgaggagttc    180

aacatgtgga agaacaacat ggtggagcag atgcacaccg acatcatcag cctgtgggac    240

cagagcctga agccctgcgt gcagctgacc cccctgtgcg tgaccctgga ctgcagctac    300

aacatcacca acaacatcac caacagcatc accaacagca gcgtgaacat gcgcgaggag    360

atcaagaact gcagcttcaa catgaccacc gagctgcgcg acaagaaccg caaggtgtac    420

agcctgttct acaagctgga cgtggtgcag atcaacaacg gcaacaacag cagcaacctg    480

taccgcctga tcaactgcaa caccagcgcc ctgacccagg cctgccccaa ggtgaccttc    540

gagcccatcc ccatccgcta ctgcgccccc gccggctacg ccatcctgaa gtgcaacgac    600

aaggagttca acggcaccgg cctgtgcaag aacgtgagca ccgtgcagtg cacccacggc    660

atccgccccg tggtgagcac ccagctgctg ctgaacggca gcctggccga gggcaaggtg    720

atgatccgca gcgagaacat caccaacaac gtgaagaaca tcatcgtgca gctgaacgag    780

accgtgacca tcaactgcac ccgccccaac aacaacaccc gcaagagcgt gcgcatcggc    840

cccggccaga ccttctacgc caccggcgac atcatcggcg acatccgcca ggcccactgc    900

aacgtgagcg gcagccagtg gaaccgcgcc ctgcaccagg tggtgggcca gctgcgcgag    960

tactggaaca ccaccatcat cttcaagaac agcagcggcg gcgacctgga gatcaccacc   1020

cacagcttca actgcggcgg cgagttcttc tactgcaaca ccagcggcct gttcaacagc   1080

aactggaccc acaacgacac cgccagcatg aagcccaacg acaccatcac cctgccctgc   1140

cgcatcaagc agatcatcaa catgtggcag cgcgtgggcc aggccatcta cgcccctccc   1200

atccagggcg tgatccgctg cgagagcaac atcaccggcc tgatcctgac ccgcgacggc   1260

ggcggcaaca tcaacgagag ccagatcttc cgccccggcg gcggcgacat gcgcgacaac   1320

tggcgcagcg agctgtacaa gtacaaggtg gtgcgcatcg agcccctggg cgtggccccc   1380

accaaggcca agcgccgcgt ggtggagtaa                                    1410


<210> SEQ ID NO 17
<211> LENGTH: 470
<212> TYPE: PRT
<213> ORGANISM: Human immunodeficiency virus

<400> SEQUENCE: 17

Ser Leu Trp Val Thr Val Tyr Tyr Gly Val Pro Val Trp Lys Asp Ala
 1               5                  10                  15

Glu Thr Thr Leu Phe Cys Ala Ser Asp Ala Lys Ala Tyr Asp Thr Glu
            20                  25                  30

Val His Asn Val Trp Ala Thr His Ala Cys Val Pro Thr Asp Pro Asn
        35                  40                  45
```

-continued

```
Pro Gln Glu Ile Tyr Met Glu Asn Val Thr Glu Glu Phe Asn Met Trp
    50                  55                  60

Lys Asn Asn Met Val Glu Gln Met His Thr Asp Ile Ile Ser Leu Trp
65                  70                  75                  80

Asp Gln Ser Leu Lys Pro Cys Val Gln Leu Thr Pro Leu Cys Val Thr
                85                  90                  95

Leu Asp Cys Ser Tyr Asn Ile Thr Asn Asn Ile Thr Asn Ser Ile Thr
            100                 105                 110

Asn Ser Ser Val Asn Met Arg Glu Glu Ile Lys Asn Cys Ser Phe Asn
        115                 120                 125

Met Thr Thr Glu Leu Arg Asp Lys Asn Arg Lys Val Tyr Ser Leu Phe
    130                 135                 140

Tyr Lys Leu Asp Val Val Gln Ile Asn Asn Gly Asn Asn Ser Ser Asn
145                 150                 155                 160

Leu Tyr Arg Leu Ile Asn Cys Asn Thr Ser Ala Leu Thr Gln Ala Cys
                165                 170                 175

Pro Lys Val Thr Phe Glu Pro Ile Pro Ile Arg Tyr Cys Ala Pro Ala
            180                 185                 190

Gly Tyr Ala Ile Leu Lys Cys Asn Asp Lys Glu Phe Asn Gly Thr Gly
        195                 200                 205

Leu Cys Lys Asn Val Ser Thr Val Gln Cys Thr His Gly Ile Arg Pro
    210                 215                 220

Val Val Ser Thr Gln Leu Leu Leu Asn Gly Ser Leu Ala Glu Gly Lys
225                 230                 235                 240

Val Met Ile Arg Ser Glu Asn Ile Thr Asn Asn Val Lys Asn Ile Ile
                245                 250                 255

Val Gln Leu Asn Glu Thr Val Thr Ile Asn Cys Thr Arg Pro Asn Asn
            260                 265                 270

Asn Thr Arg Lys Ser Val Arg Ile Gly Pro Gly Gln Thr Phe Tyr Ala
        275                 280                 285

Thr Gly Asp Ile Ile Gly Asp Ile Arg Gln Ala His Cys Asn Val Ser
    290                 295                 300

Gly Ser Gln Trp Asn Arg Ala Leu His Gln Val Val Gly Gln Leu Arg
305                 310                 315                 320

Glu Tyr Trp Asn Thr Thr Ile Ile Phe Lys Asn Ser Ser Gly Gly Asp
                325                 330                 335

Leu Glu Ile Thr Thr His Ser Phe Asn Cys Gly Gly Glu Phe Phe Tyr
            340                 345                 350

Cys Asn Thr Ser Gly Leu Phe Asn Ser Asn Trp Thr His Asn Asp Thr
        355                 360                 365

Ala Ser Met Lys Pro Asn Asp Thr Ile Thr Leu Pro Cys Arg Ile Lys
    370                 375                 380

Gln Ile Ile Asn Met Trp Gln Arg Val Gly Gln Ala Ile Tyr Ala Pro
385                 390                 395                 400

Pro Ile Gln Gly Val Ile Arg Cys Glu Ser Asn Ile Thr Gly Leu Ile
                405                 410                 415

Leu Thr Arg Asp Gly Gly Gly Asn Ile Asn Glu Ser Gln Ile Phe Arg
            420                 425                 430

Pro Gly Gly Gly Asp Met Arg Asp Asn Trp Arg Ser Glu Leu Tyr Lys
        435                 440                 445

Tyr Lys Val Val Arg Ile Glu Pro Leu Gly Val Ala Pro Thr Lys Ala
    450                 455                 460

Lys Arg Arg Val Val Gln
465                 470
```

<210> SEQ ID NO 18
<211> LENGTH: 474
<212> TYPE: PRT
<213> ORGANISM: Human immunodeficiency virus

<400> SEQUENCE: 18

```
Ser Leu Trp Val Thr Val Tyr Tyr Gly Val Pro Val Trp Lys Glu Ala
 1               5                  10                  15

Thr Thr Thr Leu Phe Cys Ala Ser Asp Arg Lys Ala Tyr Asp Thr Glu
            20                  25                  30

Val His Asn Val Trp Ala Thr His Ala Cys Val Pro Thr Asp Pro Asn
        35                  40                  45

Pro Gln Glu Val Glu Leu Lys Asn Val Thr Glu Asn Phe Asn Met Trp
    50                  55                  60

Lys Asn Asn Met Val Glu Gln Met His Glu Asp Ile Ile Ser Leu Trp
65                  70                  75                  80

Asp Gln Ser Leu Lys Pro Cys Val Lys Leu Thr Pro Leu Cys Val Thr
                85                  90                  95

Leu Asn Cys Thr Asp Leu Arg Asn Ala Thr Asn Gly Asn Asp Thr Asn
            100                 105                 110

Thr Thr Ser Ser Ser Arg Gly Met Val Gly Gly Gly Glu Met Lys Asn
        115                 120                 125

Cys Ser Phe Asn Ile Thr Thr Asn Ile Arg Gly Lys Val Gln Lys Glu
    130                 135                 140

Tyr Ala Leu Phe Tyr Lys Leu Asp Ile Ala Pro Ile Asp Asn Asn Ser
145                 150                 155                 160

Asn Asn Arg Tyr Arg Leu Ile Ser Cys Asn Thr Ser Val Ile Thr Gln
                165                 170                 175

Ala Cys Pro Lys Val Ser Phe Glu Pro Ile Pro Ile His Tyr Cys Ala
            180                 185                 190

Pro Ala Gly Phe Ala Ile Leu Lys Cys Lys Asp Lys Lys Phe Asn Gly
        195                 200                 205

Lys Gly Pro Cys Thr Asn Val Ser Thr Val Gln Cys Thr His Gly Ile
    210                 215                 220

Arg Pro Val Val Ser Thr Gln Leu Leu Leu Asn Gly Ser Leu Ala Glu
225                 230                 235                 240

Glu Glu Val Val Ile Arg Ser Ala Asn Phe Ala Asp Asn Ala Lys Val
                245                 250                 255

Ile Ile Val Gln Leu Asn Glu Ser Val Glu Ile Asn Cys Thr Arg Pro
            260                 265                 270

Asn Asn Asn Thr Arg Lys Ser Ile His Ile Gly Pro Gly Arg Ala Phe
        275                 280                 285

Tyr Thr Thr Gly Glu Ile Ile Gly Asp Ile Arg Gln Ala His Cys Asn
    290                 295                 300

Leu Ser Arg Ala Lys Trp Asn Asp Thr Leu Asn Lys Ile Val Ile Lys
305                 310                 315                 320

Leu Arg Glu Gln Phe Gly Asn Lys Thr Ile Val Phe Lys His Ser Ser
                325                 330                 335

Gly Gly Asp Pro Glu Ile Val Thr His Ser Phe Asn Cys Gly Gly Glu
            340                 345                 350

Phe Phe Tyr Cys Asn Ser Thr Gln Leu Phe Asn Ser Thr Trp Asn Val
        355                 360                 365

Thr Glu Glu Ser Asn Asn Thr Val Glu Asn Asn Thr Ile Thr Leu Pro
    370                 375                 380
```

```
Cys Arg Ile Lys Gln Ile Ile Asn Met Trp Gln Glu Val Gly Arg Ala
385                 390                 395                 400

Met Tyr Ala Pro Pro Ile Arg Gly Gln Ile Arg Cys Ser Ser Asn Ile
                405                 410                 415

Thr Gly Leu Leu Leu Thr Arg Asp Gly Gly Pro Glu Asp Asn Lys Thr
            420                 425                 430

Glu Val Phe Arg Pro Gly Gly Gly Asp Met Arg Asp Asn Trp Arg Ser
        435                 440                 445

Glu Leu Tyr Lys Tyr Lys Val Val Lys Ile Glu Pro Leu Gly Val Ala
    450                 455                 460

Pro Thr Lys Ala Lys Arg Arg Val Val Gln
465                 470


<210> SEQ ID NO 19
<211> LENGTH: 474
<212> TYPE: PRT
<213> ORGANISM: Human immunodeficiency virus

<400> SEQUENCE: 19

Ser Leu Trp Val Thr Val Tyr Tyr Gly Val Pro Val Trp Lys Glu Ala
 1               5                  10                  15

Asn Thr Thr Leu Phe Cys Ala Ser Asp Ala Lys Ala Tyr Asp Thr Glu
            20                  25                  30

Val His Asn Val Trp Ala Thr His Ala Cys Val Pro Thr Asp Pro Asp
        35                  40                  45

Pro Gln Glu Val Glu Leu Glu Asn Val Thr Glu Asn Phe Asn Met Trp
    50                  55                  60

Lys Asn Asn Met Val Glu Gln Met His Glu Asp Ile Ile Ser Leu Trp
65                  70                  75                  80

Asp Gln Ser Leu Lys Pro Cys Val Lys Leu Thr Pro Leu Cys Val Thr
                85                  90                  95

Leu Asn Cys Thr Asn Leu Arg Asn Asp Thr Asn Thr Thr Arg Asn Ala
            100                 105                 110

Thr Asn Thr Thr Ser Ser Glu Thr Met Met Glu Glu Gly Glu Ile Lys
        115                 120                 125

Asn Cys Ser Phe Asn Ile Thr Thr Ser Ile Arg Asp Lys Val Gln Lys
    130                 135                 140

Glu Phe Ala Leu Phe Tyr Lys Leu Asp Val Val Pro Ile Glu Asn Asp
145                 150                 155                 160

Thr Thr Ser Tyr Arg Leu Ile Ser Cys Asn Thr Ser Val Leu Thr Gln
                165                 170                 175

Ala Cys Pro Lys Val Ser Phe Glu Pro Ile Pro Ile His Phe Cys Ala
            180                 185                 190

Pro Ala Gly Phe Ala Ile Leu Lys Cys Lys Asp Lys Lys Phe Asn Gly
        195                 200                 205

Thr Gly Pro Cys Thr Asn Val Ser Thr Val Gln Cys Thr His Gly Ile
    210                 215                 220

Lys Pro Val Val Ser Thr Gln Leu Leu Leu Asn Gly Ser Leu Ala Glu
225                 230                 235                 240

Glu Glu Val Val Ile Arg Ser Ala Asn Leu Ser Asp Asn Ala Lys Thr
                245                 250                 255

Ile Ile Val Gln Leu Asn Glu Ser Val Gln Met Asn Cys Thr Arg Pro
            260                 265                 270

Asn Asn Asn Thr Arg Lys Ser Ile His Ile Gly Pro Gly Arg Ala Phe
        275                 280                 285
```

```
Tyr Thr Thr Gly Glu Ile Ile Gly Asp Ile Arg Gln Ala His Cys Asn
    290                 295                 300

Leu Ser Arg Thr Lys Trp Asn Glu Thr Leu Lys Arg Ile Val Ile Lys
305                 310                 315                 320

Leu Arg Glu Gln Tyr Glu Asn Lys Thr Ile Val Phe Asn Gln Ser Ser
                325                 330                 335

Gly Gly Asp Pro Glu Ile Val Met Leu Ser Phe Asn Cys Gly Gly Glu
            340                 345                 350

Phe Phe Tyr Cys Asn Ser Thr Lys Leu Phe Asn Ser Thr Trp Asn Gly
        355                 360                 365

Thr Glu Ser Asn Asn Thr Gly Asp Asp Pro Ile Val Leu Pro Cys Arg
    370                 375                 380

Ile Lys Gln Val Ile Asn Met Trp Gln Glu Val Gly Lys Ala Met Tyr
385                 390                 395                 400

Ala Pro Pro Ile Arg Gly Gln Ile Arg Cys Ser Ser Asn Ile Thr Gly
                405                 410                 415

Leu Leu Leu Thr Arg Asp Gly Gly Asn Ser Asn Glu Thr Asn Thr Thr
            420                 425                 430

Glu Ile Phe Arg Pro Gly Gly Gly Asn Met Lys Asp Asn Trp Arg Ser
        435                 440                 445

Glu Leu Tyr Lys Tyr Lys Val Val Arg Ile Glu Pro Leu Gly Ile Ala
    450                 455                 460

Pro Thr Arg Ala Lys Arg Arg Val Val Gln
465                 470


<210> SEQ ID NO 20
<211> LENGTH: 488
<212> TYPE: PRT
<213> ORGANISM: Human immunodeficiency virus

<400> SEQUENCE: 20

Ser Trp Gly Asn Leu Trp Val Thr Val Tyr Tyr Gly Val Pro Val Trp
 1               5                  10                  15

Lys Glu Ala Lys Thr Thr Leu Phe Cys Ala Ser Asp Ala Lys Ser Tyr
            20                  25                  30

Glu Lys Glu Val His Asn Val Trp Ala Thr His Ala Cys Val Pro Thr
        35                  40                  45

Asp Pro Asn Pro Gln Glu Ile Val Leu Gly Asn Val Thr Glu Asn Phe
    50                  55                  60

Asn Met Trp Lys Asn Asp Met Val Asp Gln Met His Glu Asp Ile Ile
65                  70                  75                  80

Ser Leu Trp Asp Gln Ser Leu Lys Pro Cys Val Lys Leu Thr Pro Leu
                85                  90                  95

Cys Val Thr Leu Asn Cys Thr Glu Val Asn Val Thr Arg Asn Val Asn
            100                 105                 110

Asn Ser Val Val Asn Asn Thr Thr Asn Val Asn Asn Ser Met Asn Gly
        115                 120                 125

Asp Met Lys Asn Cys Ser Phe Asn Ile Thr Thr Glu Leu Lys Asp Lys
    130                 135                 140

Lys Lys Asn Val Tyr Ala Leu Phe Tyr Lys Leu Asp Ile Val Ser Leu
145                 150                 155                 160

Asn Glu Thr Asp Asp Ser Glu Thr Gly Asn Ser Ser Lys Tyr Tyr Arg
                165                 170                 175

Leu Ile Asn Cys Asn Thr Ser Ala Leu Thr Gln Ala Cys Pro Lys Val
            180                 185                 190
```

```
Ser Phe Asp Pro Ile Pro Ile His Tyr Cys Ala Pro Ala Gly Tyr Ala
        195                 200                 205

Ile Leu Lys Cys Asn Asn Lys Thr Phe Asn Gly Thr Gly Pro Cys His
    210                 215                 220

Asn Val Ser Thr Val Gln Cys Thr His Gly Ile Lys Pro Val Val Ser
225                 230                 235                 240

Thr Gln Leu Leu Leu Asn Gly Ser Leu Ala Glu Glu Gly Ile Ile Ile
                245                 250                 255

Arg Ser Glu Asn Leu Thr Asn Asn Val Lys Thr Ile Ile Val His Leu
            260                 265                 270

Asn Arg Ser Ile Glu Ile Val Cys Val Arg Pro Asn Asn Asn Thr Arg
        275                 280                 285

Gln Ser Ile Arg Ile Gly Pro Gly Gln Thr Phe Tyr Ala Thr Gly Asp
    290                 295                 300

Ile Ile Gly Asp Ile Arg Gln Ala His Cys Asn Ile Ser Arg Thr Asn
305                 310                 315                 320

Trp Thr Lys Thr Leu Arg Glu Val Arg Asn Lys Leu Arg Glu His Phe
                325                 330                 335

Pro Asn Lys Asn Ile Thr Phe Lys Pro Ser Ser Gly Gly Asp Leu Glu
            340                 345                 350

Ile Thr Thr His Ser Phe Asn Cys Arg Gly Glu Phe Phe Tyr Cys Asn
        355                 360                 365

Thr Ser Gly Leu Phe Ser Ile Asn Tyr Thr Glu Asn Asn Thr Asp Gly
    370                 375                 380

Thr Pro Ile Thr Leu Pro Cys Arg Ile Arg Gln Ile Ile Asn Met Trp
385                 390                 395                 400

Gln Glu Val Gly Arg Ala Met Tyr Ala Pro Pro Ile Glu Gly Asn Ile
                405                 410                 415

Ala Cys Lys Ser Asp Ile Thr Gly Leu Leu Leu Val Arg Asp Gly Gly
            420                 425                 430

Ser Thr Asn Asp Ser Thr Asn Asn Asn Thr Glu Ile Phe Arg Pro Ala
        435                 440                 445

Gly Gly Asp Met Arg Asp Asn Trp Arg Ser Glu Leu Tyr Lys Tyr Lys
    450                 455                 460

Val Val Glu Ile Lys Pro Leu Gly Ile Ala Pro Thr Glu Ala Lys Arg
465                 470                 475                 480

Arg Val Val Glu Arg Glu Lys Arg
                485


<210> SEQ ID NO 21
<211> LENGTH: 469
<212> TYPE: PRT
<213> ORGANISM: Human immunodeficiency virus

<400> SEQUENCE: 21

Ser Leu Trp Val Thr Val Tyr Tyr Gly Val Pro Val Trp Lys Asp Ala
 1               5                  10                  15

Asp Thr Thr Leu Phe Cys Ala Ser Asp Ala Lys Ala His Glu Thr Glu
            20                  25                  30

Val His Asn Val Trp Ala Thr His Ala Cys Val Pro Thr Asp Pro Asn
        35                  40                  45

Pro Gln Glu Ile His Leu Glu Asn Val Thr Glu Asn Phe Asn Met Trp
    50                  55                  60

Lys Asn Lys Met Val Glu Gln Met Gln Glu Asp Val Ile Ser Leu Trp
65                  70                  75                  80
```

-continued

```
Asp Gln Ser Leu Lys Pro Cys Val Lys Leu Thr Pro Leu Cys Val Thr
                85                  90                  95

Leu Thr Cys Thr Asn Ala Thr Leu Asn Cys Thr Asn Leu Thr Asn Gly
            100                 105                 110

Asn Lys Thr Thr Asn Val Ser Asn Ile Ile Gly Asn Leu Thr Asp Glu
        115                 120                 125

Val Arg Asn Cys Ser Phe His Met Thr Thr Glu Leu Arg Asp Lys Lys
    130                 135                 140

Gln Lys Val Tyr Ala Leu Phe Tyr Lys Leu Asp Ile Val Gln Ile Asn
145                 150                 155                 160

Ser Ser Glu Tyr Arg Leu Ile Asn Cys Asn Thr Ser Val Ile Lys Gln
                165                 170                 175

Ala Cys Pro Lys Ile Ser Phe Asp Pro Ile Pro Ile His Tyr Cys Thr
            180                 185                 190

Pro Ala Gly Tyr Ala Ile Leu Lys Cys Asn Asp Lys Asn Phe Asn Gly
        195                 200                 205

Thr Gly Pro Cys Lys Asn Val Ser Ser Val Gln Cys Thr His Gly Ile
    210                 215                 220

Lys Pro Val Val Ser Thr Gln Leu Leu Leu Asn Gly Ser Leu Ala Glu
225                 230                 235                 240

Glu Glu Ile Ile Ile Ser Ser Glu Asn Leu Thr Asn Asn Ala Lys Thr
                245                 250                 255

Ile Ile Val His Leu Asn Lys Ser Val Glu Ile Ser Cys Thr Arg Pro
            260                 265                 270

Ser Thr Asn Thr Arg Thr Ser Ile Arg Ile Gly Pro Gly Gln Val Phe
        275                 280                 285

Tyr Arg Thr Gly Asp Ile Thr Gly Asp Ile Arg Lys Ala Tyr Cys Glu
    290                 295                 300

Ile Asn Glu Thr Lys Trp Asn Glu Ala Leu Lys Gln Val Ala Gly Lys
305                 310                 315                 320

Leu Lys Glu His Phe Asn Lys Thr Ile Ile Phe Gln Pro Pro Ser Gly
                325                 330                 335

Gly Asp Leu Glu Ile Thr Met His His Phe Asn Cys Arg Gly Glu Phe
            340                 345                 350

Phe Tyr Cys Asp Thr Thr Gln Leu Phe Asn Arg Thr Trp Gly Glu Asn
        355                 360                 365

Glu Thr Arg Glu Gly Arg Asn Ile Thr Leu Pro Cys Lys Ile Lys Gln
    370                 375                 380

Ile Val Asn Met Trp Gln Gly Ala Gly Gln Ala Met Tyr Ala Pro Pro
385                 390                 395                 400

Ile Ser Gly Ile Ile Lys Cys Val Ser Asn Ile Thr Gly Ile Leu Leu
                405                 410                 415

Thr Arg Asp Gly Gly Ala Asn Asn Ser Ala Ser Glu Thr Phe Arg Pro
            420                 425                 430

Gly Gly Gly Asn Ile Lys Asp Asn Trp Arg Ser Glu Leu Tyr Lys Tyr
        435                 440                 445

Lys Val Val Gln Ile Glu Pro Leu Gly Ile Ala Pro Thr Arg Ala Lys
    450                 455                 460

Arg Arg Val Val Gln
465
```